US008637000B2

(12) United States Patent
Morita et al.

(10) Patent No.: US 8,637,000 B2
(45) Date of Patent: Jan. 28, 2014

(54) ANTI-OBESITY AGENT AND ANTI-OBESITY FOOD

(75) Inventors: Hidetoshi Morita, Tama (JP); Toshio Masaoka, Sagamihara (JP); Takehito Suzuki, Yamato (JP)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/150,558

(22) Filed: Jun. 1, 2011

(65) Prior Publication Data

US 2011/0311501 A1 Dec. 22, 2011

Related U.S. Application Data

(62) Division of application No. 11/997,034, filed as application No. PCT/JP2006/314640 on Jul. 25, 2006, now abandoned.

(30) Foreign Application Priority Data

Jul. 26, 2005 (JP) ................................. 2005-215895

(51) Int. Cl.
*A01N 63/00* (2006.01)
(52) U.S. Cl.
USPC .................... 424/93.45; 424/234.1; 424/93.1; 435/243; 435/252.9
(58) Field of Classification Search
None
See application file for complete search history.

(56) References Cited

U.S. PATENT DOCUMENTS

| 6,399,124 | B1 * | 6/2002 | Lesens et al. ................... 426/61 |
| 7,001,756 | B1 * | 2/2006 | Hsu et al. ................... 435/252.9 |
| 8,309,073 | B2 | 11/2012 | Mayra-Makinen et al. |
| 2004/0062758 | A1 | 4/2004 | Mayra-Makinen et al. |
| 2005/0100531 | A1 | 5/2005 | Bienenstock |
| 2005/0165100 | A1 | 7/2005 | Kudo et al. |
| 2009/0181437 | A1 | 7/2009 | Kudo et al. |

FOREIGN PATENT DOCUMENTS

| EP | 0199535 A2 | 10/1986 |
| EP | 1174416 A1 | 1/2002 |
| EP | 1777794 A2 | 2/2002 |
| EP | 1974734 A1 | 10/2008 |
| JP | 2001 120288 | 5/2001 |
| JP | 2002 58425 | 2/2002 |
| JP | 2003 81855 | 3/2003 |
| JP | 2004-073178 | 3/2004 |
| JP | 2004-524836 | 8/2004 |
| JP | 2005-040123 | 2/2005 |
| JP | 2010-057465 | 3/2010 |
| KR | 10-2004-0014058 | 2/2004 |
| KR | 10-2004-0027180 | 4/2004 |
| KR | 10-2004-0037011 | 5/2004 |
| WO | 00 64854 | 11/2000 |
| WO | 02/060276 A1 | 8/2002 |
| WO | 03 105893 | 12/2003 |
| WO | 03/105893 A2 | 12/2003 |
| WO | WO 2004/014403 A1 | 2/2004 |
| WO | 2004/069178 A2 | 8/2004 |

OTHER PUBLICATIONS

T. Mukai, et al., "Haemagglutination and glycolipid-binding activities of Lactobacillus reuteri", Letters in Applied Microbiology, XP002509880, vol. 27, No. 3, Sep. 1998, pp. 130-134.
Ivan A. Casas, et al., "Validation of the Probiotic Concept: Lactobacillus reuteri Confers Broad-spectrum Protection against Disease in Humans and Animals", Microbial Ecology in Health and Disease, XP009032704, vol. 12 No. 4, Nov. 1, 2000, pp. 247-285.
Ivan A. Casas, et al., "Lactobacillus Reuteri: Overview of a New Probiotic for Humans and Animals", Microecology and Therapy, XP009110515, vol. 26, Jan. 1, 1997, pp. 221-231.
B. W. Wolf, et al., "Safety and Tolerance of Lactobacillus reuteri in Healthy Adult Male Subjects", Microbial Ecology in Health and Disease, XP002035130, vol. 8, No. 2, Mar. 1, 1995, pp. 41-50.
Hidetoshi Morita, et al., "Comparative Genome Analysis of Lactobacillus reuteri and Lactobacillus fermentum Reveal a Genomic Island for Reuterin and Cobalamin Production", DNA Research, XP002509881, vol. 15, No. 3, Jun. 30, 2008, pp. 151-161.
W. Tungjaroenchai, et al., "Influence of Adunct Cultures on Volatile Free Fatty Acids in Reduced-fat Edam Cheeses", Journal Dairy Science, vol. 87, pp. 3224-2004.
Office Action issued Mar. 22, 2012, in CN Patent Application No. 201110150966.X with English Translation.
Notice of Reasons for Rejection issued Apr. 17, 2012 in JP Patent Application No. 2007-528471, submitting in English.
Altschul at al., "Basic Local Alignment Search Tool", J. Mol. Biol. 1990, pp. 403-10, vol. 215.
Mulder et al. "The InterPro Database, 2003 brings increased coverage and new features", Nucleic Acids Research, 2004, pp. 315-18. vol. 31, No. 1.
Ogata et al., "KEGG: Kyoto Encyclopedia of Genes and Genomes", Nucleic Acid Research, 1999, pp. 29-34, vol. 27, 1 No. 1.
Sakiyama et al., "An Automated System for Genome Analysis to Support Microbial Whole-genome Shotgun Sequencing", Biosci. Biotechnol. Biochem., 2000, pp. 670-73, vol. 64, No. 3.
Salzberg et al., "Microbial gene identification using interpolated Markov models", Nucleic Acids Research, 1998, pp. 544-48, vol. 26, No. 2.
Thompson et al., "CLUSTAL W: improving the sensitivity of progressive multiple sequence alignment through sequence weighting, position-specific gas penalties and weight matrix choice", Nucleic Acids Research, 1994. pp. 4673-80, vol. 22, No. 22.
XP-002696591, Linus Pauling Institute, Oregon State University, pages from http://lpi.oregonstate.edu/infocenter/phytochemicals/flavonoids, 2000.
International Search Report and Written Opinion issued Nov. 7, 2006 for Intl. Appln. No. PCT/JP2006/314640.

* cited by examiner

*Primary Examiner* — Jennifer Graser
(74) *Attorney, Agent, or Firm* — K&L Gates LLP

(57) ABSTRACT

An anti-obesity agent containing, as an active ingredient, a microorganism which belongs to the species *Lactobacillus reuteri* and is capable of producing lipases having the amino acid sequences respectively depicted in SEQ ID NO: 1, 3 or 5 or amino acid sequences having deletion, substitution or addition of one or more amino acids in the amino acid sequences respectively depicted in SEQ ID NO: 1, 3 or 5. The anti-obesity agent enables a patient to take a normal meal yet preventing the absorption of a fat into the body which is the primary cause of obesity.

13 Claims, 2 Drawing Sheets

ANTI-OBESITY AGENT AND ANTI-OBESITY FOOD

CROSS-REFERENCE TO RELATED APPLICATIONS

The present application is a divisional of U.S. patent application Ser. No. 11/997,034, filed on Jan. 28, 2008 and now abandoned, which is a 35 U.S.C. §371 National Stage patent application of International patent application PCT/JP2006/314640, filed on Jul. 25, 2006, which claims priority to Japanese patent application JP 2005-215895, filed on Jul. 26, 2005.

TECHNICAL FIELD

The present invention relates to an anti-obesity agent and an anti-obesity food, and in more detail, the invention relates to an anti-obesity agent and an anti-obesity food each capable of inhibiting a lipid from being taken from a digestive tract to prevent obesity from occurring.

BACKGROUND ART

The obesity is a disease in a weight control system which is characterized by an excess of body fat. In the modern society, as the result of lack of exercise and meals with excessive calories, a neutral fat is accumulated in the body, and the number of persons who are judged to be obese continues to increase, resulting in a serious problem.

In order to prevent this obesity, though it is the best to perform exercise for consuming a fat to be ingested, it is actually difficult to perform exercise, and a reduction in the ingestion of a fat is demanded.

However, when it was intended to inhibit the obesity through unreasonable dietary restrictions, an intake of other necessary nutrients was insufficient, or the balance was upset, resulting in possibly adversely affecting the body. It may be said that the same is also applicable to the case where a food which makes a person feel full in spite of less nutrients and which is called a diet food is ingested.

DISCLOSURE OF THE INVENTION

Problems to be Solved by the Invention

Accordingly, it has been eagerly demanded to develop a measure capable of preventing a lipid (triacylglycerol) as a primary cause of obesity from being absorbed into the body while taking a normal meal.

Means for Solving the Problems

The present inventors paid attention to a mechanism where a lipid is absorbed into the body and made studies regarding a method of inhibiting obesity. As a result, it was found that when a microorganism flora within intestine ingests and degrades a lipid, the lipid to be ingested by a person reduces as a result, whereby the obesity can be spontaneously prevented. Then, the present inventors have made extensive and intensive investigations regarding microorganisms capable of ingesting and degrading such a lipid and as a result, found out a microorganism having such an action among those belonging to lactic acid bacteria, leading to accomplishment of the invention.

Specifically, the invention is concerned with an anti-obesity agent comprising, as an active ingredient, a microorganism belonging to the species *Lactobacillus reuteri* and capable of producing lipases respectively depicted in the following amino acid sequences (1) to (3) or amino acid sequences having deletion, substitution or addition of one or more amino acids in the amino acid sequences (1) to (3). The "amino acid sequence having deletion, substitution or addition of one or more amino acids" as referred to herein means a sequence equivalent to the original sequence thereof and refers to a sequence still keeping lipase activity. Examples of such an amino acid sequence include those exhibiting homology of 80% or more.

(1)
MVKLMTLHELANNPTLSGQVRLIENIVYGA
MDGEALHMSILAPWTQRFPKQYQTEPRPLI
VFVQGSSWRTPKMGEEIPQLVQFVRAGYIV
ATVQHRSSIDSHPFPAFLQDVKTAIRFLRA
NAQKYAIDPQQVAIWGTSSGANAAMLVGLT
GDDPRYKVDLYQDESDAVDAVVSCFAPMDV
EKTFEYDANVPGNKLLQYCLLGPDVSKWPE
IEKQMSPLYQVKDGQNYPPFLLFHGDADKV
VPYEQMEKMYMRLKDNGNSVEAYRVKGANH
ERDFWSPTIYNIVQKFLGDQFK (2)
LIYVLKDLCNTIAEVYGKSILKGVFIMKHT
LKVDQVRDGLWLDSDITYTQVPGWLGNTTR
DLKLSVIRHFQTNDDTRYPVIFWFAGGGWM
DTDHNVHLPNLVDFARHGYIVVGVEYRDSN
KVQFPGQLEDAKAAIRYMRANAKRFQADPN
RFIVMGESAGGHMASMLGVTNGLNQFDKGA
NLDYSSDVQVAVPFYGVVDPLTAKTGSASN
DFDFVYRNLLGAEPENAPELDSAANPLTYV
NSNSTPFLIFHGTEDVVVPIKDSEKLYDAL
VENNVPAELYEIEGASHMDVKFLQPQVFKI
VMDFLDKYLTRS (3)
MEIKSVNLDQPYSSLDIYHSNTDKALPGLV
ILPGGSYNQIMERDSERVALTFATHAWQTF
VVRYPVVEHKNYEEAKIAVHQAFEYIVNHA
AELDVDADRLGIIGFSAGGQIAAAYSNEKL
THARFAALGYPVIQPLIDERMGVTTENVAK
LVNPQTPPTFMWGSAKDELTPFVDHLQVYA
DALIKNDIPYELHEFGTGGHGIALANEYTG
IVNNDRVDNHMGKWFPLFLEWLTELNLI (Sequences Above Disclosed as SEQ ID NOS 1, 3 and 5, Respectively, in Order of Appearance)

Also, the invention is concerned with an anti-obesity food comprising, as an active ingredient, a microorganism belonging to the species *Lactobacillus reuteri* and capable of producing lipases respectively depicted in the foregoing amino acid sequences (1) to (3) or amino acid sequences having deletion, substitution or addition of one or more amino acids in the amino acid sequences (1) to (3).

Furthermore, the invention is concerned with a glycerol-degrading enzyme composed of subunits respectively depicted in the following amino acid sequences (5) to (7) or amino acid sequences having deletion, substitution or addition of one or more amino acids in the amino acid sequences (5) to (7). The "amino acid sequence having deletion, substitution or addition of one or more amino acids" as referred to herein means a sequence equivalent to the original sequence thereof and refers to a sequence still keeping glycerol-degrading activity. Examples of such an amino acid sequence include those exhibiting homology of 80% or more.

(5)
MKRQKRFEELEKRPIHQDTFVKEWPEEGFV
AMMGPNDPKPSVKVENGKIVEMDGKKLEDF
DLIDLYIAKYGINIDNVEKVMNMDSTKIAR

-continued

MLVDPNVSRDEIIEITSALTPAKAEEIISK
LDFGEMIMAVKKMRPRRKPDNQCHVTNTVD
NPVQIAADAADAALRGFPPEQETTTAVARYA
PFNAISILIGAQTGRPGVLTQCSVEEATEL
QLGMRGFTAYAETISVYGTDRVFTDGDDTP
WSKGFLASCYASRGLKMRFTSGAGSEVLMG
YPEGKSMLYLEARCILLTKASGVQGLQNGA
VSCIEIPGAVPNGIREVLGENLLCMMCDIE
CASGCDQAYSHSDMRRTERFIGQFIAGTDY
INSGYSSTPNYDNTFAGSNTDAMDYDDMYV
MERDLGQYYGIHPVKEETIIKARNKAAKAL
QAVFEDLGLPKITDEEVEAATYANTHDDMP
KRDMVADMKAAQDMMDRGITAIDIIKALYN
HGFKDVAEAILNLQKQKVVGDYLQTSSIFD
KDWNVTSAVNDGNDYQGPGTGYRLYEDKEE
WDRIKDLPFALDPEHLEL (6)
MADIDENLLRKIVKEVLSETNQIDTKIDFD
KSNDSTATATQEVQQPNSKAVPEKKLDWFQ
PVGEAKPGYSKDEVVIAVGPAFATVLDKTE
TGIPHKEVLRQVIAGIEEEGLKARVVKVYR
SSDVAFCAVQGDHLSGSGIAIGIQSKGTTV
IHQKDQDPLGNLELFPQAPVLTPETYRAIG
KNAAMYAKGESPEPVPAKNDQLARIHYQAI
SAIMHIRETHQVVVGKPEEEIKVTFD (7)
MSEVDDLVAKIMAQMGNSSSANSSTGTSTA
STSKEMTADDYPLYQKHRDLVKTPKGHNLD
DINLQKVVNNQVDPKELRITPEALKLQGEI
AANAGRPAIQKNLQRAAELTRVPDERVLEM
YDALRPFRSTKQELLNIAKELRDKYDANVC
AAWFEEAADYYESRKKLKGDN (Sequences Above Disclosed as SEQ ID NOS 9, 11 and 13, Respectively, in Order of Appearance)

Moreover, the invention is concerned with an enteroadherent protein depicted in the following amino acid sequence (8) or an amino acid sequence having deletion, substitution or addition of one or more amino acids in the amino acid sequence (8). The "amino acid sequence having deletion, substitution or addition of one or more amino acids" as referred to herein means a sequence equivalent to the original sequence thereof and refers to a sequence still keeping activity for making a lactic acid bacterium adhere to the vicinity of intestinal mucosa cells. Examples of such an amino acid sequence include those exhibiting homology of 80% or more.

(SEQ ID NO: 15)
(8)
MFGHDGRIVTKVYQWAGTYYYFDPNTYLRV
DNDYRQSQWGDWYMFGPDGRIVTGLKEWYG
SYYYFDPTTYLKVTNKWIDNKYFGPAGQQA
ISRFERLDNKYYYFDANGAVLNIHDQFKNI
DNHTYYFGADGACYTSQFLNKDGKQYYFDN
DGIMLTDQEKIIDGKFYHFNVNGEAIQVND
PSEI

Effect of the Invention

The anti-obesity agent and anti-obesity food and drink of the invention are able to prevent the absorption of a lipid from the intestinal tract by ingesting them while taking a normal meal. Since lactic acid bacteria are used from old in producing fermented foods such as yogurt and fermented milk and have extremely high safety, they can be ingested without anxiety.

BEST MODES FOR CARRYING OUT THE INVENTION

The microorganism which is an active ingredient of the anti-obesity agent and anti-obesity food and drink of the invention (hereinafter often referred to as "anti-obesity agent and the like") is one belonging to the species *Lactobacillus reuteri* which is a lactic acid bacterium and capable of producing lipases respectively depicted in the foregoing amino acid sequences (1) to (3) (corresponding to SEQ ID NO: 1, 3 and 5, respectively) or amino acid sequences having deletion, substitution or addition of one or more amino acids in the amino acid sequences (1) to (3) (these lipases will be hereinafter referred to as "lipases of the invention") (this microorganism will be hereinafter referred to as "lactic acid bacterium of the invention").

The lipases of the invention degrade a lipid (triacylglycerol) present in the vicinity of intestinal mucosa cells into a fatty acid and glycerol, which are then taken into the lactic acid bacterium of the invention. As shown in FIG. 1, the thus taken fatty acid is utilized as a fungus constituent, and the glycerol is converted into carbon dioxide, acetone, ethanol, lactate or reuterin through various metabolic pathways.

It is preferable that the lactic acid bacterium of the invention has ability for producing the foregoing lipases, namely has the nucleotide sequences (genes) for encoding the foregoing lipases and besides, has a nucleotide sequence as a gene encoding a transporter and depicted in the following (4) (corresponding to SEQ ID NO: 8). The invention also includes a nucleotide sequence having homology of 80% or more with the nucleotide sequence depicted in (4) and encoding a protein having glycerol transporter activity; and a nucleotide sequence for achieving hybridization with the nucleotide sequence depicted in (4) under a stringent condition and encoding a protein having glycerol transporter activity.

(SEQ ID NO: 8)
(4)
ATGCATGGATTTATTGGCGAATTTTTTGGGACCATGGTTTTAATCCTA
TTAGGAGCAGGATGTTGTGCTGGTAATAGTTTGAATAAAACATATGGG
AAACAAAGTGGCTGGTGGTTTATCTGTATTTCATGGGGCTTAGCAGTT
ACAATGGGAGTTTATGTTGCAGGATTTCTGGGTTCATTAGGGCACTTA
AATCCCGCTGTAACAATTCCTTTTGCTATTTTTGGCTTATTCCCATGG
AGTAACGTTATACCTTACTTACTTGGTCAATTTCTTGGTGCGTTTGTT
GGTGCAGTATTAGTAATTATTCAATTCTATCCACAATTTAAAGCAACC
CCAAATGAAGAAGAAGGAAATAATGTTGGTATTTTTGCTACTCGTCCA
GCGATAAATAGTCCAATTTTTAACTTTTTCTCAGAAGTGATTGCGACC
TTTGCATTTATTTTCATCTTATTAAATCTTGGCAACTTTACACAGGGA
TTGAAGCCATTTATCGTAGGAATGGTTATTGCAGTTGTTGGTACATGT
CTCGGGACAACTACTGGCTTTGCATTAAACCCAGCTCGTGATTGGTCA
CCACGTTTAGCATATACTATTTTGCCAATTCCTAATAAGGGTGTTTCA
GAATGGTGGTATGCATGGGTTCCAATGTGTGGCCCAATTGTTGGGGGC
CTTCTTGCTTGTGCTTTACAAACGGCACTAGTTTAG

This gene is one encoding a transporter for taking glycerol into the cell of the lactic acid bacterium of the invention, and, as shown in FIG. 1, the thus taken glycerol is subjected to metabolism by the enzymes within the lactic acid bacterium.

Furthermore, it is preferable that the lactic acid bacterium of the invention is one having a glycerol-degrading enzyme composed of the subunits respectively depicted in the foregoing amino acid sequences (5) to (7) (corresponding to SEQ ID NO: 9, 11 and 13, respectively) or amino acid sequences having deletion, substitution or addition of one or more amino acids in the amino acid sequences (5) to (7). This glycerol-degrading enzyme composed of the subunits (5) to (7) is a glycerol dehydratase which functions in a pdu (propanediol utilization) operon and is able to efficiently metabolize glycerol produced by the action of the lipases of the invention.

It is also possible to obtain a lactic acid bacterium with high glycerol-degrading properties by incorporating the following nucleotide sequences (9) to (11) (corresponding to SED ID NO: 10, 12 and 14, respectively) encoding the subunits (5) to (7) into other lactic acid bacterium or the like by a genetic engineering technique. The invention also includes nucleotide sequences having homology of 80% or more with the nucleotide sequences (9) to (11) and encoding a protein having glycerol-degrading activity; and nucleotide sequences for achieving hybridization with the nucleotide sequences (9) to (11) under a stringent condition and encoding a protein having glycerol-degrading activity.

(SEQ ID NO: 10)
(9)
ATGAAACGTCAAAAACGATTTGAAGAACTAGAAAAACGGCCAATTCAT
CAAGATACATTTGTTAAAGAATGGCCAGAAGAAGGTTTCGTTGCAATG
ATGGGGCCTAATGACCCTAAGCCTAGTGTAAAAGTTGAAAATGGCAAG
ATCGTAGAGATGGATGGTAAAAAGCTCGAAGATTTTGATTTGATTGAC
TTGTACATTGCTAAGTATGGAATCAATATTGACAACGTTGAAAAAGTT
ATGAATATGGATTCTACCAAGATTGCACGGATGGTTGTTGATCCTAAT
GTTTCTGGTGATGAAATTATTGAAATTACATCAGCTTTGACTCCTGCT
AAGGCTGAAGAGATCATCAGTAAGCTTGATTTTGGTGAAATGATTATG
GCTGTCAAGAAGATGCGCCCACGTCGTAAGCCTGACAACCAGTGTCAC
GTTACCAATACTGTTGATAACCCAGTTCAAATTGCTGCTGATCTGCT
GATGCCGCTCTTCGTGGATTTCCAGAACAAGAAACCACGACAGCTGTG
GCACGTTATGCACCATTCAATGCTATTTCAATTTTAATTGGTGCACAA
ACAGGTCGCCCTGGTGTATTGACACAATGTTCTGTTGAAGAAGCTACT
GAATTGCAATTAGGTATGCGTGGTTTTACCGCATATGCTGAAACCATT
TCAGTTTTACGGTACTGATCGTGTATTTACCGATGGTGATGATACTCCA
TGGTCTAAAGGCTTCTTGGCATCTTGTTATGCATCACGTGGTTTGAAG
ATGCGATTTACTTCAGGTGCCGGTTCAGAAGTTTTGATGGGTTATCCA
GAAGGTAAGTCAATGCTTTACCTTGAAGCGCGTTGTATTTTACTTACT
AAGGCTTCAGGTGTTCAAGGACTTCAAAATGGTGCCGTAAGTTGTATT
GAAATTCCTGGTGCTGTTCCTAATGGTATTCGTGAAGTTCTCGGTGAA
AACTTGTTATGTATGATGTGTGACATCGAATGTGCTTCTGGTTGTGAC
CAAGCATACTCACACTCCGATATGCGGCGGACTGAACGGTTTATTGGT
CAATTTATTGCCGGTACTGATTATATTAACTCTGGTTACTCATCAACT
CCTAACTACGATAATACCTTCGCTGGTTCAAACACTGATGCTATGGAC
TACGATGATATGTATGTTATGGAACGTGACTTGGGTCAATATTATGGT
ATTCACCCTGTTAAGGAAGAAACCATTATTAAGGCACGTAATAAGGCC
GCTAAAGCCCTTCAAGCAGTATTTGAAGATCTTGGATTACCAAAGATT
ACTGATGAAGAGGTCGAAGCAGCAACGTATGCTAACACCCATGATGAC
ATGCCAAAGCGGGATATGGTTGCAGATATGAAGGCTGCTCAAGATATG
ATGGATCGTGGAATTACTGCTATTGATATTATCAAGGCATTGTACAAC
CACGGATTTAAAGATGTCGCTGAAGCAATTTTGAACCTTCAAAAACAA
AAAGTTGTTGGTGATTACCTTCAAACATCTTCTATTTTTGATAAAGAT
TGGAACGTCACTTCTGCTGTTAACGACGGAAATGATTATCAAGGACCA
GGTACTGGATACCGTCTATATGAAGACAAGGAAGAATGGGATCGGATT
AAAGACTTACCATTCGCCCTTGATCCAGAACATTTGGAACTGTAG (SEQ ID NO: 12)
(10)
ATGGCTGATATTGATGAAAACTTATTACGTAAAATCGTTAAAGAAGTT
TTAAGCGAAACTAATCAAATCGATACTAAGATTGACTTTGATAAAAGT
AATGATAGTACTGCAACAGCAACTCAAGAGGTGCAACAACCAAATAGT
AAAGCTGTTCCAGAAAAGAAACTTGACTGGTTCCAACCAGTTGGAGAA
GCAAAACCTGGATATTCTAAGGATGAAGTTGTAATTGCAGTCGGTCCT
GCATTCGCAACTGTTCTTGATAAGACAGAAACTGGTATTCCTCATAAA
GAAGTGCTTCGTCAAGTTATTGCTGGTATTGAAGAAGAAGGGCTTAAG
GCGCGGGTAGTTAAAGTTTACCGGAGTTCAGATGTAGCATTCTGTGCT
GTCCAAGGTGATCACCTTTCTGGTTCAGGAATTGCTATTGGTATCCAA
TCAAAAGGGACGACAGTTATTCACCAAAAGGATCAAGACCCTCTTGGT
AACCTTGAGTTATTCCCACAAGCGCCAGTACTTACTCCCGAAACTTAT
CGTGCAATTGGTAAGAATGCCGCTATGTATGCTAAGGGTGAATCTCCA
GAACCAGTTCCAGCTAAAAACGATCAACTTGCTCGTATTCACTATCAA
GCTATTTCAGCAATTATGCATATTCGTGAAACTCACCAAGTTGTTGTT
GGTAAGCCTGAAGAAGAAATTAAGGTTACGTTTGATTAA (SEQ ID NO: 14)
(11)
ATGAGTGAAGTTGATGATTTAGTAGCAAAGATCATGGCTCAGATGGGA
AACAGTTCATCTGCTAATAGCTCTACAGGTACTTCAACTGCAAGTACT
AGTAAGGAAATGACAGCAGATGATTACCCACTTTATCAAAAGCACCGT
GATTTAGTAAAAACACCAAAAGGACACAATCTTGATGACATCAATTTA
CAAAAAGTAGTAAATAATCAAGTTGATCCTAAGGAATTACGGATTACA
CCAGAAGCATTGAAACTTCAAGGTGAAATTGCAGCTAATGCTGGCCGT
CCAGCTATTCAAAAGAATCTTCAACGAGCTGCAGAATTAACACGAGTA
CCTGACGAACGGGTTCTTGAAATGTATGATGCATTGCGTCCTTTCCGT
TCAACTAAGCAAGAATTATTGAACATTGCAAAGGAATTACGGGACAAG
TATGACGCTAATGTTTGCGCAGCATGGTTTGAAGAAGCTGCTGATTAT
TATGAAAGTCGTAAGAAGCTAAAGGGCGATAACTAA

Moreover, it is more preferable that the lactic acid bacterium of the invention is one holding an enteroadherent protein depicted in the following amino acid sequence (8) (corresponding to SEQ ID NO: 15) or an amino acid sequence having deletion, substitution or addition of one or more amino acids in the amino acid sequence (8).

(SEQ ID NO: 15)
(8)
MFGHDGRIVTKVYQWAGTYYYFDPNTYLRV
DNDYRQSQWGDWYMFGPDGRIVTGLKEWYG
SYYYFDPTTYLKVTNKWIDNKYFGPAGQQA
ISRFERLDNKYYYFDANGAVLNIHDQFKNI
DNHTYYFGADGACYTSQFLNKDGKQYYFDN
DGIMLTDQEKIIDGKFYHFNVNGEAIQVND
PSEI

This enteroadherent protein has an action for making a lactic acid bacterium adhere to the vicinity of intestinal mucosa cells, and the lactic acid bacterium of the invention having this is able to exist in the vicinity of an intestinal mucosa for a certain period of time and stably take a lipid thereinto. It becomes possible to obtain a lactic acid bacterium with a long intestinal residence time by incorporating a gene encoding this protein and depicted in the following (12) (corresponding to SEQ ID NO: 16) into other lactic acid bacterium by a known technique. The invention also involves a nucleotide sequence having homology of 80% or more with the nucleotide sequence (12) and encoding a protein having activity for making a lactic acid bacterium adhere to the vicinity of intestinal mucosa cells; and a nucleotide sequence for achieving hybridization with the nucleotide sequence (12) under a stringent condition and encoding a protein having activity for making a lactic acid bacterium adhere to the vicinity of intestinal mucosa cells.

(SEQ ID NO: 16)
(12)
ATGTTCGGTCACGATGGCCGCATTGTTACTAAAGTTTACCAATGGGCT
GGCACGTATTACTACTTTGATCCGAATACTTATTTGCGAGTAGATAAT
GATTACCGTCAATCTCAGTGGGGCGATTGGTATATGTTTGGCCCAGAT
GGTCGTATCGTTACAGGGTTAAAGGAATGGTACGGTAGTTATTATTAC
TTTGATCCGACGACTTACTTAAAAGTAACTAATAAGTGGATAGATAAT
AAGTACTTTGGTCCAGCTGGTCAGCAAGCTATTTCACGCTTTGAGAGA
CTTGATAATAAGTATTACTATTTCGATGCTAATGGGGCAGTTCTTAAT
ATCCATGATCAATTTAAGAATATTGATAACCACACTTATTACTTTGGA
GCTGATGGTGCTTGTTATACCAGTCAATTCTTAAATAAGGATGGTAAA
CAGTATTATTTCGATAATGATGGAATTATGCTCACTGATCAAGAGAAG
ATCATTGACGGTAAATTCTATCATTTCAATGTTAATGGTGAAGCAATC
CAAGTAAATGATCCTTCTGAAATTTGA

Also, it is preferable that the lactic acid bacterium of the invention is one having a glycerol-degrading enzyme depicted in any of the following amino acid sequences (16) to (20) (corresponding to SEQ ID NO: 17, 19, 21, 23 and 25, respectively) or an amino acid sequence having deletion, substitution or addition of one or more amino acids in any of the amino acid sequences (16) to (20). This glycerol-degrading enzyme is an alcohol dehydrogenase (ADH (8) in FIG. 1) and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping glycerol-degrading activity. Examples of such an amino acid sequence include those exhibiting homology of 80% or more.

(SEQ ID NO: 17)
(16)
MKAAVINDPVDGFVTVKDVQLRDLKPGEAL

-continued

```
VDMEYCGLCHTDLHVAAGDFGKKPGRIIGH
EGVGRVSKVAPGVTSLKVGDRVSIAWFFKG
CGHCEYCLTGRETLCRNVLNAGYTADGAMA
EQCIVPADYAVKVPEGLDPVEATSLTCAGV
TMYKALKVADIKPGQWVSIVGAGGLGNLGI
QLAHNVFGAHVIAVDGNPDKLEAAKKNGAE
ILINRHDGDVDKQIQEKVGGVHAAVVTAVS
ASAFDQAVDSLRPDGKLVAVALPQGDMKLN
IAKTVLDGIIVAGSLVGTRQDLAECFQFGA
EGKVHPIVKTRKLSEINDMIQELKDNKVVG
RNVVDFVHNDND
```

(SEQ ID NO: 19)
(17)
```
MEKRENAIPKTMKAWAVTTPGPIDGKESPI
EFTEKPVPTPKRGEVLVKVITCGVCHTDLH
VTEGDLPVHHEHVTPGHEIVGKVVGFGPET
QRFKFGERIGIPWFRHACGVCKFCRSGHEN
LCPHSLYTGWDHDGGYAEYVTVPEGFAYRL
PEKFDSLEAAPLLCAGIIGYRAFERANVPA
GGRLGLYGFGGSAHITAQIALAQGIEVHVF
TRGEDAKKFALELGCASVQGSYDPAPVPLD
SSIIFAPVGDMVLPALASLVPGGTLALAGI
HMTDIPTMNYQKEIFHEKTLTSVESNTRRD
GEEFLTLADRLNIHPEVHEYPLAKADEALR
YVKHGDIKGACVLRVSED
```

(SEQ ID NO: 21)
(18)
```
MQIKAALATKPNADLEIQTVELDEPKENEV
LIKIASTGFCHTDIVGRSGATTPLPVVLGH
EGAGVVQKVGANVTDVKPGDHVVLSFSYCG
HCYNCTHNHQGLCENFNQLNFEGKTYDGTH
RLHLDDGTPVSVFFGQSSFATYVTANVHNI
VKVDQDVDLNLLGPLGCGMQTGAGTVLNYI
KPAPEDAIAVFGAGAVGLAAIMAAKIAGVK
HIIAINRNGNHLDLAKELGATETINNTAED
PVKAIKEIVPRGVTYAIDTTGNTGVIKSAI
DSLATAGECVLLGVGGDITLDLMNDILSES
KKISGVVEGDSNPQEFIPQLVKYYKQSKFP
LDKLVKYYDFADINQVIADSTNGKVIKPII
KIDPELAKLPLTNDGSNVQKMVAEAGLADQ
ITIDSAGTSNIAEGSPADSRTKAILDKYHI
KDDGMIARQLQDRDYYDADYIIAMDQMNVR
DAKDMAPAGLENKVHGIFEATPGKENCYIV
DPWITH
```

(SEQ ID NO: 23)
(19)
```
MKKAIFEKAGQMKIVDVDRPTIEKPDDVII
KVVRTCVCGSDLWNFRGINPVEKDSENSGH
EAIGIVEEVGEDITTVKPGDFVIAPFTHGC
GHCAACRAGFDGSCQSHNDNFSSGVQAQYV
RFQHGQWALVKVPGKPSDYSEGMLKSLLTL
ADVMATGYHAARVANVSDGDTVVVMGDGAV
GLCAIIAAKMRGAKKIISTSRHADRQALAK
EFGATDNVAERSDEAVQKIMELTNGAGADA
VLECVGTEQSTDTAMKVGRPGTIVGRVGLP
HTPKMDMTVLFYNNTIVGGGPASVTTYDKD
VLLKAVLDGDINPGKVFTKSFDLDQIQEAY
EAMDKREAIKSYIIMDGFERD
```

(SEQ ID NO: 25)
(20)
```
MGRLDNKVAIITGGSKGIGAAVAKKFIEEG
AKVVLTARKMDEGQKVADQLGDNAIFIQQD
VARKGDWDRVIRQTVQVFGKLNIVVNNAGI
AEYADVEKTDAEIWDKTIAVNLTGTMWGTK
LGIEAMKNNGEKNSIINMSSIEGLIGDPDL
FAYNASKGGVRLLTKSAALDCARKGYDIRV
NTIHPGYISTPLVDNLVKDDPKAEGHLESL
HPLGRLGKPEEIANLALYLASDESSFSTGS
EFVADGGYTAQ
```

It is also possible to obtain a lactic acid bacterium with high glycerol-degrading properties by incorporating the following nucleotide sequences (32) to (36) (corresponding to SED ID NO: 18, 20, 22, 24 and 26, respectively) encoding the glycerol-degrading enzymes (16) to (20), respectively into other lactic acid bacterium or the like by a genetic engineering technique. The invention also includes a nucleotide sequence having homology of 80% or more with any of the nucleotide sequences (32) to (36) and encoding a protein having glycerol-degrading activity; and a nucleotide sequence for achieving hybridization with any of the nucleotide sequences (32) to (36) under a stringent condition and encoding a protein having glycerol-degrading activity.

(SEQ ID NO: 18)
(32)
```
ATGAAAGCTGCTGTTATTAATGATCCAGTAGACGGTTTTGTTACTGTT
AAAGATGTTCAACTTCGGGATTTGAAGCCCGGTGAAGCTTTAGTTGAC
ATGGAATATTGTGGTCTTTGTCACACTGATCTACACGTTGCTGCTGGG
GACTTTGGTAAGAAGCCCGGTCGTATTATCGGTCACGAAGGGGTTGGT
CGTGTATCTAAGGTTGCCCCTGGCGTTACTTCCTTGAAAGTTGGCGAC
CGTGTATCAATTGCATGGTTCTTCAAGGGCTGTGGACACTGTGAATAT
TGTTTAACTGGTCGTGAAACTCTTTGTCGGAACGTTCTTAATGCGGGT
TACACTGCTGACGGTGCAATGGCTGAACAATGTATCGTACCAGCTGAC
TACGCTGTTAAGGTTCCAGAAGGTCTTGATCCTGTTGAAGCTACTTCA
TTAACTTGTGCTGGTGTTACGATGTACAAGGCATTAAAGGTTGCTGAC
ATCAAGCCAGGTCAATGGGTATCAATCGTTGGTGCTGGTGGTTTAGGT
AACTTGGGTATTCAACTTGCTCACAATCGTATTTGGTGCTCATGTTATC
GCTGTTGATGGTAATCCTGATAAGCTTGAAGCCGCTAAGAAGAATGGT
GCTGAAATTTTAATTAACCGTCATGACGGTGATGTTGATAAGCAAATT
CAAGAAAAGGTTGGCGGTGTTCACGCTGCTGTAGTAACAGCTGTTTCT
GCCTCTGCATTCGACCAAGCAGTTGATTCACTTCGCCCAGATGGTAAG
CTTGTTGCCGTTGCGCTTCCACAAGGTGACATGAAGCTTAACATTGCT
AAGACTGTTCTTGATGGTATCATTGTTGCTGGTTCATTAGTTGGTACC
CGTCAAGACTTAGCTGAATGTTTCCAATTTGGTGCAGAAGGTAAGGTT
CACCCAATTGTTAAGACTCGTAAGTTAAGCGAAATTAATGATATGATC
CAAGAACTTAAGGATAACAAGGTTGTTGGTCGGAATGTTGTTGATTTT
GTTCACAACGATAACGACTAA
```

(SEQ ID NO: 20)
(33)
```
ATGGAAAAACGCGAAAATGCTATTCCGAAAACAATGAAGGCTTGGGCA
GTCACAACTCCTGGGCCGATTGATGGTAAGGAATCAACCAATCGAATTT
ACCGAAAAGCCTGTGCCGACTCCTAAACAGGGAGAAGTCCTTGTTAAG
GTAATAACGTGTGGAGTATGTCATACGGACTTGCACGTGACTGAAGGA
GACTTGCCGGTTCACCACGAACACGTTACTCCTGGTCATGAAATTGTT
GGTAAAGTTGTCGGCTTTGGACCAGAGACACAACGATTTAAGTTTGGT
GAGCGAATTGGGATTCCATGGTTTCGGCATGCTTGGTGGTGATGCAAG
TTTTGCCGATCAGGTCATGAGAATCTCTGTCCTCATTCACTTTATACC
GGTTGGGATCATGATGGCGGTTATGCAGAATATGTCACAGTTCCAGAA
GGATTTGCATATCGGCTTCCAGAAAAGTTTGATTCCCTAGAGGCAGCT
CCGTTATTATGTGCAGGGATTATTGGTTATCGGGCCTTTGAACGTGCA
AATGTTCCGGCTGGCGGTCGCCTAGGATTATATGGCTTCGGTGGTTCA
GCTCATATTACAGCTCAAATTGCACTTGCTCAGGGAATTGAAGTGCAT
GTCTTTACGCGTGGTGAGGATGCCAAGAAATTCGCCCTAGAATTAGGT
TGTGCTTCTGTTCAGGGCTCCTATGACCCAGCACCAGTTCCTTTGGAT
TCATCAATCATTTTTGCGCCGGTTGGTGATATGCTTGCCGGCTTTA
GCTAGTTTAGTTCCAGGGGGGACATTAGCATTAGCCGGTATTCATATG
ACTGATATTCCAACAATGAATTACCAAAAAGAAATATTCCACGAAAAG
ACATTAACGAGTGTTGAGAGTAATTACTGTCGTGATGGGGAAGAATTC
TTAACATTAGCTGATCGTCTTAATATCCATCCTGAAGTCCACGAATAT
CCCCTAGCAAAGGCTGACGAAGCATTACGCTATGTTAAGCACGGTGAT
ATTAAGGGAGCTTGTGTATTACGTGTTAGTGAGGACTAA
```

(SEQ ID NO: 22)
(34)
```
ATGCAAATTAAAGCTGCTCTTGCAACCAAACCTAACGCTGATTTAGAG
ATTCAAACCGTCGAATTGGATGAACCAAAAGAAAATGAAGTATTAATA
AAAATTGCTTCAACAGGTTTTTGTCATACAGATATTGTTGGTCGAAGC
GGTGCCACTACCCCTCTCCCGTTGTCCTCGGGCATGAAGGTCGGGC
GTCGTCCAAAAAGTAGGAGCTAACGTTACGGACGTTAAACCCGGCGAC
CATGTTGTTCTATCATTTAGCTACTGTGGCCATTGCTATAACTGTACT
CATAATCATCAAGGCTTATCGAGAAACTTCAATCAGCTAAACTTTGAA
GGAAAAACCTATGATGGTACTCACGCCTGCACTTAGATGATGGCACG
CCAGTCAGTGTCTTTTTGGTCAGTCTTCCTTTGCGACCTATGTAACA
GCCAATGTCCATAATATTGTTAAAGTTGATCAAGATGTTGATCTTAAC
TTATTAGGGCCACTCGGTTGTGGAATGCAAACAGGTGCTGGAACCGTT
CTAAATTATATTAAACCTGCTCCTGAAGATGCAATTGCCGTTTCGGT
GCTGGTGCTGTTGGCTTAGCCGCAATTATGGCTGCTAAAATTGCTGGA
GTTAAACATATTATTGCGATTAATCGTAACGGTAACCACCTTGACCTG
GCGAAGGAATTGGGCGCTACTGAAACAATTAATAATACGGCTGAAGAT
CCCGTCAAAGCAATTAAAGAAATCGTTCCGCGTGGTGTAACTTATGCA
ATCGATACTACCGGAAACACCGGTGTAATTAAATCAGCAATTGATAGT
CTTGCCACCGCTGGAGAATGTGTCCTCTTAGGAGTTGGCGGCGATATT
ACCTTAGACTTAATGAATGATATCTTATCAGAATCTAAGAAAATCTCT
GGGGTTGTCGAAGGAGATAGCAATCCCCAAGAGTTTATTCCTCAACTA
```

-continued
```
GTTAAGTACTACAAGCAAAGCAAGTTCCCCCTTGATAAGCTTGTTAAG
TACTACGATTTTGCTGATATTAACCAAGTTATCGCTGACTCAACAAAC
GGAAAGGTTATTAAGCCAATCATCAAAATTGATCCTGAATTAGCTAAA
TAATTGCCGCTCACCAATGACGGAAGCAATGTTCAAAAAATGGTTGCA
GAAGCTGGCCTTGCTGATCAAATTACTATTGATTCAGCCGGACAAGT
AACATTGCAGAAGGTTCACCTGCTGATAGTCGAACAAAAGCCATTCTC
GATAAATATCACATTAAAGACGACGGAATGATTGCCCGTCAATTGCAG
GACAGGGATTATTATGATGCCGATTATATTATCGCAATGGATCAGATG
AATGTCCGGGACGCAAAAGATATGGCACCAGCTGGGTTAGAAAATAAG
GTTCATGGAATCTTTGAAGCTACCCCAGGAAAAGAAAATTGCTATATC
GTTGACCCCTGGATCACTCACTGA
```

(SEQ ID NO: 24)
```
(35)
ATGAAAAAAGCTATTTTTGAAAAGGCGGGTCAAATGAAGATTGTTGAT
GTTGACCGTCCAACAATTGAAAAGCCTGATGACGTAATTATTAAGGTA
GTGCGGACCTGTGTTTGTGGTTCTGACCTATGGAACTTCCGAGGAATT
AATCCGGTTGAAAAAGATTCTGAAAACTCTGGCCATGAAGCAATTGGA
ATTGTTGAAGAAGTTGGTGAAGATATCACTACTGTCAAACCTGGGGAC
TTTGTGATTGCTCCATTTACTCATGGATGTGGGCACTGTGCTGCTTGT
CGCGCGGGCTTCGATGGTTCTTGCCAAAGTCACAACGATAACTTTAGC
TCTGGTGTGCAAGCTCAATACGTTCGGTTCCAACACGGTCAATGGGCG
CTTGTTAAAGTTCCGGGCAAGCCAAGTGACTACAGTGAAGGAATGCTT
AAGTCCCTCTTAACCCTTGCTGATGTTATGGCTACTGGTTACCACGCT
GCACGAGTTGCTAACGTTAGTGATGGTGATACAGTTGTTGTAATGGGT
GACGGTGCTGTTGGCCTTTGTGCGATTATTGCTGCTAAGATGCGGGGC
GCTAAGAAGATCATTTCTACTAGTCGCCATGCTGACCGTCAAGCCCTT
GCTAAGGAATTTGGTGCTACTGACAATGTTGCTGAACGTAGTGACGAA
GCGGTTCAAAAGATCATGGAACTCACTAACGGTGCCGGTGCTGATGCT
GTCCTTGAATGCGTTGGTACTGAACAATCAACTGATACTGCCATGAAA
GTTGGCCGTCCAGGTACCATCGTTGGTCGGGTTGGCTTACCTCATACC
CCAAAGATGGACATGACGGTGCTATTCTACAACAACACTATTGTCGGC
GGTGGTCCAGCATCAGTAACCACTTACGACAAGGACGTATTGTTGAAG
GCTGTTCTTGATGGTGACATTAACCCTGGTAAGGTCTTTACTAAGAGC
TTCGACCTTGACCAAATTCAAGAAGCTTATGAAGCAATGGATAAGCGT
GAAGCAATCAAGTCTTACATTATTATGGATGGCTTTGAACGCGATTAA
```

(SEQ ID NO: 26)
```
(36)
ATGGGTCGTTTAGATAATAAAGTTGCAATTATTACTGGTGGTTCTAAA
GGAATTGGAGCTGCTGTCGCAAAAAAGTTTATCGAAGAAGGCGCAAAG
GTTGTTTTAACCGCTCGGAAGATGGATGAGGGACAAAAAGTCGCTGAC
CAACTAGGTGACAATGCGATCTTTATCCAACAAGACGTTGCTCGGAAA
GGAGACTGGGACCGGGTAATCCGCCAAACTGTCCAAGTCTTTGGGAAG
CTCAATATTGTGGTTAACAATGCGGGAATTGCCGAATACGCCGATGTT
GAGAAGACGGACGCTGAAATTTGGGATAAAACAATTGCCGTTAACCTT
ACCGGTACGATGTGGGGAACTAAGCTCGGTATTGAAGCAATGAAGAAC
AACGGGGAAAAGAATTCAATCATCAATATGTCATCCATTGAAGGACTA
ATTGGTGATCCTGATCTCTTTGCATACAATGCTTCTAAGGGTGGTGTC
CGCCTCTTAACTAAGTCCGCTGCGCTTGATTGTGCCCGGAAAGGCTAT
GACATCCGTGTAAATACAATTCATCCTGGTTATATCTCAACTCCACTA
GTTGATAATTTGGTCAAGGATGATCCAAAAGCAGAAGGACACCTAGAA
AGCCTTCATCCCCTTGGCCGTCTTGGAAAGCCAGAAGAGATTGCTAAC
CTCGCTTTATACCTTGCTTCAGATGAATCAAGCTTTAGTACTGGTTCG
GAATTTGTCGCTGATGGTGGCTATACGGCTCAATAA
```

Also, it is preferable that the lactic acid bacterium of the invention is one having a glycerol-degrading enzyme depicted in the following amino acid sequence (21) or (22) (corresponding to SEQ ID NO: 27 or 29, respectively) or an amino acid sequence having deletion, substitution or addition of one or more amino acids in the amino acid sequence (21) or (22). This glycerol-degrading enzyme is an alcohol dehydrogenase (ADH (8) in FIG. 1) and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping glycerol-degrading activity. Examples of such an amino acid sequence include those exhibiting homology of 80% or more.

(SEQ ID NO: 27)
```
(21)
MTNVPTVKLNNGVEMPTLGFEVFQVPDLSQ
AEQAVTDALEVGYRLIDTAAAYQNEEAVGK
AIKNSSVNREDVFVTSKLWVSDFNYKRAKA
GIDASLQKLGLDYMDLYLLHQPYGDTMGAW
RALQEAQKEGKIRAIGVSNFYADQLKDLEL
TMPVKPAVNQIEVNPWYQQDQEVKFAQSED
IRVEAWAPFAEGKHDIFTNEIIAEIAAKYG
KSNGQVILRWLLQRGITVIPKSVHKNRMEE
NIDVFDFELSNDDMKKIASLNKKESQFFDH
RDPVTIEQIFGSSLKMVQDDEK
```

(SEQ ID NO: 29)
```
(22)
MILDETITLNSGVKIPKFALGTWMIDDDQA
AEAVRNAIKMGYRHIDTAQAYDNERGVGEG
VRTAGIDRDKIFVTSKIAAEHKDYDVTKKS
IDETLEKMGLDYIDMMLIHSPQPWKEVNQS
DNRYLEGNLAAWRAMEDAVNEGKIRTIGVS
NFKKADLENIIKNSDTVPAVDQVLAHIGHT
PFNLLSFTHEHDIAVEAYSPVAHGAALDNP
VIEKMAKKYNVSVPQLCIRYDWQIGMIVLP
KTTNPEHMKENTEIDFEISEADMDLLRRVK
PLDYGDFDIYPVYGGKM
```

It is also possible to obtain a lactic acid bacterium with high glycerol-degrading properties by incorporating the following nucleotide sequence (37) or (38) (corresponding to SED ID NO: 28 or 30, respectively) encoding the glycerol-degrading enzyme (21) or (22), respectively into other lactic acid bacterium or the like by a genetic engineering technique. The invention also includes a nucleotide sequence having homology of 80% or more with the nucleotide sequence (37) or (38) and encoding a protein having glycerol-degrading activity; and a nucleotide sequence for achieving hybridization with the nucleotide sequence (37) or (38) under a stringent condition and encoding a protein having glycerol-degrading activity.

(SEQ ID NO: 28)
```
(37)
ATGACAAATGTACCAACAGTAAAATTAAATAACGGAGTAGAAATGCCAACCCTTGGATTT
GAAGTATTCCAAGTTCCAGACTTAAGCCAAGCTGAACAAGCAGTTACCGATGCTCTTGAA
GTCGGCTATCGTTTAATCGATACTGCTGCTGCTTACCAAAATGAAGAAGCAGTTGGAAAG
GCAATTAAGAATAGTAGTGTAAACCGTGAAGATGTCTTTGTAACTTCTAAGTTATGGGTG
TCTGATTTTAACTATAAGCGGGCTAAAGCAGGGATTGACGCTTCACTGCAAAAACTTGGC
CTTGATTACATGGATCTTTACCTTCTCCATCAACCATATGGCGATACAATGGGGGCTTGG
CGAGCATTACAAGAAGCACAGAAAGAAGGTAAGATTCGCGCAATCGGTGTATCGAACTTC
TACGCTGATCAACTAAAGGATCTTGAATTAACAATGCCTGTTAAGCCAGCGGTCAACCAA
ATTGAAGTTAACCCTTGGTACCAGCAAGATCAAGAGGTTAAGTTTGCGCAAAGTGAAGAT
ATTCGTGTTGAAGCATGGGCACCATTTGCGGAAGGTAAGCATGATATTTTTACCAACGAA
ATAATTGCGGAAATTGCTGCCAAGTATGGCAAGAGCAATGGTCAAGTAATTCTTCGCTGG
CTTTTACAACGGGGTATTACTGTCATTCCAAAGTCAGTCCACAAGAACCGGATGGAAGAA
AATATCGATGTCTTTGATTTTGAACTTTCCAATGATGATATGAAAAAGATAGCTAGTCTT
AACAAGAAGGAAAGCCAATTCTTTGACCACCGTGATCCGGTTACGATTGAACAAATCTTT
GGCTCCAGCTTAAAGATGGTTCAAGATGACGAAAAATAA
```

(SEQ ID NO: 30)
(38)
```
ATGATTTTAGATGAGACAATTACTCTTAATAGTGGTGTGAAAATTCCAAAGTTTGCATTA
GGAACCTGGATGATTGATGATGACCAAGCAGCCGAAGCAGTTCGGAATGCGATTAAGATG
GGATATCGGCACATCGATACAGCTCAGGCTTATGATAATGAGCGGGGAGTCGGTGAAGGT
GTACGAACAGCCGGTATTGATCGGGATAAAATCTTTGTTACTTCAAAGATCGCTGCTGAA
CACAAAGATTATGATGTAACTAAAAAGTCGATTGACGAGACTCTTGAAAAGATGGGTCTT
GATTATATCGACATGATGCTTATTCATAGTCCTCAACCATGGAAAGAAGTAAATCAATCT
GATAATCGTTACCTTGAAGGAAATCTCGCTGCTTGGCGAGCCATGGAAGATGCCGTTAAC
GAAGGTAAGATTCGAACAATTGGCGTTTCTAATTTCAAAAAAGCCGATCTTGAAAATATT
ATTAAGAATAGCGATACCGTTCCCGCTGTTGATCAAGTTTTAGCTCATATTGGTCATACT
CCATTCAATCTTTTATCATTTACTCATGAACATGACATTGCGGTTGAAGCATATTCACCA
GTTGCTCACGGCGCTGCTTTAGACAACCCCGTAATTGAAAAGATGGCTAAAAAGTACAAC
GTTTCAGTCCCACAATTGTGCATTCGGTATGATTGGCAAATAGGAATGATCGTCTTACCA
AAGACTACTAATCCAGAACACATGAAGGAAAACACTGAATTGATTTTGAAATTTCTGAA
GCTGATATGGACCTATTGCGGCGAGTAAAGCCATTAGACTATGGCGATTTTGATATCTAC
CCTGTTTACGGTGGAAAAATGTAA
```

Also, it is preferable that the lactic acid bacterium of the invention is one having an aldehyde dehydrogenase depicted in any of the following amino acid sequences (23) to (25) (corresponding to SEQ ID NO: 31, 33 and 35, respectively) or an amino acid sequence having deletion, substitution or addition of one or more amino acids in any of the amino acid sequences (23) to (25). This aldehyde dehydrogenase is an aldehyde dehydrogenase (9) in FIG. 1 and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping aldehyde dehydrogenase activity. Examples of such an amino acid sequence include those exhibiting homology of 80% or more.

(SEQ ID NO: 31)
(23)
```
MPANNKKQVEKKELTAEEKKQNAQKLVDDL
MTKSQAAFEKLRYYSQEQVDKICQAMALAA
EEHHMDLAVDAANETGRGVAEDKAIKNIYA
SEYIWNNIRHDKTVGIIEDNDEDQTIKIAD
PLGVIAGIVPVTNPTSTTIFKSIISAKTRN
TIIFSFHRQAMKSSIKTAKILQEAAEKAGA
PKNMIQWLPESTRENTTALLQHPNTATILA
TGGPSLVKAAYSSGNPALGVGPGNGPAYIE
KTANIERSVYDIVLSKTFDNGMICATENSV
VVDEEIYDKVKEEFQKWNCYFLKPNEIDKF
TDGFIDPDRHQVRGPIAGRSANAIADMCGI
KVPDNTKVIIAEYEGVGDKYPLSAEKLSPV
LTMYKATSHENAFDICAQLLHYGGEGHTAA
IHTLDDDLATKYGLEMRASRIIVNSPSGIG
GIGNIYNNMTPSLTLGTGSYGSNSISHNVT
DWDLLNIKTIAKRRENRQWVKIPPKVYFQR
NSLKELQDIPNINRAFIVTGPGMSKRGYVQ
RVIDQLRQRQNNTAFLVFDDVEEDPSTNTV
EKGVAMMNDFKPDTIIALGGGSPMDAAKAM
WMFYEHPETSWYGVMQKYLDIRKFRAYQIKK
PTKSQLIGIPTTSGTGSEVTPFAVITDSKT
HVKYPLADYALTPNIAIVDSQFVETVPAKT
TAWTGLDVLCHATESYVSVMATDYTRGWSL
QTIKGVMENLPKSVQGDKLARRKMHDFSTM
AGMAFGQAFLGINHSLAHKMGGAFGLPHGL
LIAIAMPQVIRFNAKRPQKLALWPHYETYH
ATKDYADIARFIGLKGNTDEELAEAYAKKV
IELAHECGVKLSLKDNGVTREEFDKAVDDL
ARLAYEDQCTTTNPVEPLVSQLKELLERCY
DGTGVEEK
```

(SEQ ID NO: 33)
(24)
```
MAYQSINPFTNQVEKTFENTTDEELEQTLT
TAHQLYLDWRKYNDLEERKRQILKLGQILR
ERRVEYATVMSKEMGKLISEAEGEVDLCAS
FCDYYAAHADEFLQPKIIATTSGRAKVLKQ
SLGILVAVEPWNFPFYQIARVFIPNFIAGN
PMILKDASNCPASAQAFNDAVKEAGAPAGS
LTNLFLSYDQVNKAIADKRVAGVCLTGSER
GGATVAKEAGANLKKSTLELGGNDAFIILD
DADWDLVEKVAPAARLYNAGQVCTSSKRFI
VLEKDYDRFLKMMKDAFSKVKMGDPLDPLT
TLAPLSSKKAKEKLQQQVATAVENGAKVYY
GNKPVDMEGQFFMPTILTDITPDNPIFDTE
MFGPVASVYKVSSEEEAIELANNSSYGLGN
TIFSNDSEHAERVAAKIETGMSWINAGWAS
LPELPFGGVKNSGYGRELSSYGIDEFTNKH
LIYEARQ
```

(SEQ ID NO: 35)
(25)
```
MQINDIESAVRKILAEELDNASSSSANVAA
TTDNGHRGIFTNVNDAIAAAKAAQEIYRDK
PIAVRQQVIDAIKEGFRPYIEKMAKDIKEE
TGMGTVEAKIAKLNNALYNTPGPEILEPVV
ENGDGGMVMYERLPYGVIGAVGPSTNPSET
VIANAIMMLAGGNTLYFGAHPGAKNVTRWT
IEKMNDFIADATGLHNLVVSIETPTIESVQ
QMMKHPDIAMLAVTGGPAVVHQAMTSGKKA
VGAGPGNPPAMVDATADIDLAAHNIITSAS
FDNDILCTAEKEVVAESSIKDELIRKMQDE
GAFVVNREQADKLADMCIQENGAPDRKFVG
KDATYILDQANIPYTGHPVEIICELPKEHP
LVMTEMLMPILPVVSCPTFDDVLKTAVEVE
KGNHHTATIHSNNLKHINNAAHRMQCSIFV
VNGPSYVGTGVADNGAHSGASALTIATPTG
EGTCTARTFTRRVRLNSPQGFSVRNWY
```

It is also possible to obtain a lactic acid bacterium with high glycerol-degrading properties by incorporating the following nucleotide sequences (39) to (41) (corresponding to SED ID NO: 32, 34 and 36, respectively) encoding the aldehyde dehydrogenases (23) to (25), respectively into other lactic acid bacterium or the like by a genetic engineering technique. The invention also includes a nucleotide sequence having homology of 80% or more with any of the nucleotide sequences (39) to (41) and encoding a protein having aldehyde dehydrogenase activity; and a nucleotide sequence for achieving hybridization with any of the nucleotide sequences (39) to (41) under a stringent condition and encoding a protein having aldehyde dehydrogenase activity.

(SEQ ID NO: 32)
(39)
```
ATGCCTGCTAACAACAAGAAACAAGTTGAAAAGAAAGAATTAACTGCTGAAGAAAAAAG
CAAAACGCCCAAAAGCTAGTTGACGATTTAATGACTAAGAGTCAAGCTGCTTTTGAAAAG
TTACGTTACTATTCACAAGAACAAGTTGACAAGATTTGTCAGGCAATGGCTCTCGCTGCC
GAAGAACACCACATGGACTTAGCTGTTGATGCTGCTAACGAAACTGGTCGTGGGGTTGCT
GAAGATAAGGCTATCAAGAACATCTACGCAAGTGAATACATTTGGAACAACATCCGTCAC
GATAAGACTGTTGGTATTATCGAAGACAATGATGAAGACCAAACTATCAAAATTGCTGAT
CCCACTTGGTGTCATTGCCGGAATTGTTCCAGTTACTAACCCTACTTCAACAACGATCTTC
AAATCAATCATTAGTGCTAAGACACGGAATACAATCATCTTTTCTTTCCACCGTCAAGCA
ATGAAGTCATCTATCAAGACTGCAAAGATTCTCCAAGAAGCTGCTGAAAAAGCCGGTGCG
CCAAAGAACATGATTCAATGGCTCCCTGAAAGTACCCGCGAAAACACTACCGCATTACTC
CAACACCCTAATACTGCTACTATTTTAGCAACCGGTGGTCCTTCATTAGTTAAGGCTGCC
TACAGTTCTGGTAACCCTGCTCTTGGTGTTGGTCCTGGTAACGGTCCTGCTTACATCGAA
AAAACTGCCAACATCGAACGTTCTGTTTACGACATCGTTCTTTCTAAGACATTCGATAAC
GGTATGATTTGTGCCACTGAAAACTCAGTTGTTGTTGATGAAGAAATCTACGACAAGGTT
AAAGAAGAATTCCAAAAGTGGAACTGTTACTTCTTGAAGCCAAACGAAATTGATAAATTT
ACTGATGGCTTTATTGACCCAGATCGTCATCAAGTTCGTGGTCCAATCGCTGGTCGTTCA
GCTAATGCTATTGCTGACATGTGTGGTATTAAAGTACCTGACAACACTAAGGTTATCATT
GCTGAATACGAAGGTGTTGGTGACAAGTACCCACTTTCAGCTGAAAAGCTTTCACCAGTA
TTAACAATGTACAAGGCAACCTCTCACGAAATGCCTTTGATATCTGTGCTCAATTATTA
CACTACGGTGGTGAAGGTCACACTGCTGCTATTCACACCCTTGATGATGATTTAGCTACT
AAGTACGGTCTTGAAATGCGTGCTTCACGGATCATTGTTAACTCCCCATCTGGTATTGGT
GGTATTGGTAACATCTACAACAACATGACTCCATCCCTTACTTTAGGTACTGGTTCATAC
GGTAGTAACTCAATTTCTCACAACGTTACTGATTGGGACCTCTTAAACATCAAAACAATT
GCAAAGCGGCGTGAAAACCGTCAATGGGTTAAGATTCCCCCAAAAGTATACTTTCAACGC
AACTCACTAAAAGAATTGCAAGATATTCCAAACATTAACCGGGCATTCATCGTTACTGGT
CCTGGAATGAGCAAGCGTGGTTACGTTCAACGTGTTATCGATCAATTGCGTCAACGCCAA
AACAACACTGCTTTCTTAGTATTTGATGACGTTGAAGAAGATCCATCAACAAACACTGTT
GAAAAAGGTGTTGCCATGATGAATGACTTCAAACCTGATACAATTATTGCTCTTGGTGGT
GGTTCACCAATGGATGCTGCTAAGGCTATGTGGATGTTCTATGAGCACCCAGAAACTTCA
TGGTATGGGGTTATGCAAAAGTACCTTGATATTCGGAAGCGTGCTTACCAAATCAAGAAG
CCTACTAAGTCTCAACTTATTGGTATCCCTACTACATCAGGTACTGGTTCAGAAGTTACT
CCATTTGCGGTTATTACCGATTCAAAAACTCATGTTAAGTACCCACTTGCTGACTACGCC
TTAACACCAAACATTGCAATCGTTGACTCACAATTCGTTGAAACTGTTCCAGCAAAAACT
ACTGCTTGGACTGGACTAGATGTTTTATGTCACGCTACTGAATCATATGTTTCTGTTATG
GCAACTGACTACACTCGTGGTTGGTCACTACAAACCATCAAGGGTGTTATGGAAAACCTT
CCTAAGTCAGTTCAAGGTGATAAGTTAGCTCGTCGTAAGATGCACGACTTCTCAACAATG
GCCGGGATGGCATTTGGTCAAGCCTTCTTAGGAATTAACCACTCCCTTGCCCACAAGATG
GGTGGAGCATTCGGTCTTCCTCACGGTTTGCTTATCGCTATTGCAATGCCACAAGTAATT
CGCTTTAACGCAAAACGTCCACAAAAGCTTGCTCTCTGGCCTCACTATGAGACTTACCAT
GCAACTAAGGACTACGCTGACATTGCACGGTTCATTGGTTTGAAAGGCAACACTGATGAA
GAATTAGCTGAAGCATATGCTAAGAAAGTTATCGAACTTGCTCACGAATGTGGTGTTAAG
CTTAGTCTTAAGGACAATGGTGTTACACGTGAAGAATTTGATAAGGCGGTTGACGATCTT
GCTCGCTTAGCTTACGAAGATCAATGTACTACTACTAACCCAGTTGAACCACTTGTTAGC
CAACTCAAGGAATTACTTGAACGTTGCTACGATGGTACTGGCGTTGAAGAAAAATAA
```

(SEQ ID NO: 34)
(40)
```
ATGGCATATCAAAGTATCAATCCATTTACGAACCAAGTAGAAAAAACGTTTGAAAATACA
ACTGATGAAGAATTAGAACAAACATTAACTACGGCGCATCAATTATATTTAGATTGGCGG
AAGTATAATGACCTTGAAGAACGGAAACGGCAAATTTTAAAGTTAGGTCAAATATTACGT
GAACGGCGTGTTGAATATGCGACAGTTATGAGTAAGGAAATGGGAAAATTAATTAGCGAA
GCAGAAGGCGAGGTTGACCTTTGTGCTTCTTTCTGTGATTATTATGCAGCCCATGCAGAT
GAATTTCTGCAACCAAAAATTATTGCGACAACGAGTGGACGCGCCAAAGTTTTGAAGCAA
TCATTAGGAATTTTAGTTGCAGTTGAACCTTGGAATTTCCCATTCTATCAAATTGCCCGG
GTATTTATTCCCAACTTTATTGCAGGAAACCCCATGATCTTGAAGGATGCGTCGAATTGT
CCAGCATCCGCCCAAGCATTTAACGATGCCGTTAAGGAAGCTGGTGCGCCAGCCGGCAGT
TTAACTAATTTATTCCTTTCATATGACCAAGTAAATAAGGCAATTGCTGATAAGCGGGTA
GCCGGCGTTTGTCTTACTGGTTCTGAACGTGGTGGTGCAACCGTTGCTAAAGAGGCTGGT
GCTAATTTGAAGAAGAGCACTTTGGAACTTGGTGGTAATGATGCCTTTATTATCTTAGAC
GATGCAGATTGGGATCTTGTCGAAAAAGTTGCCCCGGCAGCCCGTCTGTATAATGCTGGA
CAAGTATGTACATCATCAAAACGTTTTATTGTCCTTGAAAAGGATTATGATCGTTCTTA
AAGATGATGAAAGATGCGTTCTCGAAAGTTAAAATGGGTGATCCCCTTGATCCATTAACA
ACTCTGGCACCATTATCATCTAAGAAAGCAAAAGAAAAGCTCCAACAGCAAGTCGCAACA
GCAGTAGAAAATGGGGCCAAAGTTTACTATGGTAATAAGCCGGTTGACATGGAAGGTCAA
TTCTTTATGCCAACGATCTTAACTGATATCACTCCAGATAACCCAATATTTGATACGGAA
ATGTTTGGGCCAGTGGCTTCGGTTTATAAGGTTAGTTCCGAAGAGGAAGCAATCGAACTG
GCTAATAATTCAAGCTATGGGTTAGGAAACACTATCTTTAGCAATGATTCCGAACATGCG
GAACGAGTAGCAGCGAAGATCGAACTGGAATGAGTTGGATTAATGCCGGCTGGGCTTCA
TTACCAGAATTACCATTTGGTGGTGTTAAGAATTCAGGTTACGGTCGTGAACTCAGCAGT
TACGGAATTGATGAATTTACTAACAAACATCTAATTTACGAAGCACGACAATAA
```

(SEQ ID NO: 36)
(41)
```
ATGCAGATTAATGATATTGAAGTGCTGTACGCAAAATTCTTGCCGAAGAACTAGATAAT
GCCAGCTCTTCAAGTGCAAACGTTGCAGCTACTACTGATAATGGTCATCGCGGAATTTTC
ACTAATGTCAATGATGCAATTGCTGCTGCAAAAGCTGCTCAAGAAATATATCGGGATAAG
CCAATTGCTGTTCGCCAACAAGTGATTGATGCCATTAAGGAAGGATTCCGCCCATATATT
GAAAAAATGGCTAAAGATATCAAAGAAGAAACAGGAATGGGAACAGTAGAGGCCAAAATT
GCTAAGTTAAACAATGCCTTGTACAACACTCCTGGTCCCGAGATTCTTGAACCAGTTGTA
```

```
-continued
GAAAACGGTGACGGTGGGATGGTTATGTATGAACGGTTACCATATGGTGTTATTGGTGCG
GTTGGCCCAAGTACAAACCCTTCAGAAACTGTAATTGCTAATGCGATCATGATGGTTGCC
GGTGGTAATACTCTTTACTTTGGTGCTCACCCTGGCGCAAAGAATGTTACTCGCTGGACA
ATTGAAAAGATGAACGATTTTATTGCAGATGCAACAGGCCTTCATAATTTAGTTGTAAGT
ATTGAAACACCAACAATTGAATCAGTTCAACAAATGATGAAGCACCCCGACATTGCAATG
TTAGCAGTAACTGGTGGCCCAGCTGTTGTTCACCAAGCAATGACCAGTGGTAAGAAAGCG
GTTGGTGCTGGTCCTGGTAATCCTCCTGCAATGGTTGATGCTACTGCTGATATTGATTTA
GCTGCTCATAATATCATTACATCTGCTTCATTTGATAATGATATTTTATGTACTGCTGAA
AAGGAAGTAGTTGCAGAAAGTAGCATTAAAGATGAATTAATTCGTAAGATGCAAGATGAA
GGTGCCTTTGTAGTTAACCGTGAACAAGCCGATAAATTAGCTGATATGTGTATCCAAGAA
AATGGTGCTCCTGATCGTAAATTTGTTGGTAAGGATGCAACTTATATCTTAGACCAAGCT
AATATTCCTTACACAGGCCACCCAGTTGAAATTATTTGTGAACTTCCTAAGGAACATCCA
TTAGTAATGACTGAAATGTTAATGCCAATTTTACCAGTTGTTTCTTGTCCAACATTTGAT
GATGTTTTGAAGACTGCTGTTGAAGTTGAAAAAGGTAACCATCACACAGCTACTATTCAT
TCCAATAACCTTAAGCATATTAATAATGCTGCTCACCGGATGCAATGTTCAATCTTTGTT
GTTAATGGCCCATCCTATGTTGGTACAGGTGTTGCAGATAATGGAGCTCACTCAGGTGCT
TCAGCATTAACAATTGCTACGCCAACTGGTGAAGGAACATGTACTGCACGAACATTTACT
CGTCGGGTTCGTTTGAACTCACCACAAGGATTCTCAGTACGTAACTGGTATTAA
```

Also, it is preferable that the lactic acid bacterium of the invention is one having a glycerate kinase depicted in the following amino acid sequence (26) (corresponding to SEQ ID NO: 37) or an amino acid sequence having deletion, substitution or addition of one or more amino acids in the amino acid sequence (26). This glycerate kinase is Glycerate kinase (10) in FIG. 1 and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping glycerate kinase activity. Examples of such an amino acid sequence include those exhibiting homology of 80% or more.

```
                                           (SEQ ID NO: 37)
(26)
MKFVIAPDSFKGGLTAKEAANVMAEGIKRV
FPNAEYALVPMADGGEGTVQSLVDATNGQK
MIAKVHNPLNKLVNAEYGILGDGETAVIEM
```

```
-continued
AAASGLQFVNKETANPLITTTYGTGELIKD
ALDHNIKKIIIGIGGSATVDGGAGMAQALG
ARLLDADNHEIGLGGGELASLEQVDFGGLD
PRLKNVDIQIASDVTNPLTGKNGAAPVFGP
QKGADEEMVNILDKNLHHYARKIVAAGGPD
VEQTAGAGAAGGLGAGLIAFTGATMKRGVE
LVIEATQLQKKAVGADYVFTGEGGIDFQTK
FGKTPYGVAKATKEVAPTAPVIVLAGNIGK
GVNDLYSSTAIDAIFATPEGAKPLKTALAD
APIDIAQTAENVARLIKVSHVSN
```

It is also possible to obtain a lactic acid bacterium with high glycerol-degrading properties by incorporating the following nucleotide sequence (42) (corresponding to SED ID NO: 38) encoding the glycerate kinase (26) into other lactic acid bacterium or the like by a genetic engineering technique. The invention also includes a nucleotide sequence having homology of 80% or more with the nucleotide sequence (42) and encoding a protein having glycerate kinase activity; and a nucleotide sequence for achieving hybridization with the nucleotide sequence (42) under a stringent condition and encoding a protein having glycerate kinase activity.

```
                                           (SEQ ID NO: 38)
(42)
ATGAAATTTGTAATTGCTCCAGATTCATTTAAAGGCGGATTAACAGCAAAAGAAGCAGCA
AATGTGATGGCAGAAGGAATCAAAAGAGTGTTTCCGAATGCCGAGTATGCTTTAGTTCCA
ATGGCTGATGGAGGAGAGGGGACTGTTCAATCCTTAGTTGATGCGACTAACGGTCAAAAA
ATGATTGCTAAAGTCCACAACCCATTAAATAAATTAGTTAATGCTGAGTACGGAATATTA
GGTGATGGGGAAACGGCAGTGATTGAGATGGCGGCGGCAAGTGGCCTTCAATTTGTTAAT
AAGGAGACTGCGAACCCGCTTATTACAACTACATATGGTACCGGCGAGTTAATTAAGGAT
GCTCTTGACCATAACATTAAAAAAATAATTATTGGAATTGGTGGAAGTGCAACCGTTGAT
GGCGGAGCGGGGATGGCCCAAGCACTTGGAGCACGTTTATTGGATGCTGATAATCATGAA
ATTGGTTTAGGCGGTGGTGAGTTAGCAAGTTTAGAGCAAGTAGATTTTGGAGGATTAGAT
CCTCGCTTAAAAAATGTAGATATTCAGATTGCATCAGACGTAACCAACCCATTAACAGGA
AAAAATGGGGCAGCCCCAGTATTTGGCCCGCAAAAAGGAGCTGATGAAGAAATGGTGAAC
ATCTTGGACAAAAATCTTCATCATTATGCCCGAAAAATAGTTGCAGCTGGTGGGCCAGAC
GTTGAACAAACGGCAGGTGCAGGGGCAGCCGGTGGTTTAGGAGCCGGGTTGATAGCATTT
ACCGGTGCGACAATGAAGCGAGGAGTAGAATTAGTGATTGAAGCAACTCAACTACAAAAA
AAGGCAGTTGGCGCTGATTATGTTTTTACTGGTGAAGGAGGAATTGATTTCCAGACTAAA
TTTGGTAAAACGCCATATGGAGTCGCTAAGGCAACTAAAGAGGTGGCTCCAACTGCTCCG
GTAATTGTGTTGGCTGGAAATATTGGTAAAGGCGTAAATGATCTATATTCATCCACGGCC
ATTGATGCAATTTTTGCAACTCCTGAAGGGGCTAAACCATTAAAAACAGCATTAGCAGAT
GCACCTATTGATATTGCTCAAACAGCGGAAAACGTTGCACGTTTAATTAAAGTGAGTCAT
GTTAGTAATTAA
```

Also, it is preferable that the lactic acid bacterium of the invention is one having a glycerol kinase depicted in the following amino acid sequence (27) (corresponding to SEQ ID NO: 39) or an amino acid sequence having deletion, substitution or addition of one or more amino acids in the amino acid sequence (27). This glycerol kinase is GK (5) in FIG. 1 and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping glycerol kinase activity. Examples of such an amino acid sequence include those exhibiting homology of 80% or more.

```
                                            (SEQ ID NO: 39)
(27)
LSEQQYIMAIDQGTTSSRAIIFDHDGNKVA
ISQQEFPQYFPQPGWVEHDPLEIWDSVQSV
ISNVMIKSQIKPYKIAAIGITNQRETTVIW
DRHTGKPIYNAIVWQSKQTSDIAEQLIKDG
YKDMIHQKTGLVIDSYFAATKIKWILDHVP
GAREKAAKGDLMFGTIDTWLLWNLSGRRVH
ATDVTNASRTMLFNIHTLDWDQDILDLLDI
PQSLLPVVKPSSAIYGYTGDYHFYGVQIPI
AGIAGDQQAALFGQAAYDKGSIKNTYGTGA
FIVMNTGLKPTLSDNGLLTTIAYGLDGQTH
YALEGSIFVAGSAVQWLRDGLKMFDKASES
EQMAVDAKTTGGVYVVPAFTGLGAPYWDQE
VRGAMFGLTRGTERGHIIRATLEAIAYQTK
DVVDTMVKDTQLPLTALTVNGGASRNNFMM
QFQADILQTPIKRAAMEETTALGAAFLAGL
AVDFWEDQDELRKLSRIGDQFDPQMDPQKA
ADLYRGWQRAIAAAQFYGKD
```

It is also possible to obtain a lactic acid bacterium with high glycerol-degrading properties by incorporating the following nucleotide sequence (43) (corresponding to SED ID NO: 40) encoding the glycerol kinase (27) into other lactic acid bacterium or the like by a genetic engineering technique. The invention also includes a nucleotide sequence having homology of 80% or more with the nucleotide sequence (43) and encoding a protein having glycerol kinase activity; and a nucleotide sequence for achieving hybridization with the nucleotide sequence (43) under a stringent condition and encoding a protein having glycerol kinase activity.

```
                                            (SEQ ID NO: 40)
(43)
TTGAGTGAACAACAATATATCATGGCGATTGACCAGGGAACGACGAGCTCACGGGCGATT
ATCTTTGACCATGACGGAAATAAGGTTGCGATCAGTCAGCAGGAATTTCCCCAATACTTC
CCGCAGCCGGGGTGGGTTGAACATGATCCTCTAGAGATTTGGGATAGCGTTCAATCAGTG
ATTTCAAATGTAATGATTAAGTCCCAGATCAAGCCCTATAAGATTGCGGCAATTGGGATT
ACTAACCAACGGGAGACGACGGTTATTTGGGATCGCCATACCGGTAAGCCGATTTATAAC
GCAATTGTCTGGCAATCGAAGCAAACGAGCGACATCGCCGAACAATTGATTAAAGATGGT
TATAAGGATATGATCCACCAGAAGACTGGCTTGGTGATTGATTCGTATTTCGCGGCCACT
AAGATCAAGTGGATCCTTGACCATGTTCCTGGTGCCCGGGAAAAAGCAGCAAAGGGAGAC
TTGATGTTTGGGACTATCGATACTTGGTTACTATGGAATTTATCGGGACGGCGGGTCCAC
GCAACGGATGTGACCAATGCCAGCCGGACGATGCTTTTTAATATCCATACCCTCGACTGG
GATCAAGATATCCTTGACCTGCTTGATATTCCCCAGTCGCTTTTGCCAGTAGTAAAGCCA
AGTTCAGCCATTTACGGTTATACTGGCGACTACCACTTCTATGGGGTGCAGATTCCAATT
GCCGGGATTGCAGGTGACCAACAAGCAGCCCTCTTTGGTCAAGCAGCCTATGATAAAGGT
TCAATCAAGAACACCTATGGGACTGGAGCCTTCATCGTCATGAATACGGGACTAAAACCC
ACGCTTTCGGATAACGGCTTGTTGACGACGATTGCGTATGGCCTGGACGGGCAAACTCAT
TACGCGCTTGAAGGAAGTATCTTTGTGGCCGGTTCTGCCGTTCAATGGTTGCGGGATGGT
CTCAAGATGTTTGATAAGGCAAGCGAGTCCGAACAAATGGCTGTCGATGCCAAGACAACT
GGCGGCGTTTATGTCGTCCCCGCCTTTACAGGATTAGGCGCACCGTACTGGGATCAAGAA
GTGCGGGCGCAATGTTTGGCCTTACCCGTGGAACTGAACGGGGACATATCATCCGTGCA
ACTTTGGAAGCCATTGCCTACCAGACCAAAGATGTTGTCGATACGATGGTCAAGGACACC
CAATTACCACTAACAGCACTAACGGTTAACGGGGGCGCTTCACGGAACAACTTCATGATG
CAGTTCCAGGCCGATATCTTACAAACGCCAATCAAGCGGGCAGCAATGGAAGAGACAACC
GCGCTGGGAGCAGCCTTTCTCGCTGGATTGGCCGTTGATTTCTGGGAAGACCAGGATGAG
TTACGGAAGCTATCACGGATTGGCGACCAGTTTGATCCACAAATGGATCCGCAAAAGGCA
GCTGACTTGTATCGGGGATGGCAACGGGCCATTGCAGCTGCGCAGTTTTATGGCAAAGAT
TAA
```

Also, it is preferable that the lactic acid bacterium of the invention is one having a glycerol-3-phosphate dehydrogenase depicted in the following amino acid sequence (28) (corresponding to SEQ ID NO: 41) or an amino acid sequence having deletion, substitution or addition of one or more amino acids in the amino acid sequence (28). This glycerol-3-phosphate dehydrogenase is GPD (6) in FIG. 1 and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping glycerol-3-phosphate dehydrogenase activity. Examples of such an amino acid sequence include those exhibiting homology of 80% or more.

```
                                            (SEQ ID NO: 41)
(28)
MAEKIAVLGAGSWGSVLANMLTENGHDVTL
WSRNEEQVKQLNTEHTNPRYMKDFVYSTNL
TATTDMKKAVKGASVVLIVIPTKGLREVAK
QLNAILTELHQKPLVIHATKGLEQNTYKRP
SEMLSEDISPENRQAIVVLSGPSHAEDVAI
KDMTAVTAACEDLASAKKAQKLFSNSYFRV
YTNDDVIGAEFGAALKNIIAIGAGAIQGLG
YHDNARAALITRGLAEIRRLGVAFGANPMT
FIGLSGVGDLVVTATSKNSRNWRAGYQLGQ
GKKLQDVIDNMGMVIEGVYTTKAAYELSRK
RQVQMPITEALYRVLYEGEDIKTAISQLMD
RDLTSENE
```

It is also possible to obtain a lactic acid bacterium with high glycerol-degrading properties by incorporating the following nucleotide sequence (44) (corresponding to SED ID NO: 42) encoding the glycerol-3-phosphate dehydrogenase (28) into other lactic acid bacterium or the like by a genetic engineering technique. The invention also includes a nucleotide sequence having homology of 80% or more with the nucleotide sequence (44) and encoding a protein having glycerol-3-phosphate dehydrogenase activity; and a nucleotide sequence for achieving hybridization with the nucleotide sequence (44) under a stringent condition and encoding a protein having glycerol-3-phosphate dehydrogenase activity.

```
                                                   (SEQ ID NO: 42)
(44)
ATGGCAGAAAAAATTGCTGTTTTAGGTGCTGGTTCGTGGGGCAGTGTTTTAGCAAACATG
CTTACAGAAAATGGCCACGATGTAACATTATGGTCTCGTAATGAGGAACAAGTTAAGCAA
TTAAATACTGAACATACAAATCCTCGCTATATGAAAGATTTTGTTTATTCTACTAACTTA
ACAGCAACAACGGACATGAAAAAAGCTGTTAAGGGTGCCAGTGTGGTCCTGATTGTAATT
CCAACAAAGGGTCTTCGTGAAGTTGCTAAGCAATTAAATGCAATTTTGACTGAATTACAT
CAAAAACCGCTAGTTATTCACGCAACGAAAGGCTTAGAACAAAATACTTATAAGCGGCCA
TCGGAAATGCTTAGCGAAGATATTTCTCCTGAAAACCGTCAGGCAATTGTTGTTTATCA
GGTCCGAGTCATGCTGAAGATGTGGCGATTAAAGATATGACAGCTGTAACCGCAGCTTGT
GAGGACCTGGGCAGTGCTAAAAAGGCGCAGAAGTTATTTAGTAATTCTTATTTCCGTGTG
TACACTAATGACGATGTAATTGGTGCCGAATTTGGCGCAGCCTTAAAGAACATTATTGCA
ATTGGTGCTGGAGCTATTCAGGGACTTGGTTATCATGATAATGCTCGGGCAGCGTTAATT
ACTCGTGGACTTGCAGAAATTCGCCGATTGGGAGTTGCTTTTGGTGCCAACCCGATGACT
TTTATTGGTCTTTCTGGGGTTGGTGACCTTGTTGTTACTGCTACCAGTAAAAATTCTCGA
AATTGGCGTGCTGGCTATCAATTGGGGCAAGGAAAAAAGCTTCAAGATGTAATTGATAAT
ATGGGAATGGTTATCGAAGGTGTCTATACTACCAAAGCCGCTTATGAATTAAGTCGTAAA
CGACAAGTACAGATGCCAATTACCGAAGCTCTTTACCGTGTTTTGTATGAAGGCGAAGAT
ATTAAAACTGCAATTTCTCAATTAATGGACCGAGATCTTACTTCAGAAAACGAATAA
```

Also, it is preferable that the lactic acid bacterium of the invention is one having triosephosphate isomerase depicted in any of the following amino acid sequences (29) to (32) (corresponding to SEQ ID NO: 43, 45 and 47, respectively) or an amino acid sequence having deletion, substitution or addition of one or more amino acids in any of the amino acid sequences (29) to (31). This triosephosphate isomerase is Triosephosphate isomerase (15) in FIG. 1 and is able to efficiently metabolize glycerol produced by the action of the lipases of the invention. The "amino acid sequence having deletion, substitution or addition of one or more amino acids" as referred to herein means a sequence equivalent to the original sequence thereof and refers to a sequence still keeping triosephosphate isomerase activity. Examples of such an amino acid sequence include those exhibiting homology of 80% or more.

```
                                           (SEQ ID NO: 43)
(29)
MRKPFIAANWKMHKNVQESVEFVDAIKGKL
PDPQEVEVGIAAQAFALPSMVQAADDSGLK
IIAQNAAAEYSGAFTGEISLRGLADAGVSY
VMLGHIERRHLFHEDNELVNRKVLAALQMG
VTPIICTDETMVQKEVNGEIHYVFQQLMSV
LRGVSLDQIKNVVVSYEPSWAVGYGQHANP
VLAEEGCRQIRRTIADNYTYEIADKIRILY
GGSVNPDNIGMIMNKPDVDGVLIGRASLDV
DNFLRMVNYLKNDQEK (SEQ ID NO: 45)
(30)
MRKPFIIANWKMNKNVHESVAFVKAIKEKL
```

```
                                           -continued
PADKEIGIAAQAVSLYNMKKVASSSNLQII
AQNASAELEGPYTGEISMRSLADAGVTYVM
LGHLERRRLFNESNDSINQKVLAALNAGII
PIICTDEEMVQTEVNGQIHYVFRQLKSVLK
GVPANKLSQIVISYEPSWAVGSTHQANPDI
AEEGCQAIRQSLVEMYGNEIGEQVRILYGG
SVNPENIGQIMSKPNVDGALIGRASLEIES
FLQMINYIELASKQKLQVI (SEQ ID NO: 47)
(31)
MRVPIIAGNWKMHKDVQEAVSFIEKVKNQL
PPADQLETAIAAPTLCLVPMVKAAEESPLK
IMAENCYYKNEGAYTGETSPYALYQAGIHH
VILGHSERRTYFNETDELINKKVKAALVNG
LCPIVCCDDTMRRRVAGKKVHWVVSRILAD
LHGLTNDEICHVTVAYEPSWAIGTGESADP
EQAAEGCYLIRQTISDMYGDEVANNVRILY
GGSVTTSNINALMAKNDIDGVLVGAASLNP
ETFLQLVHH
```

It is also possible to obtain a lactic acid bacterium with high glycerol-degrading properties by incorporating the following nucleotide sequences (45) to (47) (corresponding to SED ID NO: 44, 46 and 48, respectively) encoding the triosephosphate isomerases (29) to (31), respectively into other lactic acid bacterium or the like by a genetic engineering technique. The invention also includes a nucleotide sequence having homology of 80% or more with any of the nucleotide sequences (45) to (47) and encoding a protein having triosephosphate isomerase activity; and a nucleotide sequence for achieving hybridization with any of the nucleotide sequences (45) to (47) under a stringent condition and encoding a protein having triosephosphate isomerase activity.

```
                                                   (SEQ ID NO: 44)
(45)
ATGCGCAAACCCTTTATTGCTGCTAATTGGAAGATGCATAAGAATGTCCAAGAATCGGTT
GAATTTGTGGATGCAATTAAAGGAAAGCTACCAGATCCGCAAGAAGTTGAAGTCGGAATT
GCAGCCCAAGCTTTTGCATTACCCAGTATGGTTCAAGCCGCTGATGATTCAGGATTAAAG
ATAATCGCGCAAAACGCGGCGGCTGAATATTCGGGAGCTTTCACTGGTGAAATTAGCTTA
CGAGGTTTAGCTGACGCCGGTGTTTCATATGTAATGTTAGGACATATTGAACGGCGCCAT
TTATTCCACGAGGATAATGAGTTGGTTAATCGGAAAGTGTTGGCAGCCCTTCAAATGGGA
GTTACCCCGATAATTTGTACGGATGAAACGATGGTCCAGAAAGAAGTTAATGGTGAAATT
CACTACGTTTTCCAGCAATTGATGAGCGTATTGAGGGGCGTTTCTCTTGATCAAATTAAA
AATGTAGTTGTTTCCTATGAACCAAGTTGGGCAGTTGGATATGGTCAGCATGCTAATCCA
GTTCTTGCTGAAGAAGGATGCCGTCAAATTCGGCGAACGATTGCTGATAACTACACTTAT
GAGATTGCTGATAAGATCAGGATTCTTTATGGGGGCAGTGTCAATCCAGATAATATCGGA
ATGATTATGAACAAGCCAGATGTAGATGGGGTATTAATCGGTCGGGCAAGTTTAGATGTT
GATAATTTTTTGCGAATGGTCAATTATTTAAAAAATGATCAAGAAAAATAA
```

(SEQ ID NO: 46)
(46)
```
ATGCGCAAACCGTTTATTATTGCGAACTGGAAAATGAATAAAAACGTTCATGAATCTGTT
GCGTTTGTTAAAGCAATTAAAGAAAAGCTCCCGGCAGATAAAGAAATTGGGATCGCCGCG
CAAGCAGTTTCGCTATATAACATGAAAAAAGTGGCGAGCTCTTCCAACTTACAAATTATT
GCTCAAAATGCATCTGCTGAGTTAGAGGGACCATATACTGGAGAAATTAGCATGCGAAGT
TTAGCAGATGCGGGCGTGACATACGTGATGCTAGGCCATTTAGAGCGCCGACGCCTTTTT
AACGAGAGTAATGATTCAATTAATCAAAAAGTTTTAGCGCCCTCAATGCTGGTATTATT
CCAATCATTTGTACGGATGAAGAGATGGTCCAAACAGAAGTTAACGGACAAATTCATTAT
GTATTTCGCCAACTAAAAAGCGTCCTTAAAGGGGTACCAGCTAATAAACTATCACAGATT
GTTATTTCGTATGAACCAAGTTGGGGCGTTGGGAGCACGCATCAAGCAAATCCAGACATT
GCGGAAGAGGGATGTCAGGCAATTCGTCAAAGCCTGGTTGAAATGTATGGTAATGAGATT
GGCGAGCAAGTCCGAATACTCTATGGTGGCAGCGTTAATCCCGAGAACATTGGTCAAATT
ATGAGTAAACCAAATGTTGATGGGGCGCTAATCGGTCGCGCAAGTCTCGAGATTGAAAGT
TTCTTACAAATGATTAATTATATCGAATTAGCGAGCAAGCAGAAGTTACAGGTAATTTAG
```

(SEQ ID NO: 48)
(47)
```
ATGAGAGTACCGATTATTGCTGGTAATTGGAAAATGCATAAGGATGTACAAGAAGCTGTC
TCTTTTATCGAAAAAGTAAAAAATCAGCTTCCGCCTGCCGACCAACTTGAAACAGCAATT
GCTGCTCCTACTCTTTGTTTAGTACCAATGGTTAAAGCAGCTGAAGAATCCCCGTTAAAA
ATAATGGCAGAAAACTGCTACTATAAGAATGAGGGAGCTTATACTGGTGAAACAAGTCCA
TATGCTTTATACCAAGCAGGAATCCATCATGTGATTTTAGGCCATTCTGAACGCCGAACT
TACTTTAATGAAACTGATGAATTAATTAATAAAAAAGTGAAGGCAGCATTAGTAAATGGG
TTATGTCCGATTGTTTGTTGTGATGATACTATGCGTCGACGAGTTGCTGGAAAGAAAGTT
CATTGGGTGGTGAGCCGAATTCTCGCTGACCTTCATGGATTGACCAATGACGAAATTTGT
CATGTTACGGTTGCTTATGAACCAAGTTGGGCGATTGGAACAGGCGAGAGTGCTGATCCA
GAACAAGCGGCGGAAGGTTGTTACCTTATTCGGCAAACGATTAGTGATATGTATGGCGAT
GAAGTTGCAAATAACGTTCGAATTCTCTATGGCGGAAGTGTGACAACTTCTAATATCAAT
GCACTAATGGCAAAAAATGATATTGATGGTGTTTTAGTCGGAGCGGCGAGCTTAAATCCA
GAAACATTTTTACAATTAGTTCACCATTAG
```

The above-described lactic acid bacteria of the invention can be obtained by subjecting a microorganism belonging to the species *Lactobacillus reuteri* to genetic analysis by the ordinary method. For example, with respect to many microorganisms belonging to the species *Lactobacillus reuteri*, it is possible to obtain the targeted lactic acid bacterium of the invention by examining whether or not there are nucleotide sequences having high homology with the following genes (13) to (15) (corresponding to SEQ ID NO: 2, 4 and 6, respectively) encoding the lipases (1) to (3), respectively.

(13)
```
ATGGTGAAATTGATGACAATACACGAATTAGCAAATAACCCAACGTTAAGCGGCCAAGTA
GGCTTGATTGAAAATATTGTTTATGGTGCGATGGATGGTGAGGCATTACATATGTCGATC
TTAGCACCGTGGACGCAACGTTTCCCGAAACAATATCAAACTGAACCTCGACCATTGATT
GTCTTTGTTCAAGGAAGCTCGTGGCGAACACCAAAAATGGGAGAAGAAATTCCACAACTG
GTTCAATTTGTTCGGGCCGGTTATATTGTAGCGACTGTTCAACACCGTAGTTCAATTGAT
AGCCACCCATTTCCTGCCTTTTTGCAAGATGTTAAGACTGCCATTCGTTTCTTACGGGCC
AATGCGCAAAAATATGCAATTGATCCGCAACAGGTTGCAATTTGGGGGACTTCCTCTGGA
GCCAATGCGGCAATGCTAGTCGGCTTAACGGGTGATGATCCGCGCTATAAAGTTGACCTT
TATCAAGACGAATCGGATGCAGTAGATGCTGTGGTTAGTTGTTTTGCCCCAATGGACGTG
GAGAAGACGTTTGAGTATGATGCTAATGTTCCAGGAAATAAGTTACTGCAATATTGCTTA
TTAGGGCCTGATGTATCAAAGTGGCCAGAAATTGAAAAGCAAATGAGTCCCTTATATCAA
GTCAAAGATGGGCAAAACTACCCACCATTCTTATTGTTCCACGGAGATGCTGATAAAGTT
GTTCCATATGAACAGATGGAAAAAATGTATATGCGGTTGAAGGATAATGGAAATTCTGTT
GAAGCGTACCGGGTTAAGGGTGCGAACCATGAACGAGATTTCTGGAGTCCAACAATTTAT
AATATTGTGCAGAAGTTTCTTGGCGATCAATTTAAATAA
```

(14)
```
TTGATTTATGTTTTAAAAGATTTATGTAATACTATTGCTGAAGTCTATGGCAAAAGTATT
TTAAAAGGAGTTTTTATCATGAAACATACGCTTAAAGTTGATCAAGTACGTGACGGTTTA
TGGCTAGATTCAGATATTACGTATACGCAAGTTCCTGGATGGCTTGGTAATACAACGCGA
GATTTGAAGCTTTCAGTCATTCGACATTTTCAAACTAATGATGATACACGTTATCCAGTA
ATTTTTTGGTTTGCTGGTGGCGGCTGGATGGATACTGACCACAATGTTCATCTGCCGAAT
TTGGTTGATTTTGCTCGGCATGGTTACATTGTTGTCGGCGTCGAATATCGTGATAGCAAC
AAAGTTCAGTTTCCTGGGCAATTAGAAGATGCTAAGGCTGCTATTCGTTATATGAGAGCT
AATGCCAAGCGCTTCCAAGCTGATCCTAATCGGTTTATTGTGATGGGAGAATCGGCCGGT
GGACATATGGCAAGTATGCTAGGTGTTACTAACGGCCTTAACCAATTTGACAAAGGTGCT
AATTTAGATTACTCCAGTGATGTTCAAGTAGCAGTTCCTTTTTATGGTGTGGTTGATCCC
TTAACCGCTAAAACAGGAAGTGCATCAAACGATTTTGATTTTGTTTACCGTAACTTGCTT
GGTGCTGAGCCTGAAAACGCTCCTGAGCTTGATTCTGCCGCAAATCCCCTCACCTATGTA
AATTCTAATTCTACGCCCTTTCTTATCTTTCATGGGACAGAAGATGTCGTTGTTCCAATT
AAAGATAGTGAAAAGCTTTATGATGCATTAGTTGAAAACAACGTTCCTGCTGAATTATAC
GAAATCGAAGGCGCAAGTCACATGGATGTGAAATTCCTTCAACCACAGGTATTTAAGATT
GTGATGGACTTTTTAGATAAGTATTTAACTCGGTCATAG
```

(15)
```
ATGGAAATTAAAAGTGTTAACTTAGATCAACCATATTCGTCTCTAGATATTTATCATAGT
AATACTGATAAAGCTTTGCCCGGTCTTGTTATTTTACCAGGAGGCAGTTATAACCAGATC
ATGGAGCGAGATTCTGAACGGGTGGCATTAACGTTTGCAACCCATGCATGGCAAACATTT
```

```
                         -continued
GTTGTACGATATCCGGTAGTTGAGCATAAGAATTATGAAGAAGCCAAAATAGCGGTTCAC
CAAGCATTTGAATATATCGTCAACCATGCAGCTGAATTAGATGTTGACGCTGATCGGTTG
GGGATTATTGGCTTTTCTGCAGGAGGCCAAATTGCCGCTGCATATAGTAATGAAAAACTA
ACACACGCTAGATTCGCCGCATTAGGATATCCTGTTATTCAACCCTTGATTGATGAACGT
ATGGGGGTTACAACAGAGAATGTAGCGAAATTAGTAAATCCGCAAACACCACCAACCTTT
ATGTGGGGATCGGCAAAAGATGAACTGACTCCCTTTGTTGATCACCTTCAAGTATATGCA
GATGCGTTAATTAAGAATGATATTCCATATGAATTACATGAGTTTGGCACTGGGGGACAT
GGAATCGCGTTAGCTAACGAATATACTGGTATTGTTAATAATGATCGGGTAGATAATCAT
ATGGGAAAGTGGTTCCCGCTATTTCTTGAGTGGTTAACTGAACTGAATTTAATTTAG
```

(Sequences Above Disclosed as SEQ ID NOS 2, 4 and 6, Respectively, in Order of Appearance)

Examples of the "stringent condition" as referred to in the invention include a condition under which hybridization is carried out by preserving in a solution containing 6■SSC (composition of 1■SSC: 0.15 M of NaCl, 0.015 M of sodium citrate, pH 7.0), 0.5% SDS, 5■Denhardt and 100■g/mL of thermally denatured herring sperm DNA together with a probe at a temperature of from 50 to 65■C overnight.

Furthermore, the lactic acid bacterium of the invention having the transport gene (4) and the lactic acid bacteria of the invention having each of the genes (9) to (11) encoding a subunit of glycerol-degrading enzyme, the genes (32) to (38) encoding a glycerol-degrading enzyme, the genes (39) to (41) encoding an aldehyde dehydrogenase, the gene (42) encoding a glycerate kinase, the gene (43) encoding a glycerol kinase, the gene (44) encoding a glycerol-3-phosphate dehydrogenase, the genes (45) to (47) encoding triosephosphate isomerase and the gene (12) encoding an enteroadherent protein can also be obtained in the same manner as described above.

Representative examples of the lactic acid bacterium of the invention include Lactobacillus reuteri JCM1112T which is a standard strain of RIKEN, Japan.

The anti-obesity agent of the invention is prepared by processing the foregoing lactic acid bacterium of the invention into a live bacterial agent which can be orally administered and made to arrive at the intestinal tract in a live state as it is. The formulation is not particularly limited and may be, for example, a solid such as a powder, a granule, a tablet and a capsule, a semi-solid such as a jelly and a paste or a liquid such as a suspension and a syrup. These respective formulations can be produced by a known method in the pharmaceutical field.

The lactic acid bacterium of the invention which is blended in the foregoing anti-obesity agent can be cultured by applying a known culture method of lactic acid bacteria. With respect to this culture method, a culture obtained by liquid culturing the lactic acid bacterium of the invention by the ordinary method may be utilized as it is; bacterial cells collected from this culture by means of centrifugation or the like may be used; or a powder obtained by freeze-drying a culture may be used.

As a general production method of the anti-obesity agent of the invention which is a solid, there is exemplified a method in which the lactic acid bacterium of the invention is blended together with a carrier such as water, starch, microcrystalline cellulose, wheat flour and sugar and processed into a desired form. The foregoing carrier is also known and can be properly chosen and used in conformity with the use form. More specifically, powder may be prepared by freeze-drying a bacterial cell of the lactic acid bacterium of the invention as obtained by culturing by the ordinary method to form a powder and mixing it with sugar. Also, a tablet can be obtained by mixing a bacterial cell of the lactic acid bacterium of the invention together with an adequate carrier for tablet and subjecting to tablet making by the ordinary method. Furthermore, a wet bacterial cell of the lactic acid bacterium of the invention may be suspended in a syrup to form a syrup formulation. In preparing the anti-obesity agent of the invention, other components, for example, other microorganisms and active ingredients, sweeteners, flavors and coloring agents may be contained as the need arises.

The dose of the thus obtained anti-obesity agent can be properly determined while taking into consideration the physical state of a subject, for example, state of health, weight, age, medical history and other components to be used. In general, it is from about $10^8$ to $10^9$ CFU/day per an adult in terms of a bacterial number of the lactic acid bacterium of the invention.

Also, in order to prepare an anti-obesity food and drink by using the lactic acid bacterium of the invention, an orally ingestible fermented food may be prepared by utilizing a conventionally known culture method of lactic acid bacteria. Specifically, fermented milk such as yogurt, lactic acid bacteria beverage and fermented sausage can be prepared, and the production of such a food can be achieved by processing apart or the whole of used lactic acid bacteria into the lactic acid bacterium of the invention. Also, the lactic acid bacterium of the invention can be processed into a form containing a larger amount thereof to prepare a healthy food or functional good. In preparing this anti-obesity food, needless to say, other lactic acid bacteria may be contained instead of single use of the lactic acid bacterium of the invention, and food additives or seasonings or the like may be added.

The lactic acid bacterium of the invention shows a significant body weight gain-inhibiting effect (slimming effect) as described later in Examples, and the reasons for this are thought as follows.

That is, as illustrated in FIG. 1, the lactic acid bacterium of the invention degrades a fat in a digestive tract into glycerol and a fatty acid by the action of three lipases (lipases (1) to (3)). The degraded glycerol is then taken into a bacterial cell by a transporter (PduF; encoded by the nucleotide (4)) of the lactic acid bacterium and metabolized by a glycerol-degrading enzyme gene in the bacterial cell (PduCDE; composed of the subunits (5) to (7)) to produce reuterin, or converted into an energy source of the bacterium per se.

On the other hand, the fatty acid is utilized as a bacterial cell component of the present bacterium but not absorbed in a living body. Furthermore, the peptide (8) has such a function to fix the lactic acid bacterium of the invention to the intestinal tract of a human being or a mammal and enables the lactic acid bacterium of the invention to stably exist in the intestinal tract for a fixed period of time.

As has been described previously, since the lactic acid bacterium of the invention stably exists in the intestinal tract, positively degrades a fat and utilizes its metabolites or further metabolizes them, it inhibits the absorption of a lipid from the intestinal tract into the body and even when a normal meal is ingested, is able to prevent obesity from occurring and bring maintenance and improvement of a slimming effect.

Also, an embodiment of the invention includes the use of the lactic acid bacterium of the invention for the prevention or therapy of obesity and further includes the use of the lactic acid bacterium of the invention for the production of an anti-obesity agent.

Moreover, another embodiment of the invention includes a method for therapy of obesity, which is characterized by administering a patient suffering from obesity with the lactic acid bacterium of the invention and also a method for therapy of obesity, which is characterized by administering the anti-obesity agent of the invention.

EXAMPLES

The invention is hereunder described in more detail with reference to the following Examples, but it should be construed that the invention is not limited to these Examples at all.

Example 1

Anti-Obesity Effect Test of *L. reuteri* JCM1112T

An anti-obesity effect of *L. reuteri* JCM1112T was examined by the following materials and method.
Materials and Test Method:
(1) Experimental Animal:
Wistar rats of SPF grade (males of 8-week-old; Japan SLC, Inc.) having a body weight of from about 180 to 200 g were used, an acclimatization period of 7 days from the day for the sending in a laboratory was provided, and the experiment was then started. The breeding circumstance was set up at a temperature of 22■1 ■C, a humidity of 55■5% and a lighting time of 12 hours (from 8:00 to 20:00); and the rats were caged individually and provided with free access to sterile distilled water through a watering bottle and a radiation-sterilized solid diet■for rat (CE-2, CLEA Japan, Inc.) by a feeder, respectively. All of the breeding instruments to be used were ones sterilized by a high-pressure steam sterilizer.
■: Use for breeding and propagation (crude fat: 4.6%)
(2) Preparation of Test Bacterial Solution:
As test bacteria, *L. reuteri* JCM1112T (a standard strain of RIKEN, Japan, which was received from the same) and *L. rhamnosus* ATCC53103 (GG strain) (obtainable inter alia from Valio Oy of Finland under the trade mark LGG and from American Type Culture Collection, 10801 University Boulevard, Manassas, Va. 20110, USA) were used. These test bacteria were inoculated in an MRS liquid medium (Oxid) and cultured at 37° C. overnight to prepare pre-culture solutions. An MRS liquid medium was newly added such that the concentration of this pre-culture solution was 1% and cultured at 37° C. for 18 hours to prepare a test bacterial solution.
(3) Administration of Test Bacterial Solution:
The foregoing experimental animals were divided into two test bacterial groups and a control group (five animals per group), and the foregoing test bacterial solutions were orally administered in the test bacterial groups respectively. The test bacterial solution was forcibly administered via probe. The bacterial solutions were prepared at the time of use, and the bacterial dose was set up at $10^9$ CFU per rat. Also, the control group was administered with the same volume of PBS.
(4) Measurement of Body Weight and General Observation of Symptoms:
The body weight of the experimental animal was measured every day by a scale. General observation of symptoms was made every day. The symptoms were recorded for every individual, and symptom items at which a remarkable change was observed were expressed in terms of number of the animals.

(5) Results:
FIG. 2 shows the body weight gain with time in the rats of the groups administered either of the foregoing *Lactobacillus* bacteria and the control group. As is clear from this drawing, in the *L. reuteri* JCM1112T group, the body weight gain was significantly inhibited as compared with the control group, and the degree of the inhibition was larger than that in the *L. rhamnosus* ATCC53103 group.

As well as favorable progress of the body weight gain, a medical examination of the rats of each group confirmed that the state of health of the animals was good.

Example 2

Genome Analysis of *L. reuteri* JCM1112T

DNA was obtained from *L. reuteri* JCM1112T by using the following chemicals in the following method, thereby achieving genome analysis.
Method for Obtaining DNA:
(Chemicals)
  Nuclei Lysis solution (Wizard genome DNA purification kit; manufactured by Promega)
  Physiological saline
  50 mM EDTA (pH: 7.0)
  50 mg/mL lysozyme solution (prepared on the day by dissolving a prescribed amount of lysozyme in a TE buffer solution, 0.25 M Tris-HCl (pH 8.0) or 10 mM Tris-HCl (pH 8.0)/10 mM EDTA/0.5% SDS)
  2 mg/mL EDTA
  Phenol/chloroform/isoamyl alcohol (25:24:1) mixed solution (hereinafter abbreviated as "PCI")
  Chloroform/isoamyl alcohol (24:1) mixed solution (hereinafter abbreviated as "CIA")
  99% Ethanol
  70% Ethanol
  TE buffer solution
(Method)
1. *L. reuteri* JCM1112T is cultured at 37■C for 24 hours under static conditions, and the obtained culture solution (50 mL) is centrifuged at 3,500 r.p.m. for 15 minutes and then suspended in physiological saline.
2. The suspension as obtained in 1 is centrifuged at 3,500 r.p.m. for 15 minutes, a supernatant is removed, and the residue is suspended in 5 mL of 50 mM EDTA.
3. To the suspension as obtained in 2, 200■L of a 50 mg/mL lysozyme solution is added and incubated at 37■C for 60 minutes. (On that occasion, in the case where an air incubator is used, the incubation time is set up at from 2 to 3 hours.)
4. After the incubation, the resultant is centrifuged at 3,500 r.p.m. for 15 hours, and a supernatant is removed.
5. To the precipitate as obtained in 4, 5 mL of a Nuclei Lysis solution is added and incubated at 80■C for 10 minutes.
6. 1 ■L of 2 mg/mL RNase A is added and incubated at 37■C for 45 minutes.
7. 10 mL of PCI is added and mixed, and the mixture is centrifuged at 3,500 r.p.m. for 15 minutes.
8. A supernatant is transferred into a new tube, and 10 mL of PCI is further added and mixed.
9. The same operations are repeated 3 times in total. (The operations are carried out until no protein layer is identified.)
10. 10 mL of CIA is added and gently mixed, and the mixture is then centrifuged at 3,500 r.p.m for 15 minutes (removal of phenol).
11. A supernatant is transferred into a new tube, followed by precipitation with ethanol.

12. A precipitate as obtained in 11 is dissolved in 1 mL of a TE buffer solution to obtain a lactic acid bacterium DNA.

Genome Analysis Method:

The DNA thus obtained was subjected to structural gene prediction and annotation. The structural gene prediction and the like were carried out by combining the results of GENOMEGAMBLER (Sakiyama, T., Takami, H., Ogasawara, N., Kuhara, S., Kozuki, T., Doga, K., Ohyama, A., Horikoshi, K., "An automated system for genome analysis to support microbial whole-genome shotgun sequencing", *Biosci. Biotechnol. Biochem.*, 64: 670 to 673 2000), GLIMMER 2.0 (Salzberg, S L., Delcher, A L., Kasif, S., and White, O., "Microbial gene identification using interpolated Markov models", *Nucleic. Acid. Res.*, 26: 544 to 548, 1998) and BLAST program blastp (Altschul, S F., Gish, W., Miller, W., Myers, E W., and Lipman, D J., "Basic local alignment search tool", *J. Mol. Biol.*, 215: 403 to 410, 1990).

Also, INTERPRO (Mulder, N J., Apweiler, R., Attwood, T K., Bairoch, A., Barrell, D., Bateman, A., Binns, D., Biswas, M., Bradley, P., Bork, P., Bucher, P., Copley, R R., Courcelle, E., Das, U., Durbin, R., Falquet, L., Fleischmann, W., Griffiths-Jones, S., Haft, D., Harte, N., Hulo, N., Kahn, D., Kanapin, A., Krestyaninova, M., Lopez, R., Letunic, I., Lonsdale, D., Silventoinen, V., Orchard, S E., Pagni, M., Peyruc, D., Ponting, C P., Selengut, J D., Servant, F., Sigrist, C J., Vaughan, R., and Zdobnov, E M., "The InterPro Database, 2003 brings increased coverage and new features", *Nucleic. Acids. Res.*, 31: 315 to 318, 2003; http://www.ebi.ac.uk/interpro) was used for the analysis of a domain structure; and CLUSTALW (Thompson, J D., Higgins, D G., and Gibson, T J., "CLUSTAL W: improving the sensitivity of progressive multiple sequence alignment through sequence weighting, position-specific gap penalties and weight matrix choice", *Nucleic. Acids. Res.*, 22: 4673 to 4680, 1994; http://clustalw-.genome.ad.jp/) was used for the preparation of a molecular phylogenetic tree.

Furthermore, the used DNA and amino acid sequences were obtained from National Center of Biological Information (NCBI, http://www.ncbi.nlm.nih.gov) and KEGG database (Ogata, H., Goto, S., Sato, K., Fujibuchi, W., Bono, H., and Kanehisa, M., "KEGG: Kyoto Encyclopedia of Genes and Genomes", *Nucleic. Acids. Res.*, 27: 29 to 34, 1999; http://www.genome.ad.jp/kegg/kegg2.html); and a draft sequence of the *Lactobacillus* bacterium was obtained from DOE JOINT GENOME INSTITUTE (JGI; http://www.jgi-.doe.gov/JGI_microbial/html/index.html).

Based on the foregoing information, the genes depicted in (13) to (15) were identified as encoding the lipases; the gene depicted in (4) as encoding a transporter gene; the genes depicted in (9), (10) and (11) as encoding a glycerol-degrading enzyme; and the gene depicted in (12) as an adhesive gene, respectively. Also, the genes depicted in (32) to (38) were identified as encoding a glycerol-degrading enzyme; the genes depicted in (39) to (41) as encoding an aldehyde dehydrogenase; the gene depicted in (42) as encoding a glycerate kinase; the gene depicted in (43) as encoding a glycerol kinase; the gene depicted in (44) as encoding a glycerol-3-phosphate dehydrogenase; and the genes depicted in (45) to (47) as encoding triosephosphate isomerase, respectively.

Example 3

Amplification of Glycerol-Degrading Gene

PCR was carried out by using DNA as purified in Example 2 as a template and the following nucleotide sequences as primers and using the following reaction solutions. The PCR condition is also shown below.

```
(Primer)
pduCDE(F):
CACCATGAAACGTCAAAAACGATTT
(SEQ ID NO: 49)

pduCDE(R):
AAAAGCTTAGTTATCGCCCTTTAGC
(SEQ ID NO: 50)
```

(PCR Reaction Solution)
Template DNA: 1■L
KOD-plus: 1■L
10■KOD-plus buffer solution: 5■L
dNTP (2 mM each): 5■L
Primer (20 mm): 1■L each
MgSO$_4$ (25 mm): 2■L
Deionized water (D.W.): 34■L (PCR Condition)
(1) To hold at 94■C for 3 minutes.
(2) To hold at 94■C for 15 seconds.
(3) To hold at 56■C (Tm) for 30 seconds.
(4) To hold at 68■C for 3 minutes 30 seconds.
(5) To perform (2) to (4) in 30 cycles.
(6) To preserve at 4■C.

Example 4

Amplification of *L. Reuteri*-Derived Lipase Gene and Adhesive Gene

PCR was carried out in the same manner as in Example 3, except using the following sequences as primers, thereby amplifying the lipase gene and adhesive gene.

```
(Primer)
Lipase (1)
5'-ATGGTGAAATTGATGACAAT
(SEQ ID NO: 51)

5'-TTATTTAAATTGATCGCCAA
(SEQ ID NO: 52)

Lipase (2)
5'-TTGATTTATGTTTTAAAAGA
(SEQ ID NO: 53)

5'-CTATGACCGAGTTAAATACT
(SEQ ID NO: 54)

Lipase (3)
5'-ATGGAAATTAAAAGTGTTAA
(SEQ ID NO: 55)

5'-CTAAATTAAATTCAGTTCAG
(SEQ ID NO: 56)

Adhesive gene
5'-ATGTTCGGTCACGATGGCCG
(SEQ ID NO: 57)

5'-TCAAATTTCAGAAGGATCAT
(SEQ ID NO: 58)
```

INDUSTRIAL APPLICABILITY

As is clear from the results of the foregoing Examples using *L. reuteri* JCM1112T which is a representative of the lactic acid bacterium of the invention, the administration of this microorganism could inhibit the body weight gain without affecting the health of the experimental animals and without particularly limiting nutrition intake.

Accordingly, the anti-obesity agent or anti-obesity food and drink utilizing the lactic acid bacterium of the invention is able to prevent obesity and to bring a slimming effect without requiring particular therapy or treatment other than intake of the agent, or the food or drink per se.

Also, by incorporating genes encoding subunits of a glycerol-degrading enzyme or a gene encoding an enteroadherent protein, each of which has been found out from the lactic acid bacterium of the invention, into other lactic acid bacterium by a known measure, it becomes possible to obtain a lactic acid bacterium with high glycerol-degrading properties or a lactic acid bacterium with a long intestinal residence time. It is also possible to advantageously use it for the modification of other useful lactic acid bacteria.

SEQUENCE LISTING

<160> NUMBER OF SEQ ID NOS: 58

Figure 1:
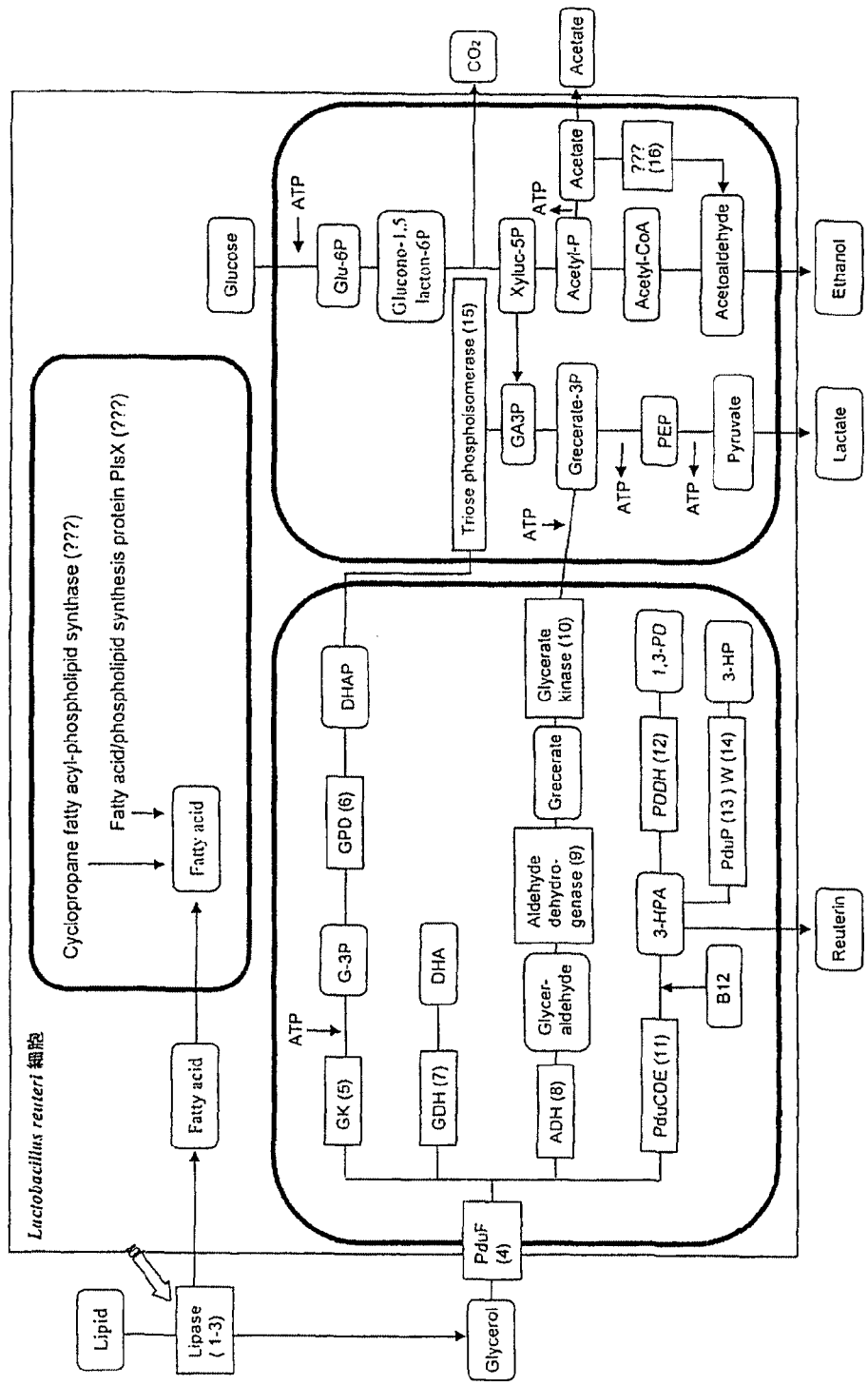
FIG. 1 is a drawing showing a metabolism map of L. reuteri JCM1112T.
Figure 2:
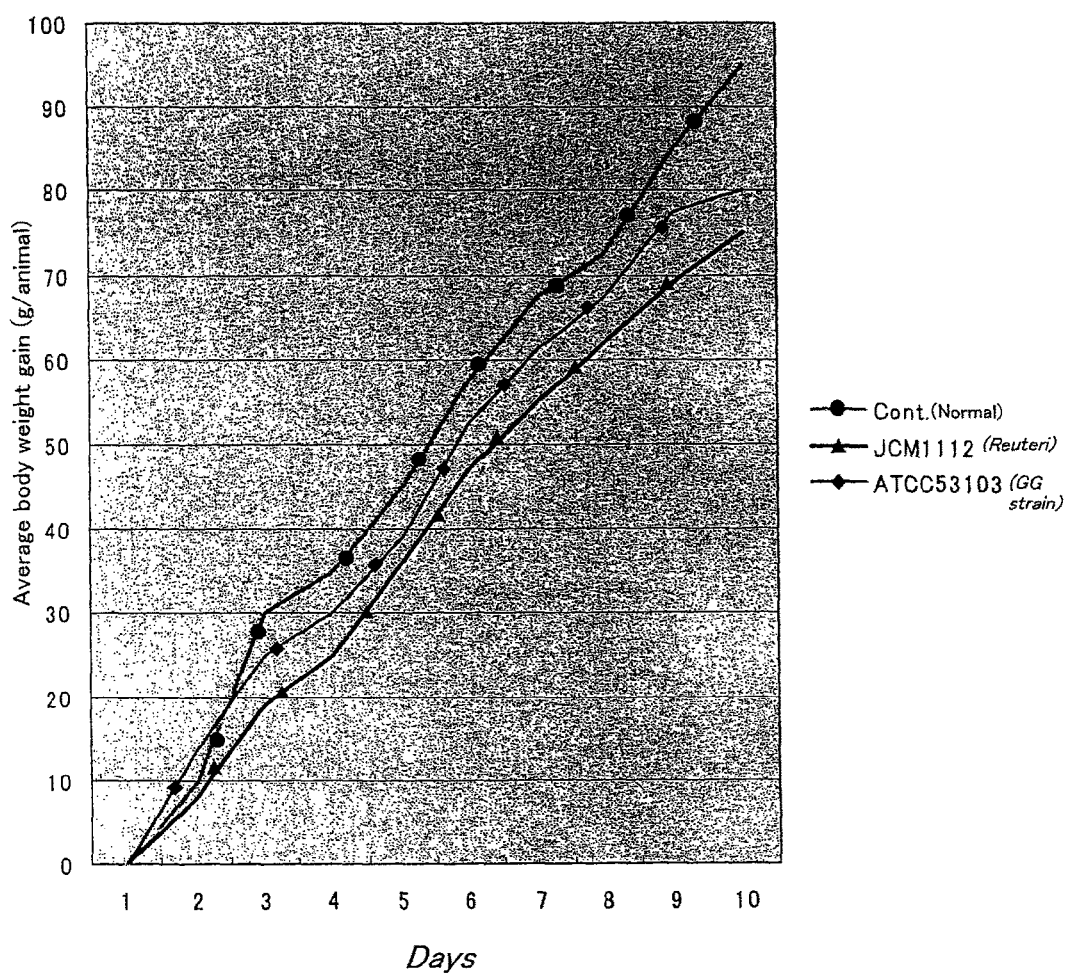
FIG. 2 is a drawing showing the body weight gain with time in the rats administered with L. reuteri JCM1112T in comparison with the comparative group and the control group.

<210> SEQ ID NO 1
<211> LENGTH: 292
<212> TYPE: PRT
<213> ORGANISM: Lactobacillus reuteri

<400> SEQUENCE: 1

```
Met Val Lys Leu Met Thr Ile His Glu Leu Ala Asn Asn Pro Thr Leu
1               5                   10                  15

Ser Gly Gln Val Arg Leu Ile Glu Asn Ile Val Tyr Gly Ala Met Asp
                20                  25                  30

Gly Glu Ala Leu His Met Ser Ile Leu Ala Pro Trp Thr Gln Arg Phe
            35                  40                  45

Pro Lys Gln Tyr Gln Thr Glu Pro Arg Pro Leu Ile Val Phe Val Gln
        50                  55                  60

Gly Ser Ser Trp Arg Thr Pro Lys Met Gly Glu Glu Ile Pro Gln Leu
65                  70                  75                  80

Val Gln Phe Val Arg Ala Gly Tyr Ile Val Ala Thr Val Gln His Arg
                85                  90                  95

Ser Ser Ile Asp Ser His Pro Phe Pro Ala Phe Leu Gln Asp Val Lys
            100                 105                 110

Thr Ala Ile Arg Phe Leu Arg Ala Asn Ala Gln Lys Tyr Ala Ile Asp
        115                 120                 125

Pro Gln Gln Val Ala Ile Trp Gly Thr Ser Ser Gly Ala Asn Ala Ala
    130                 135                 140

Met Leu Val Gly Leu Thr Gly Asp Asp Pro Arg Tyr Lys Val Asp Leu
145                 150                 155                 160

Tyr Gln Asp Glu Ser Asp Ala Val Asp Ala Val Val Ser Cys Phe Ala
                165                 170                 175

Pro Met Asp Val Glu Lys Thr Phe Glu Tyr Asp Ala Asn Val Pro Gly
            180                 185                 190

Asn Lys Leu Leu Gln Tyr Cys Leu Leu Gly Pro Asp Val Ser Lys Trp
        195                 200                 205

Pro Glu Ile Glu Lys Gln Met Ser Pro Leu Tyr Gln Val Lys Asp Gly
    210                 215                 220

Gln Asn Tyr Pro Pro Phe Leu Leu Phe His Gly Asp Ala Asp Lys Val
225                 230                 235                 240

Val Pro Tyr Glu Gln Met Glu Lys Met Tyr Met Arg Leu Lys Asp Asn
                245                 250                 255

Gly Asn Ser Val Glu Ala Tyr Arg Val Lys Gly Ala Asn His Glu Arg
            260                 265                 270

Asp Phe Trp Ser Pro Thr Ile Tyr Asn Ile Val Gln Lys Phe Leu Gly
```

```
                    275                 280                 285

Asp Gln Phe Lys
    290

<210> SEQ ID NO 2
<211> LENGTH: 879
<212> TYPE: DNA
<213> ORGANISM: Lactobacillus reuteri

<400> SEQUENCE: 2
atggtgaaat tgatgacaat acacgaatta gcaaataacc caacgttaag cggccaagta      60
cgcttgattg aaaatattgt ttatggtgcg atggatggtg aggcattaca tatgtcgatc     120
ttagcaccgt ggacgcaacg tttcccgaaa caatatcaaa ctgaacctcg accattgatt     180
gtctttgttc aaggaagctc gtggcgaaca ccaaaaatgg gagaagaaat tccacaactg     240
gttcaatttg ttcgggccgg ttatattgta gcgactgttc aacaccgtag ttcaattgat     300
agccacccat ttcctgcctt tttgcaagat gttaagactc ccattcgttt cttacgggcc     360
aatgcgcaaa atatgcaat tgatccgcaa caggttgcaa tttgggggac ttcctctgga     420
gccaatgcgg caatgctagt cggcttaacg ggtgatgatc cgcgctataa agttgacctt     480
tatcaagacg aatcggatgc agtagatgct gtggttagtt gttttgcccc aatggacgtg     540
gagaagacgt tgagtatga tgctaatgtt ccaggaaata agttactgca atattgctta     600
ttagggcctg atgtatcaaa gtggccagaa attgaaaagc aaatgagtcc cttatatcaa     660
gtcaaagatg ggcaaaacta cccaccattc ttattgttcc acggagatgc tgataaagtt     720
gttccatatg aacagatgga aaaaatgtat atgcggttga aggataatgg aaattctgtt     780
gaagcgtacc gggttaaggg tgcgaaccat gaacgagatt tctggagtcc aacaatttat     840
aatattgtgc agaagtttct tggcgatcaa tttaaataa                            879

<210> SEQ ID NO 3
<211> LENGTH: 312
<212> TYPE: PRT
<213> ORGANISM: Lactobacillus reuteri

<400> SEQUENCE: 3

Leu Ile Tyr Val Leu Lys Asp Leu Cys Asn Thr Ile Ala Glu Val Tyr
1               5                   10                  15

Gly Lys Ser Ile Leu Lys Gly Val Phe Ile Met Lys His Thr Leu Lys
            20                  25                  30

Val Asp Gln Val Arg Asp Gly Leu Trp Leu Asp Ser Ile Thr Tyr
        35                  40                  45

Thr Gln Val Pro Gly Trp Leu Gly Asn Thr Thr Arg Asp Leu Lys Leu
    50                  55                  60

Ser Val Ile Arg His Phe Gln Thr Asn Asp Asp Thr Arg Tyr Pro Val
65                  70                  75                  80

Ile Phe Trp Phe Ala Gly Gly Trp Met Asp Thr Asp His Asn Val
                85                  90                  95

His Leu Pro Asn Leu Val Asp Phe Ala Arg His Gly Tyr Ile Val Val
            100                 105                 110

Gly Val Glu Tyr Arg Asp Ser Asn Lys Val Gln Phe Pro Gly Gln Leu
        115                 120                 125

Glu Asp Ala Lys Ala Ala Ile Arg Tyr Met Arg Ala Asn Ala Lys Arg
    130                 135                 140

Phe Gln Ala Asp Pro Asn Arg Phe Ile Val Met Gly Glu Ser Ala Gly
145                 150                 155                 160
```

```
Gly His Met Ala Ser Met Leu Gly Val Thr Asn Gly Leu Asn Gln Phe
                165                 170                 175
Asp Lys Gly Ala Asn Leu Asp Tyr Ser Ser Asp Val Gln Val Ala Val
            180                 185                 190
Pro Phe Tyr Gly Val Val Asp Pro Leu Thr Ala Lys Thr Gly Ser Ala
        195                 200                 205
Ser Asn Asp Phe Asp Phe Val Tyr Arg Asn Leu Leu Gly Ala Glu Pro
    210                 215                 220
Glu Asn Ala Pro Glu Leu Asp Ser Ala Ala Asn Pro Leu Thr Tyr Val
225                 230                 235                 240
Asn Ser Asn Ser Thr Pro Phe Leu Ile Phe His Gly Thr Glu Asp Val
                245                 250                 255
Val Val Pro Ile Lys Asp Ser Glu Lys Leu Tyr Asp Ala Leu Val Glu
            260                 265                 270
Asn Asn Val Pro Ala Glu Leu Tyr Glu Ile Glu Gly Ala Ser His Met
        275                 280                 285
Asp Val Lys Phe Leu Gln Pro Gln Val Phe Lys Ile Val Met Asp Phe
    290                 295                 300
Leu Asp Lys Tyr Leu Thr Arg Ser
305                 310

<210> SEQ ID NO 4
<211> LENGTH: 939
<212> TYPE: DNA
<213> ORGANISM: Lactobacillus reuteri

<400> SEQUENCE: 4
ttgatttatg tttaaaaga tttatgtaat actattgctg aagtctatgg caaaagtatt      60
ttaaaggag tttttatcat gaaacatacg cttaaagttg atcaagtacg tgacggttta    120
tggctagatt cagatattac gtatacgcaa gttcctggat ggcttggtaa tacaacgcga    180
gatttgaagc tttcagtcat tcgacatttt caaactaatg atgatacacg ttatccagta    240
attttttggt tgctggtgg cggctggatg gatactgacc acaatgttca tctgccgaat    300
ttggttgatt ttgctcggca tggttacatt gttgtcggcg tcgaatatcg tgatagcaac    360
aaagttcagt ttcctgggca attagaagat gctaaggctg ctattcgtta tatgagagct    420
aatgccaagc gcttccaagc tgatcctaat cggtttattg tgatgggaga atcggccggt    480
ggacatatgg caagtatgct aggtgttact aacggcctta accaatttga caaaggtgct    540
aatttagatt actccagtga tgttcaagta gcagttcctt tttatggtgt ggttgatccc    600
ttaaccgcta aaacaggaag tgcatcaaac gattttgatt ttgtttaccg taacttgctt    660
ggtgctgagc ctgaaaacgc tcctgagctt gattctgccg caaatcccct cacctatgta    720
aattctaatt ctacgccctt tcttatcttt catgggacag aagatgtcgt tgttccaatt    780
aaagatagtg aaaagcttta tgatgcatta gttgaaaaca acgttcctgc tgaattatac    840
gaaatcgaag cgcaagtca catggatgtg aaattcctc aaccacaggt atttaagatt    900
gtgatggact ttttagataa gtatttaact cggtcatag                            939

<210> SEQ ID NO 5
<211> LENGTH: 238
<212> TYPE: PRT
<213> ORGANISM: Lactobacillus reuteri

<400> SEQUENCE: 5

Met Glu Ile Lys Ser Val Asn Leu Asp Gln Pro Tyr Ser Ser Leu Asp
```

```
             1               5                  10                 15
Ile Tyr His Ser Asn Thr Asp Lys Ala Leu Pro Gly Leu Val Ile Leu
                    20                  25                  30

Pro Gly Gly Ser Tyr Asn Gln Ile Met Glu Arg Asp Ser Glu Arg Val
                35                  40                  45

Ala Leu Thr Phe Ala Thr His Ala Trp Gln Thr Phe Val Val Arg Tyr
        50                  55                  60

Pro Val Val Glu His Lys Asn Tyr Glu Ala Lys Ile Ala Val His
65                  70                  75                  80

Gln Ala Phe Glu Tyr Ile Val Asn His Ala Ala Glu Leu Asp Val Asp
                    85                  90                  95

Ala Asp Arg Leu Gly Ile Ile Gly Phe Ser Ala Gly Gly Gln Ile Ala
                100                 105                 110

Ala Ala Tyr Ser Asn Glu Lys Leu Thr His Ala Arg Phe Ala Ala Leu
            115                 120                 125

Gly Tyr Pro Val Ile Gln Pro Leu Ile Asp Glu Arg Met Gly Val Thr
        130                 135                 140

Thr Glu Asn Val Ala Lys Leu Val Asn Pro Gln Thr Pro Thr Phe
145                 150                 155                 160

Met Trp Gly Ser Ala Lys Asp Glu Leu Thr Pro Phe Val Asp His Leu
                165                 170                 175

Gln Val Tyr Ala Asp Ala Leu Ile Lys Asn Asp Ile Pro Tyr Glu Leu
                180                 185                 190

His Glu Phe Gly Thr Gly Gly His Gly Ile Ala Leu Ala Asn Glu Tyr
                195                 200                 205

Thr Gly Ile Val Asn Asn Asp Arg Val Asp Asn His Met Gly Lys Trp
        210                 215                 220

Phe Pro Leu Phe Leu Glu Trp Leu Thr Glu Leu Asn Leu Ile
225                 230                 235

<210> SEQ ID NO 6
<211> LENGTH: 717
<212> TYPE: DNA
<213> ORGANISM: Lactobacillus reuteri

<400> SEQUENCE: 6
atggaaatta aaagtgttaa cttagatcaa ccatattcgt ctctagatat ttatcatagt      60
aatactgata aagctttgcc cggtcttgtt attttaccag gaggcagtta taccagatc      120 atggagcgag attctgaacg ggtggcatta acgtttgcaa cccatgcatg caaacatt       180 gttgtacgat atccggtagt tgagcataag aattatgaag aagccaaaat agcggttcac      240
caagcatttg aatatatcgt caaccatgca gctgaattag atgttgacgc tgatcggttg      300
gggattattg gcttttctgc aggaggccaa attgccgctg catatagtaa tgaaaaacta      360
acacacgcta gattcgccgc attaggatat cctgttattc aacccttgat tgatgaacgt      420
atgggggtta caacagagaa tgtagcgaaa ttagtaaatc cgcaaacacc accaaccttt      480
atgtggggat cggcaaaaga tgaactgact ccctttgttg atcaccttca gtatatgca       540 gatgcgttaa ttaagaatga tattccatat gaattacatg agtttggcac tgggggacat      600
ggaatcgcgt tagctaacga atatactggt attgttaata atgatcgggt agataatcat      660
atgggaaagt ggttcccgct atttcttgag tggttaactg aactgaattt aatttag        717

<210> SEQ ID NO 7
<211> LENGTH: 235
<212> TYPE: PRT
```

```
<213> ORGANISM: Lactobacillus reuteri

<400> SEQUENCE: 7

Met His Gly Phe Ile Gly Glu Phe Phe Gly Thr Met Val Leu Ile Leu
1               5                   10                  15

Leu Gly Ala Gly Cys Cys Ala Gly Asn Ser Leu Asn Lys Thr Tyr Gly
            20                  25                  30

Lys Gln Ser Gly Trp Trp Phe Ile Cys Ile Ser Trp Gly Leu Ala Val
        35                  40                  45

Thr Met Gly Val Tyr Val Ala Gly Phe Gly Ser Leu Gly His Leu
    50                  55                  60

Asn Pro Ala Val Thr Ile Pro Phe Ala Ile Phe Gly Leu Phe Pro Trp
65                  70                  75                  80

Ser Asn Val Ile Pro Tyr Leu Leu Gly Gln Phe Leu Gly Ala Phe Val
                85                  90                  95

Gly Ala Val Leu Val Ile Ile Gln Phe Tyr Pro Gln Phe Lys Ala Thr
            100                 105                 110

Pro Asn Glu Glu Glu Gly Asn Asn Val Gly Ile Phe Ala Thr Arg Pro
        115                 120                 125

Ala Ile Asn Ser Pro Ile Phe Asn Phe Phe Ser Glu Val Ile Ala Thr
    130                 135                 140

Phe Ala Phe Ile Phe Ile Leu Leu Asn Leu Gly Asn Phe Thr Gln Gly
145                 150                 155                 160

Leu Lys Pro Phe Ile Val Gly Met Val Ile Ala Val Val Gly Thr Cys
                165                 170                 175

Leu Gly Thr Thr Thr Gly Phe Ala Leu Asn Pro Ala Arg Asp Trp Ser
            180                 185                 190

Pro Arg Leu Ala Tyr Thr Ile Leu Pro Ile Pro Asn Lys Gly Val Ser
        195                 200                 205

Glu Trp Trp Tyr Ala Trp Val Pro Met Cys Gly Pro Ile Val Gly Gly
    210                 215                 220

Leu Leu Ala Cys Ala Leu Gln Thr Ala Leu Val
225                 230                 235

<210> SEQ ID NO 8
<211> LENGTH: 708
<212> TYPE: DNA
<213> ORGANISM: Lactobacillus reuteri

<400> SEQUENCE: 8
atgcatggat ttattggcga attttttggc accatggttt taatcctatt aggagcagga    60
tgttgtgctg gtaatagttt gaataaaaca tatgggaaac aaagtggctg gtggtttatc   120
tgtatttcat ggggcttagc agttacaatg ggagtttatg ttgcaggatt tctgggttca   180
ttagggcact taaatcccgc tgtaacaatt ccttttgcta tttttggctt attcccatgg   240
agtaacgtta taccttactt acttggtcaa tttcttggtg cgtttgttgg tgcagtatta   300
gtaattattc aattctatcc acaatttaaa gcaaccccaa atgaagaaga aggaaataat   360
gttggtattt ttgctactcg tccagcgata aatagtccaa ttttttaactt tttctcagaa   420 gtgattgcga cctttgcatt tattttcatc ttattaaatc ttggcaactt acacaggga   480 ttgaagccat ttatcgtagg aatggttatt gcagttgttg gtacatgtct cgggacaact   540
actggctttg cattaaaccc agctcgtgat tggtcaccac gtttagcata tactattttg   600
ccaattccta ataagggtgt ttcagaatgg tggtatgcat gggttccaat gtgtgggcca   660
attgttgggg gccttcttgc ttgtgcttta caaacggcac tagttttag               708
```

```
<210> SEQ ID NO 9
<211> LENGTH: 558
<212> TYPE: PRT
<213> ORGANISM: Lactobacillus reuteri

<400> SEQUENCE: 9

Met Lys Arg Gln Lys Arg Phe Glu Glu Leu Glu Lys Arg Pro Ile His
1               5                   10                  15

Gln Asp Thr Phe Val Lys Glu Trp Pro Glu Glu Gly Phe Val Ala Met
            20                  25                  30

Met Gly Pro Asn Asp Pro Lys Pro Ser Val Lys Val Glu Asn Gly Lys
        35                  40                  45

Ile Val Glu Met Asp Gly Lys Lys Leu Glu Asp Phe Asp Leu Ile Asp
    50                  55                  60

Leu Tyr Ile Ala Lys Tyr Gly Ile Asn Ile Asp Asn Val Glu Lys Val
65                  70                  75                  80

Met Asn Met Asp Ser Thr Lys Ile Ala Arg Met Leu Val Asp Pro Asn
                85                  90                  95

Val Ser Arg Asp Glu Ile Ile Glu Ile Thr Ser Ala Leu Thr Pro Ala
            100                 105                 110

Lys Ala Glu Glu Ile Ile Ser Lys Leu Asp Phe Gly Glu Met Ile Met
        115                 120                 125

Ala Val Lys Lys Met Arg Pro Arg Lys Pro Asp Asn Gln Cys His
    130                 135                 140

Val Thr Asn Thr Val Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Phe Asn Ala Ile Ser Ile Leu Ile Gly Ala Gln
            180                 185                 190

Thr Gly Arg Pro Gly Val Leu Thr Gln Cys Ser Val Glu Glu Ala Thr
        195                 200                 205

Glu Leu Gln Leu Gly Met Arg Gly Phe Thr Ala Tyr Ala Glu Thr Ile
    210                 215                 220

Ser Val Tyr Gly Thr Asp Arg Val Phe Thr Asp Gly Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Val Leu Met Gly Tyr Pro
            260                 265                 270

Glu Gly Lys Ser Met Leu Tyr Leu Glu Ala Arg Cys Ile Leu Leu Thr
        275                 280                 285

Lys Ala Ser Gly Val Gln Gly Leu Gln Asn Gly Ala Val Ser Cys Ile
    290                 295                 300

Glu Ile Pro Gly Ala Val Pro Asn Gly Ile Arg Glu Val Leu Gly Glu
305                 310                 315                 320

Asn Leu Leu Cys Met Met Cys Asp Ile Glu Cys Ala Ser Gly Cys Asp
                325                 330                 335

Gln Ala Tyr Ser His Ser Asp Met Arg Arg Thr Glu Arg Phe Ile Gly
            340                 345                 350

Gln Phe Ile Ala Gly Thr Asp Tyr Ile Asn Ser Gly Tyr Ser Ser Thr
        355                 360                 365

Pro Asn Tyr Asp Asn Thr Phe Ala Gly Ser Asn Thr Asp Ala Met Asp
    370                 375                 380
```

```
Tyr Asp Asp Met Tyr Val Met Glu Arg Asp Leu Gly Gln Tyr Tyr Gly
385                 390                 395                 400

Ile His Pro Val Lys Glu Glu Thr Ile Ile Lys Ala Arg Asn Lys Ala
            405                 410                 415

Ala Lys Ala Leu Gln Ala Val Phe Glu Asp Leu Gly Leu Pro Lys Ile
        420                 425                 430

Thr Asp Glu Glu Val Glu Ala Ala Thr Tyr Ala Asn Thr His Asp Asp
    435                 440                 445

Met Pro Lys Arg Asp Met Val Ala Asp Met Lys Ala Ala Gln Asp Met
450                 455                 460

Met Asp Arg Gly Ile Thr Ala Ile Asp Ile Ile Lys Ala Leu Tyr Asn
465                 470                 475                 480

His Gly Phe Lys Asp Val Ala Glu Ala Ile Leu Asn Leu Gln Lys Gln
            485                 490                 495

Lys Val Val Gly Asp Tyr Leu Gln Thr Ser Ser Ile Phe Asp Lys Asp
        500                 505                 510

Trp Asn Val Thr Ser Ala Val Asn Asp Gly Asn Asp Tyr Gln Gly Pro
    515                 520                 525

Gly Thr Gly Tyr Arg Leu Tyr Glu Asp Lys Glu Glu Trp Asp Arg Ile
530                 535                 540

Lys Asp Leu Pro Phe Ala Leu Asp Pro Glu His Leu Glu Leu
545                 550                 555

<210> SEQ ID NO 10
<211> LENGTH: 1677
<212> TYPE: DNA
<213> ORGANISM: Lactobacillus reuteri

<400> SEQUENCE: 10
atgaaacgtc aaaaacgatt tgaagaacta gaaaaacggc caattcatca agatacattt      60
gttaaagaat ggccagaaga aggtttcgtt gcaatgatgg ggcctaatga ccctaagcct     120
agtgtaaaag ttgaaaatgg caagatcgta gagatggatg gtaaaaagct cgaagatttt     180
gatttgattg acttgtacat tgctaagtat ggaatcaata ttgacaacgt tgaaaaagtt     240
atgaatatgg attctaccaa gattgcacgg atgcttgttg atcctaatgt ttctcgtgat     300
gaaattattg aaattacatc agctttgact cctgctaagg ctgaagagat catcagtaag     360
cttgattttg gtgaaatgat tatggctgtc aagaagatgc gcccacgtcg taagcctgac     420
aaccagtgtc acgttaccaa tactgttgat aacccagttc aaattgctgc tgatgctgct     480
gatgccgctc ttcgtggatt tccagaacaa gaaaccacga cagctgtggc acgttatgca     540
ccattcaatg ctatttcaat tttaattggt gcacaaacag tcgccctgg tgtattgaca     600 caatgttctg ttgaagaagc tactgaattg caattaggta tgcgtggttt taccgcatat     660
gctgaaacca tttcagttta cggtactgat cgtgtattta ccgatggtga tgatactcca     720
tggtctaaag gcttcttggc atcttgttat gcatcacgtg gtttgaagat gcgatttact     780
tcaggtgccg ttcagaagt tttgatgggt atccagaag gtaagtcaat gcttacctt     840 gaagcgcgtt gtattttact tactaaggct tcaggtgttc aaggacttca aaatggtgcc     900
gtaagttgta ttgaaattcc tggtgctgtt cctaatggta ttcgtgaagt ctcggtgaa     960 aacttgttat gtatgatgtg tgacatcgaa tgtgcttctg gttgtgacca agcatactca    1020
cactccgata tgcggcggac tgaacggttt attggtcaat ttattgccgg tactgattat    1080
attaactctg gttactcatc aactcctaac tacgataata ccttcgctgg ttcaaacact    1140
```

-continued

```
gatgctatgg actacgatga tatgtatgtt atggaacgtg acttgggtca atattatggt      1200
attcaccctg ttaaggaaga aaccattatt aaggcacgta ataaggccgc taaagccctt      1260
caagcagtat ttgaagatct tggattacca agattactg atgaagaggt cgaagcagca      1320
acgtatgcta acaccatga tgacatgcca agcgggata tggttgcaga tatgaaggct      1380
gctcaagata tgatggatcg tggaattact gctattgata ttatcaaggc attgtacaac      1440
cacggattta agatgtcgc tgaagcaatt ttgaaccttc aaaaacaaaa agttgttggt      1500
gattaccttc aaacatcttc tattttgat aaagattgga acgtcacttc tgctgttaac      1560 gacgaaatg attatcaagg accaggtact ggataccgtc tatatgaaga caaggaagaa      1620
tgggatcgga ttaaagactt accattcgcc cttgatccag aacatttgga actgtag      1677
```

<210> SEQ ID NO 11
<211> LENGTH: 236
<212> TYPE: PRT
<213> ORGANISM: Lactobacillus reuteri

<400> SEQUENCE: 11

```
Met Ala Asp Ile Asp Glu Asn Leu Leu Arg Lys Ile Val Lys Glu Val
1               5                   10                  15

Leu Ser Glu Thr Asn Gln Ile Asp Thr Lys Ile Asp Phe Asp Lys Ser
            20                  25                  30

Asn Asp Ser Thr Ala Thr Ala Thr Gln Glu Val Gln Gln Pro Asn Ser
        35                  40                  45

Lys Ala Val Pro Glu Lys Lys Leu Asp Trp Phe Gln Pro Val Gly Glu
    50                  55                  60

Ala Lys Pro Gly Tyr Ser Lys Asp Glu Val Val Ile Ala Val Gly Pro
65                  70                  75                  80

Ala Phe Ala Thr Val Leu Asp Lys Thr Glu Thr Gly Ile Pro His Lys
                85                  90                  95

Glu Val Leu Arg Gln Val Ile Ala Gly Ile Glu Glu Gly Leu Lys
            100                 105                 110

Ala Arg Val Val Lys Val Tyr Arg Ser Ser Asp Val Ala Phe Cys Ala
        115                 120                 125

Val Gln Gly Asp His Leu Ser Gly Ser Gly Ile Ala Ile Gly Ile Gln
    130                 135                 140

Ser Lys Gly Thr Thr Val Ile His Gln Lys Asp Gln Asp Pro Leu Gly
145                 150                 155                 160

Asn Leu Glu Leu Phe Pro Gln Ala Pro Val Leu Thr Pro Glu Thr Tyr
                165                 170                 175

Arg Ala Ile Gly Lys Asn Ala Ala Met Tyr Ala Lys Gly Glu Ser Pro
            180                 185                 190

Glu Pro Val Pro Ala Lys Asn Asp Gln Leu Ala Arg Ile His Tyr Gln
        195                 200                 205

Ala Ile Ser Ala Ile Met His Ile Arg Glu Thr His Gln Val Val Val
    210                 215                 220

Gly Lys Pro Glu Glu Glu Ile Lys Val Thr Phe Asp
225                 230                 235
```

<210> SEQ ID NO 12
<211> LENGTH: 711
<212> TYPE: DNA
<213> ORGANISM: Lactobacillus reuteri

<400> SEQUENCE: 12

```
atggctgata ttgatgaaaa cttattacgt aaaatcgtta agaagttttt aagcgaaact       60
```

```
aatcaaatcg atactaagat tgactttgat aaaagtaatg atagtactgc aacagcaact      120
caagaggtgc aacaaccaaa tagtaaagct gttccagaaa agaaacttga ctggttccaa      180
ccagttggag aagcaaaacc tggatattct aaggatgaag ttgtaattgc agtcggtcct      240
gcattcgcaa ctgttcttga taagacagaa actggtattc ctcataaaga agtgcttcgt      300
caagttattg ctggtattga agaagaaggg cttaaggcgc gggtagttaa agtttaccgg      360
agttcagatg tagcattctg tgctgtccaa ggtgatcacc tttctggttc aggaattgct      420
attggtatcc aatcaaaagg gacgacagtt attcaccaaa aggatcaaga ccctcttggt      480
aaccttgagt tattcccaca gcgccagta cttactcccg aaacttatcg tgcaattggt      540
aagaatgccg ctatgtatgc taagggtgaa tctccagaac cagttccagc taaaaacgat      600
caacttgctc gtattcacta tcaagctatt tcagcaatta tgcatattcg tgaaactcac      660
caagttgttg ttggtaagcc tgaagaagaa attaaggtta cgtttgatta a              711
```

```
<210> SEQ ID NO 13
<211> LENGTH: 171
<212> TYPE: PRT
<213> ORGANISM: Lactobacillus reuteri

<400> SEQUENCE: 13

Met Ser Glu Val Asp Asp Leu Val Ala Lys Ile Met Ala Gln Met Gly
1               5                   10                  15

Asn Ser Ser Ala Asn Ser Ser Thr Gly Thr Ser Thr Ala Ser Thr
            20                  25                  30

Ser Lys Glu Met Thr Ala Asp Asp Tyr Pro Leu Tyr Gln Lys His Arg
        35                  40                  45

Asp Leu Val Lys Thr Pro Lys Gly His Asn Leu Asp Asp Ile Asn Leu
    50                  55                  60

Gln Lys Val Val Asn Asn Gln Val Asp Pro Lys Glu Leu Arg Ile Thr
65                  70                  75                  80

Pro Glu Ala Leu Lys Leu Gln Gly Glu Ile Ala Ala Asn Ala Gly Arg
                85                  90                  95

Pro Ala Ile Gln Lys Asn Leu Gln Arg Ala Ala Glu Leu Thr Arg Val
            100                 105                 110

Pro Asp Glu Arg Val Leu Glu Met Tyr Asp Ala Leu Arg Pro Phe Arg
        115                 120                 125

Ser Thr Lys Gln Glu Leu Leu Asn Ile Ala Lys Glu Leu Arg Asp Lys
    130                 135                 140

Tyr Asp Ala Asn Val Cys Ala Ala Trp Phe Glu Ala Ala Asp Tyr
145                 150                 155                 160

Tyr Glu Ser Arg Lys Lys Leu Lys Gly Asp Asn
                165                 170
```

```
<210> SEQ ID NO 14
<211> LENGTH: 516
<212> TYPE: DNA
<213> ORGANISM: Lactobacillus reuteri

<400> SEQUENCE: 14
atgagtgaag ttgatgattt agtagcaaag atcatggctc agatgggaaa cagttcatct       60
gctaatagct ctacaggtac ttcaactgca agtactagta aggaaatgac agcagatgat      120
tacccacttt atcaaaagca ccgtgattta gtaaaaacac caaaaggaca caatcttgat      180
gacatcaatt tacaaaaagt agtaaataat caagttgatc ctaaggaatt acggattaca      240
```

```
ccagaagcat tgaaacttca aggtgaaatt gcagctaatg ctggccgtcc agctattcaa    300
aagaatcttc aacgagctgc agaattaaca cgagtacctg acgaacgggt tcttgaaatg    360
tatgatgcat tgcgtccttt ccgttcaact aagcaagaat tattgaacat tgcaaaggaa    420
ttacgggaca gtatgacgc taatgtttgc gcagcatggt ttgaagaagc tgctgattat    480
tatgaaagtc gtaagaagct aaagggcgat aactaa                              516
```

<210> SEQ ID NO 15
<211> LENGTH: 184
<212> TYPE: PRT
<213> ORGANISM: Lactobacillus reuteri

<400> SEQUENCE: 15

```
Met Phe Gly His Asp Gly Arg Ile Val Thr Lys Val Tyr Gln Trp Ala
1               5                   10                  15

Gly Thr Tyr Tyr Tyr Phe Asp Pro Asn Thr Tyr Leu Arg Val Asp Asn
            20                  25                  30

Asp Tyr Arg Gln Ser Gln Trp Gly Asp Trp Tyr Met Phe Gly Pro Asp
        35                  40                  45

Gly Arg Ile Val Thr Gly Leu Lys Glu Trp Tyr Gly Ser Tyr Tyr Tyr
    50                  55                  60

Phe Asp Pro Thr Thr Tyr Leu Lys Val Thr Asn Lys Trp Ile Asp Asn
65                  70                  75                  80

Lys Tyr Phe Gly Pro Ala Gly Gln Gln Ala Ile Ser Arg Phe Glu Arg
                85                  90                  95

Leu Asp Asn Lys Tyr Tyr Phe Asp Ala Asn Gly Ala Val Leu Asn
            100                 105                 110

Ile His Asp Gln Phe Lys Asn Ile Asp Asn His Thr Tyr Tyr Phe Gly
        115                 120                 125

Ala Asp Gly Ala Cys Tyr Thr Ser Gln Phe Leu Asn Lys Asp Gly Lys
    130                 135                 140

Gln Tyr Tyr Phe Asp Asn Asp Gly Ile Met Leu Thr Asp Gln Glu Lys
145                 150                 155                 160

Ile Ile Asp Gly Lys Phe Tyr His Phe Asn Val Asn Gly Glu Ala Ile
                165                 170                 175

Gln Val Asn Asp Pro Ser Glu Ile
            180
```

<210> SEQ ID NO 16
<211> LENGTH: 555
<212> TYPE: DNA
<213> ORGANISM: Lactobacillus reuteri

<400> SEQUENCE: 16

```
atgttcggtc acgatggccg cattgttact aaagtttacc aatgggctgg cacgtattac     60
tactttgatc cgaatactta tttgcgagta gataatgatt accgtcaatc tcagtggggc    120
gattggtata tgtttggccc agatggtcgt atcgttacag ggttaaagga atggtacggt    180
agttattatt actttgatcc gacgacttac ttaaaagtaa ctaataagtg atagataat    240 aagtactttg gtccagctgg tcagcaagct atttcacgct tgagagact tgataataag    300 tattactatt tcgatgctaa tggggcagtt cttaatatcc atgatcaatt taagaatatt    360
gataaccaca cttattactt tggagctgat ggtgcttgtt ataccagtca attcttaaat    420
aaggatggta acagtatta tttcgataat gatggaatta tgctcactga tcaagagaag    480
atcattgacg gtaaattcta tcatttcaat gttaatggtg aagcaatcca agtaaatgat    540
```
ccttctgaaa tttga 555

<210> SEQ ID NO 17
<211> LENGTH: 342
<212> TYPE: PRT
<213> ORGANISM: Lactobacillus reuteri

<400> SEQUENCE: 17

Met Lys Ala Ala Val Ile Asn Asp Pro Val Asp Gly Phe Val Thr Val
1               5                   10                  15

Lys Asp Val Gln Leu Arg Asp Leu Lys Pro Gly Glu Ala Leu Val Asp
            20                  25                  30

Met Glu Tyr Cys Gly Leu Cys His Thr Asp Leu His Val Ala Ala Gly
        35                  40                  45

Asp Phe Gly Lys Lys Pro Gly Arg Ile Ile Gly His Glu Gly Val Gly
    50                  55                  60

Arg Val Ser Lys Val Ala Pro Gly Val Thr Ser Leu Lys Val Gly Asp
65                  70                  75                  80

Arg Val Ser Ile Ala Trp Phe Phe Lys Gly Cys Gly His Cys Glu Tyr
                85                  90                  95

Cys Leu Thr Gly Arg Glu Thr Leu Cys Arg Asn Val Leu Asn Ala Gly
            100                 105                 110

Tyr Thr Ala Asp Gly Ala Met Ala Glu Gln Cys Ile Val Pro Ala Asp
        115                 120                 125

Tyr Ala Val Lys Val Pro Glu Gly Leu Asp Pro Val Glu Ala Thr Ser
    130                 135                 140

Leu Thr Cys Ala Gly Val Thr Met Tyr Lys Ala Leu Lys Val Ala Asp
145                 150                 155                 160

Ile Lys Pro Gly Gln Trp Val Ser Ile Val Gly Ala Gly Gly Leu Gly
                165                 170                 175

Asn Leu Gly Ile Gln Leu Ala His Asn Val Phe Gly Ala His Val Ile
            180                 185                 190

Ala Val Asp Gly Asn Pro Asp Lys Leu Glu Ala Ala Lys Asn Gly
        195                 200                 205

Ala Glu Ile Leu Ile Asn Arg His Asp Gly Asp Val Asp Lys Gln Ile
    210                 215                 220

Gln Glu Lys Val Gly Gly Val His Ala Ala Val Val Thr Ala Val Ser
225                 230                 235                 240

Ala Ser Ala Phe Asp Gln Ala Val Asp Ser Leu Arg Pro Gly Lys
                245                 250                 255

Leu Val Ala Val Ala Leu Pro Gln Gly Asp Met Lys Leu Asn Ile Ala
            260                 265                 270

Lys Thr Val Leu Asp Gly Ile Ile Val Ala Gly Ser Leu Val Gly Thr
        275                 280                 285

Arg Gln Asp Leu Ala Glu Cys Phe Gln Phe Gly Ala Glu Gly Lys Val
    290                 295                 300

His Pro Ile Val Lys Thr Arg Lys Leu Ser Glu Ile Asn Asp Met Ile
305                 310                 315                 320

Gln Glu Leu Lys Asp Asn Lys Val Val Gly Arg Asn Val Val Asp Phe
                325                 330                 335

Val His Asn Asp Asn Asp
            340

<210> SEQ ID NO 18
<211> LENGTH: 1029
<212> TYPE: DNA

<213> ORGANISM: Lactobacillus reuteri

<400> SEQUENCE: 18

```
atgaaagctg ctgttattaa tgatccagta gacggttttg ttactgttaa agatgttcaa    60
cttcgggatt tgaagcccgg tgaagcttta gttgacatgg aatattgtgg tctttgtcac   120
actgatctac acgttgctgc tggggacttt ggtaagaagc ccggtcgtat tatcggtcac   180
gaaggggttg gtcgtgtatc taaggttgcc cctggcgtta cttccttgaa agttggcgac   240
cgtgtatcaa ttgcatggtt cttcaagggc tgtggacact gtgaatattg tttaactggt   300
cgtgaaactc tttgtcggaa cgttcttaat gcgggttaca ctgctgacgg tgcaatgggt   360
gaacaatgta tcgtaccagc tgactacgct gttaaggttc agaaggtct tgatcctgtt    420
gaagctactt cattaacttg tgctggtgtt acgatgtaca aggcattaaa ggttgctgac   480
atcaagccag gtcaatgggt atcaatcgtt ggtgctggtg gtttaggtaa cttgggtatt   540
caacttgctc acaacgtatt tggtgctcat gttatcgctg ttgatggtaa tcctgataag   600
cttgaagccg ctaagaagaa tggtgctgaa attttaatta accgtcatga cggtgatgtt   660
gataagcaaa ttcaagaaaa ggttggcggt gttcacgctg ctgtagtaac agctgtttct   720
gcctctgcat tcgaccaagc agttgattca cttcgcccag atggtaagct tgttgccgtt   780
gcgcttccac aaggtgacat gaagcttaac attgctaaga ctgttcttga tggtatcatt   840
gttgctggtt cattagttgg tacccgtcaa gacttagctg aatgtttcca atttggtgca   900
gaaggtaagg ttcacccaat tgttaagact cgtaagttaa gcgaaattaa tgatatgatc   960
caagaactta aggataacaa ggttgttggt cggaatgttg ttgattttgt tcacaacgat  1020
aacgactaa                                                         1029
```

<210> SEQ ID NO 19
<211> LENGTH: 348
<212> TYPE: PRT
<213> ORGANISM: Lactobacillus reuteri

<400> SEQUENCE: 19

```
Met Glu Lys Arg Glu Asn Ala Ile Pro Lys Thr Met Lys Ala Trp Ala
1               5                   10                  15

Val Thr Thr Pro Gly Pro Ile Asp Gly Lys Glu Ser Pro Ile Glu Phe
            20                  25                  30

Thr Glu Lys Pro Val Pro Thr Pro Lys Arg Gly Glu Val Leu Val Lys
        35                  40                  45

Val Ile Thr Cys Gly Val Cys His Thr Asp Leu His Val Thr Glu Gly
    50                  55                  60

Asp Leu Pro Val His His Glu His Val Thr Pro Gly His Glu Ile Val
65                  70                  75                  80

Gly Lys Val Val Gly Phe Gly Pro Glu Thr Gln Arg Phe Lys Phe Gly
                85                  90                  95

Glu Arg Ile Gly Ile Pro Trp Phe Arg His Ala Cys Gly Val Cys Lys
            100                 105                 110

Phe Cys Arg Ser Gly His Glu Asn Leu Cys Pro His Ser Leu Tyr Thr
        115                 120                 125

Gly Trp Asp His Asp Gly Gly Tyr Ala Glu Tyr Val Thr Val Pro Glu
    130                 135                 140

Gly Phe Ala Tyr Arg Leu Pro Glu Lys Phe Asp Ser Leu Glu Ala Ala
145                 150                 155                 160

Pro Leu Leu Cys Ala Gly Ile Ile Gly Tyr Arg Ala Phe Glu Arg Ala
                165                 170                 175
```

Asn Val Pro Ala Gly Gly Arg Leu Gly Leu Tyr Gly Phe Gly Gly Ser
            180                 185                 190

Ala His Ile Thr Ala Gln Ile Ala Leu Ala Gln Gly Ile Glu Val His
            195                 200                 205

Val Phe Thr Arg Gly Glu Asp Ala Lys Lys Phe Ala Leu Glu Leu Gly
            210                 215                 220

Cys Ala Ser Val Gln Gly Ser Tyr Asp Pro Ala Pro Val Pro Leu Asp
225                 230                 235                 240

Ser Ser Ile Ile Phe Ala Pro Val Gly Asp Met Val Leu Pro Ala Leu
                245                 250                 255

Ala Ser Leu Val Pro Gly Gly Thr Leu Ala Leu Ala Gly Ile His Met
            260                 265                 270

Thr Asp Ile Pro Thr Met Asn Tyr Gln Lys Glu Ile Phe His Glu Lys
            275                 280                 285

Thr Leu Thr Ser Val Glu Ser Asn Thr Arg Arg Asp Gly Glu Glu Phe
            290                 295                 300

Leu Thr Leu Ala Asp Arg Leu Asn Ile His Pro Glu Val His Glu Tyr
305                 310                 315                 320

Pro Leu Ala Lys Ala Asp Glu Ala Leu Arg Tyr Val Lys His Gly Asp
                325                 330                 335

Ile Lys Gly Ala Cys Val Leu Arg Val Ser Glu Asp
            340                 345

<210> SEQ ID NO 20
<211> LENGTH: 1047
<212> TYPE: DNA
<213> ORGANISM: Lactobacillus reuteri

<400> SEQUENCE: 20
atggaaaaac gcgaaaatgc tattccgaaa acaatgaagg cttgggcagt cacaactcct      60
gggccgattg atggtaagga atcaccaatc gaatttaccg aaaagcctgt gccgactcct     120
aaacggggag aagtccttgt taaggtaata acgtgtggag tatgtcatac ggacttgcac     180
gtgactgaag gagacttgcc ggttcaccac gaacacgtta ctcctggtca tgaaattgtt     240
ggtaaagttg tcggctttgg accagagaca caacgattta gtttggtga gcgaattggg     300
attccatggt ttcggcatgc ttgtggtgta tgcaagtttt gccgatcagg tcatgagaat     360
ctctgtcctc attcacttta taccggttgg gatcatgatg gcggttatgc agaatatgtc     420
acagttccag aaggatttgc atatcggctt ccagaaaagt ttgattccct agaggcagct     480
ccgttattat gtgcagggat tattggttat cgggcctttg aacgtgccaa tgttccggct     540
ggcggtcgcc taggattata tggcttcggt ggttcagctc atattacagc tcaaattgca     600
cttgctcagg gaattgaagt gcatgtcttt acgcgtggtg aggatgccaa gaaattcgcc     660
ctagaattag ttgtgcttc tgttcagggc tcctatgacc cagcaccagt tcctttggat     720
tcatcaatca tttttgcgcc ggttggtgat atggtcttgc cggctttagc tagtttagtt     780
ccaggggga cattagcatt agccggtatt catatgactg atattccaac aatgaattac     840
caaaaagaaa tattccacga aaagacatta acgagtgttg agagtaatac tcgtcgtgat     900
ggggaagaat tcttaacatt agctgatcgt cttaatatcc atcctgaagt ccacgaatat     960
cccctagcaa aggctgacga agcattacgc tatgttaagc acggtgatat taagggagct    1020
tgtgtattac gtgttagtga ggactaa                                         1047

<210> SEQ ID NO 21

<211> LENGTH: 486
<212> TYPE: PRT
<213> ORGANISM: Lactobacillus reuteri

<400> SEQUENCE: 21

```
Met Gln Ile Lys Ala Ala Leu Ala Thr Lys Pro Asn Ala Asp Leu Glu
1               5                   10                  15

Ile Gln Thr Val Glu Leu Asp Glu Pro Lys Glu Asn Glu Val Leu Ile
            20                  25                  30

Lys Ile Ala Ser Thr Gly Phe Cys His Thr Asp Ile Val Gly Arg Ser
        35                  40                  45

Gly Ala Thr Thr Pro Leu Pro Val Val Leu Gly His Glu Gly Ala Gly
    50                  55                  60

Val Val Gln Lys Val Gly Ala Asn Val Thr Asp Val Lys Pro Gly Asp
65                  70                  75                  80

His Val Val Leu Ser Phe Ser Tyr Cys Gly His Cys Tyr Asn Cys Thr
                85                  90                  95

His Asn His Gln Gly Leu Cys Glu Asn Phe Asn Gln Leu Asn Phe Glu
            100                 105                 110

Gly Lys Thr Tyr Asp Gly Thr His Arg Leu His Leu Asp Asp Gly Thr
        115                 120                 125

Pro Val Ser Val Phe Phe Gly Gln Ser Ser Phe Ala Thr Tyr Val Thr
    130                 135                 140

Ala Asn Val His Asn Ile Val Lys Val Asp Gln Asp Val Asp Leu Asn
145                 150                 155                 160

Leu Leu Gly Pro Leu Gly Cys Gly Met Gln Thr Gly Ala Gly Thr Val
                165                 170                 175

Leu Asn Tyr Ile Lys Pro Ala Pro Glu Asp Ala Ile Ala Val Phe Gly
            180                 185                 190

Ala Gly Ala Val Gly Leu Ala Ala Ile Met Ala Ala Lys Ile Ala Gly
        195                 200                 205

Val Lys His Ile Ile Ala Ile Asn Arg Asn Gly Asn His Leu Asp Leu
    210                 215                 220

Ala Lys Glu Leu Gly Ala Thr Glu Thr Ile Asn Asn Thr Ala Glu Asp
225                 230                 235                 240

Pro Val Lys Ala Ile Lys Glu Ile Val Pro Arg Gly Val Thr Tyr Ala
                245                 250                 255

Ile Asp Thr Thr Gly Asn Thr Gly Val Ile Lys Ser Ala Ile Asp Ser
            260                 265                 270

Leu Ala Thr Ala Gly Glu Cys Val Leu Gly Val Gly Gly Asp Ile
        275                 280                 285

Thr Leu Asp Leu Met Asn Asp Ile Leu Ser Glu Ser Lys Lys Ile Ser
    290                 295                 300

Gly Val Val Glu Gly Asp Ser Asn Pro Gln Glu Phe Ile Pro Gln Leu
305                 310                 315                 320

Val Lys Tyr Tyr Lys Gln Ser Lys Phe Pro Leu Asp Lys Leu Val Lys
                325                 330                 335

Tyr Tyr Asp Phe Ala Asp Ile Asn Gln Val Ile Ala Asp Ser Thr Asn
            340                 345                 350

Gly Lys Val Ile Lys Pro Ile Lys Ile Asp Pro Glu Leu Ala Lys
        355                 360                 365

Leu Pro Leu Thr Asn Asp Gly Ser Asn Val Gln Lys Met Val Ala Glu
    370                 375                 380

Ala Gly Leu Ala Asp Gln Ile Thr Ile Asp Ser Ala Gly Thr Ser Asn
385                 390                 395                 400
```

Ile Ala Glu Gly Ser Pro Ala Asp Ser Arg Thr Lys Ala Ile Leu Asp
            405                 410                 415

Lys Tyr His Ile Lys Asp Asp Gly Met Ile Ala Arg Gln Leu Gln Asp
        420                 425                 430

Arg Asp Tyr Tyr Asp Ala Asp Tyr Ile Ile Ala Met Asp Gln Met Asn
    435                 440                 445

Val Arg Asp Ala Lys Asp Met Ala Pro Ala Gly Leu Glu Asn Lys Val
450                 455                 460

His Gly Ile Phe Glu Ala Thr Pro Gly Lys Glu Asn Cys Tyr Ile Val
465                 470                 475                 480

Asp Pro Trp Ile Thr His
            485

<210> SEQ ID NO 22
<211> LENGTH: 1464
<212> TYPE: DNA
<213> ORGANISM: Lactobacillus reuteri

<400> SEQUENCE: 22

```
atgcaaatta aagctgctct tgcaaccaaa cctaacgctg atttagagat tcaaaccgtc      60
gaattggatg aaccaaaaga aatgaagta ttaataaaaa ttgcttcaac aggttttgt      120
catacagata ttgttggtcg aagcggtgcc actacccctc tccccgttgt cctcgggcat     180
gaaggtgcgg gcgtcgtcca aaaagtagga gctaacgtta cggacgttaa acccggcgac    240
catgttgttc tatcatttag ctactgtggc cattgctata actgtactca taatcatcaa    300
ggcttatgcg aaaacttcaa tcagctaaac tttgaaggaa aaacctatga tggtactcac    360
cgcctgcact agatgatgg cacgccagtc agtgtctttt ttggtcagtc ttcctttgcg    420
acctatgtaa cagccaatgt ccataatatt gttaaagttg atcaagatgt tgatcttaac    480
ttattagggc cactcggttg tggaatgcaa acaggtgctg gaaccgttct aaattatatt    540
aaacctgctc ctgaagatgc aattgccgtt tcggtgctg gtgctgttgg cttagccgca    600
attatggctg ctaaaattgc tggagttaaa catattattg cgattaatcg taacggtaac    660
caccttgacc tggcgaagga attgggcgct actgaaacga ttaataatac ggctgaagat    720
cccgtcaaag caattaaaga aatcgttccg cgtggtgtaa cttatgcaat cgatactacc    780
ggaaacaccg gtgtaattaa atcagcaatt gatagtcttg ccaccgctgg agaatgtgtc    840
ctcttaggag ttggcggcga tattaccttg acttaatga atgatatctt atcagaatct    900
aagaaaatct ctggggttgt cgaaggagat agcaatcccc aagagtttat tcctcaacta    960
gttaagtact acaagcaaag caagttcccc cttgataagc ttgttaagta ctacgatttt   1020
gctgatatta ccaagttat cgctgactca acaaacggaa aggttattaa gccaatcatc   1080
aaaattgatc ctgaattagc taaataattg ccgctcacca atgacggaag caatgttcaa   1140
aaaatggttg cagaagctgg ccttgctgat caaattacta ttgattcagc cggaacaagt   1200
aacattgcag aaggttcacc tgctgatagt cgaacaaaag ccattctcga taaatatcac   1260
attaaagacg acggaatgat tgcccgtcaa ttgcaggaca gggattatta tgatgccgat   1320
tatattatcg caatggatca gatgaatgtc cgggacgcaa agatatggc accagctggg    1380
ttagaaaata aggttcatgg aatctttgaa gctaccccag gaaaagaaaa ttgctatatc   1440
gttgaccct ggatcactca ctga                                             1464
```

<210> SEQ ID NO 23
<211> LENGTH: 351

```
<212> TYPE: PRT
<213> ORGANISM: Lactobacillus reuteri

<400> SEQUENCE: 23

Met Lys Lys Ala Ile Phe Glu Lys Ala Gly Gln Met Lys Ile Val Asp
1               5                   10                  15

Val Asp Arg Pro Thr Ile Glu Lys Pro Asp Asp Val Ile Ile Lys Val
            20                  25                  30

Val Arg Thr Cys Val Cys Gly Ser Asp Leu Trp Asn Phe Arg Gly Ile
        35                  40                  45

Asn Pro Val Glu Lys Asp Ser Glu Asn Ser Gly His Glu Ala Ile Gly
    50                  55                  60

Ile Val Glu Glu Val Gly Glu Asp Ile Thr Thr Val Lys Pro Gly Asp
65                  70                  75                  80

Phe Val Ile Ala Pro Phe Thr His Gly Cys Gly His Cys Ala Ala Cys
                85                  90                  95

Arg Ala Gly Phe Asp Gly Ser Cys Gln Ser His Asn Asp Asn Phe Ser
            100                 105                 110

Ser Gly Val Gln Ala Gln Tyr Val Arg Phe Gln His Gly Gln Trp Ala
        115                 120                 125

Leu Val Lys Val Pro Gly Lys Pro Ser Asp Tyr Ser Glu Gly Met Leu
    130                 135                 140

Lys Ser Leu Leu Thr Leu Ala Asp Val Met Ala Thr Gly Tyr His Ala
145                 150                 155                 160

Ala Arg Val Ala Asn Val Ser Asp Gly Asp Thr Val Val Val Met Gly
                165                 170                 175

Asp Gly Ala Val Gly Leu Cys Ala Ile Ile Ala Ala Lys Met Arg Gly
            180                 185                 190

Ala Lys Lys Ile Ile Ser Thr Ser Arg His Ala Asp Arg Gln Ala Leu
        195                 200                 205

Ala Lys Glu Phe Gly Ala Thr Asp Asn Val Ala Glu Arg Ser Asp Glu
    210                 215                 220

Ala Val Gln Lys Ile Met Glu Leu Thr Asn Gly Ala Gly Ala Asp Ala
225                 230                 235                 240

Val Leu Glu Cys Val Gly Thr Glu Gln Ser Thr Asp Thr Ala Met Lys
                245                 250                 255

Val Gly Arg Pro Gly Thr Ile Val Gly Arg Val Gly Leu Pro His Thr
            260                 265                 270

Pro Lys Met Asp Met Thr Val Leu Phe Tyr Asn Asn Thr Ile Val Gly
        275                 280                 285

Gly Gly Pro Ala Ser Val Thr Thr Tyr Asp Lys Asp Val Leu Leu Lys
    290                 295                 300

Ala Val Leu Asp Gly Asp Ile Asn Pro Gly Lys Val Phe Thr Lys Ser
305                 310                 315                 320

Phe Asp Leu Asp Gln Ile Gln Glu Ala Tyr Gly Ala Met Asp Lys Arg
                325                 330                 335

Glu Ala Ile Lys Ser Tyr Ile Ile Met Asp Gly Phe Glu Arg Asp
            340                 345                 350

<210> SEQ ID NO 24
<211> LENGTH: 1056
<212> TYPE: DNA
<213> ORGANISM: Lactobacillus reuteri

<400> SEQUENCE: 24
atgaaaaaag ctattttga aaaggcgggt caaatgaaga ttgttgatgt tgaccgtcca      60
```

```
acaattgaaa agcctgatga cgtaattatt aaggtagtgc ggacctgtgt ttgtggttct    120
gacctatgga acttccgagg aattaatccg gttgaaaaag attctgaaaa ctctggccat    180
gaagcaattg gaattgttga agaagttggt gaagatatca ctactgtcaa acctggggac    240
tttgtgattg ctccatttac tcatggatgt gggcactgtg ctgcttgtcg cgcgggcttc    300
gatggttctt gccaaagtca acgataac tttagctctg gtgtgcaagc tcaatacgtt    360
cggttccaac acggtcaatg ggcgcttgtt aaagttccgg gcaagccaag tgactacagt    420
gaaggaatgc ttaagtccct cttaacccttt gctgatgtta tggctactgg ttaccacgct    480
gcacgagttg ctaacgttag tgatggtgat acagttgttg taatgggtga cggtgctgtt    540
ggcctttgtg cgattattgc tgctaagatg cggggcgcta agaagatcat ttctactagt    600
cgccatgctg accgtcaagc ccttgctaag gaatttggtg ctactgacaa tgttgctgaa    660
cgtagtgacg aagcggttca aaagatcatg gaactcacta acggtgccgg tgctgatgct    720
gtccttgaat gcgttggtac tgaacaatca actgatactg ccatgaaagt tggccgtcca    780
ggtaccatcg ttggtcgggt tggcttacct cataccccaa agatggacat gacggtgcta    840
ttctacaaca cactattgt cggcggtggt ccagcatcag taaccactta cgacaaggac    900
gtattgttga aggctgttct tgatggtgac attaaccctg gtaaggtctt tactaagagc    960
ttcgaccttg accaaattca gaagcttat gaagcaatgg ataagcgtga agcaatcaag    1020
tcttacatta ttatggatgg ctttgaacgc gattaa                             1056
```

```
<210> SEQ ID NO 25
<211> LENGTH: 251
<212> TYPE: PRT
<213> ORGANISM: Lactobacillus reuteri

<400> SEQUENCE: 25

Met Gly Arg Leu Asp Asn Lys Val Ala Ile Ile Thr Gly Gly Ser Lys
1               5                   10                  15

Gly Ile Gly Ala Ala Val Ala Lys Lys Phe Ile Glu Glu Gly Ala Lys
            20                  25                  30

Val Val Leu Thr Ala Arg Lys Met Asp Glu Gly Gln Lys Val Ala Asp
        35                  40                  45

Gln Leu Gly Asp Asn Ala Ile Phe Ile Gln Gln Asp Val Ala Arg Lys
    50                  55                  60

Gly Asp Trp Asp Arg Val Ile Arg Gln Thr Val Gln Val Phe Gly Lys
65                  70                  75                  80

Leu Asn Ile Val Val Asn Asn Ala Gly Ile Ala Glu Tyr Ala Asp Val
                85                  90                  95

Glu Lys Thr Asp Ala Glu Ile Trp Asp Lys Thr Ile Ala Val Asn Leu
            100                 105                 110

Thr Gly Thr Met Trp Gly Thr Lys Leu Gly Ile Glu Ala Met Lys Asn
        115                 120                 125

Asn Gly Glu Lys Asn Ser Ile Ile Asn Met Ser Ser Ile Glu Gly Leu
    130                 135                 140

Ile Gly Asp Pro Asp Leu Phe Ala Tyr Asn Ala Ser Lys Gly Gly Val
145                 150                 155                 160

Arg Leu Leu Thr Lys Ser Ala Ala Leu Asp Cys Ala Arg Lys Gly Tyr
                165                 170                 175

Asp Ile Arg Val Asn Thr Ile His Pro Gly Tyr Ile Ser Thr Pro Leu
            180                 185                 190

Val Asp Asn Leu Val Lys Asp Asp Pro Lys Ala Glu Gly His Leu Glu
```

```
            195                 200                 205
Ser Leu His Pro Leu Gly Arg Leu Gly Lys Pro Glu Glu Ile Ala Asn
    210                 215                 220

Leu Ala Leu Tyr Leu Ala Ser Asp Glu Ser Ser Phe Ser Thr Gly Ser
225                 230                 235                 240

Glu Phe Val Ala Asp Gly Gly Tyr Thr Ala Gln
                245                 250

<210> SEQ ID NO 26
<211> LENGTH: 756
<212> TYPE: DNA
<213> ORGANISM: Lactobacillus reuteri

<400> SEQUENCE: 26
atgggtcgtt tagataataa agttgcaatt attactggtg ttctaaagg aattggagct      60 gctgtcgcaa aaagtttat cgaagaaggc gcaaaggttg ttttaaccgc tcggaagatg     120 gatgaggac aaaaagtcgc tgaccaacta ggtgacaatg cgatctttat ccaacaagac     180
gttgctcgga aggagactg ggaccgggta atccgccaaa ctgtccaagt ctttgggaag     240
ctcaatattg tggttaacaa tgcgggaatt gccgaatacg ccgatgttga aagacggac     300 gctgaaattt gggataaaac aattgccgtt aaccttaccg gtacgatgtg gggaactaag    360
ctcggtattg aagcaatgaa gaacaacggg gaaaagaatt caatcatcaa tatgtcatcc    420
attgaaggac taattggtga tcctgatctc tttgcataca atgcttctaa gggtggtgtc    480
cgcctcttaa ctaagtccgc tgcgcttgat tgtgcccgga aaggctatga catccgtgta    540
aatacaattc atcctggtta tatctcaact ccactagttg ataatttggt caaggatgat    600
ccaaaagcag aaggacacct agaaagcctt catcccttg gccgtcttgg aaagccagaa     660
gagattgcta acctcgcttt ataccttgct tcagatgaat caagctttag tactggttcg    720
gaatttgtcg ctgatggtgg ctatacggct caataa                              756

<210> SEQ ID NO 27
<211> LENGTH: 292
<212> TYPE: PRT
<213> ORGANISM: Lactobacillus reuteri

<400> SEQUENCE: 27

Met Thr Asn Val Pro Thr Val Lys Leu Asn Asn Gly Val Glu Met Pro
1               5                   10                  15

Thr Leu Gly Phe Glu Val Phe Gln Val Pro Asp Leu Ser Gln Ala Glu
                20                  25                  30

Gln Ala Val Thr Asp Ala Leu Glu Val Gly Tyr Arg Leu Ile Asp Thr
            35                  40                  45

Ala Ala Ala Tyr Gln Asn Glu Glu Ala Val Gly Lys Ala Ile Lys Asn
        50                  55                  60

Ser Ser Val Asn Arg Glu Asp Val Phe Val Thr Ser Lys Leu Trp Val
65                  70                  75                  80

Ser Asp Phe Asn Tyr Lys Arg Ala Lys Ala Gly Ile Asp Ala Ser Leu
                85                  90                  95

Gln Lys Leu Gly Leu Asp Tyr Met Asp Leu Tyr Leu His Gln Pro
            100                 105                 110

Tyr Gly Asp Thr Met Gly Ala Trp Arg Ala Leu Gln Glu Ala Gln Lys
        115                 120                 125

Glu Gly Lys Ile Arg Ala Ile Gly Val Ser Asn Phe Tyr Ala Asp Gln
    130                 135                 140
```

```
Leu Lys Asp Leu Glu Leu Thr Met Pro Val Lys Pro Ala Val Asn Gln
145                 150                 155                 160

Ile Glu Val Asn Pro Trp Tyr Gln Gln Asp Gln Glu Val Lys Phe Ala
                165                 170                 175

Gln Ser Glu Asp Ile Arg Val Glu Ala Trp Ala Pro Phe Ala Glu Gly
            180                 185                 190

Lys His Asp Ile Phe Thr Asn Glu Ile Ala Glu Ile Ala Ala Lys
        195                 200                 205

Tyr Gly Lys Ser Asn Gly Gln Val Ile Leu Arg Trp Leu Leu Gln Arg
    210                 215                 220

Gly Ile Thr Val Ile Pro Lys Ser Val His Lys Asn Arg Met Glu Glu
225                 230                 235                 240

Asn Ile Asp Val Phe Asp Phe Glu Leu Ser Asn Asp Met Lys Lys
                245                 250                 255

Ile Ala Ser Leu Asn Lys Lys Glu Ser Gln Phe Phe Asp His Arg Asp
                260                 265                 270

Pro Val Thr Ile Glu Gln Ile Phe Gly Ser Ser Leu Lys Met Val Gln
                275                 280                 285

Asp Asp Glu Lys
    290
```

```
<210> SEQ ID NO 28
<211> LENGTH: 879
<212> TYPE: DNA
<213> ORGANISM: Lactobacillus reuteri

<400> SEQUENCE: 28
atgacaaatg taccaacagt aaaattaaat aacggagtag aaatgccaac ccttggattt      60
gaagtattcc aagttccaga cttaagccaa gctgaacaag cagttaccga tgctcttgaa     120
gtcggctatc gtttaatcga tactgctgct gcttaccaaa atgaagaagc agttggaaag     180
gcaattaaga atagtagtgt aaaccgtgaa gatgtctttg taacttctaa gttatgggtg     240
tctgatttta actataagcg ggctaaagca gggattgacg cttcactgca aaaacttggc     300
cttgattaca tggatcttta ccttctccat caaccatatg gcgatacaat gggggcttgg     360
cgagcattac aagaagcaca gaaagaaggt aagattcgcg caatcggtgt atcgaacttc     420
tacgctgatc aactaaagga tcttgaatta acaatgcctg ttaagccagc ggtcaaccaa     480
attgaagtta acccttggta ccagcaagat caagaggtta agtttgcgca aagtgaagat     540
attcgtgttg aagcatgggc accatttgcg gaaggtaagc atgatatttt taccaacgaa     600
ataattgcgg aaattgctgc caagtatggc aagagcaatg gtcaagtaat tcttcgctgg     660
cttttacaac ggggtattac tgtcattcca aagtcagtcc acaagaaccg gatggaagaa     720
aatatcgatg tctttgattt tgaactttcc aatgatgata tgaaaaagat agctagtctt     780
aacaagaagg aaagccaatt ctttgaccac cgtgatccgg ttacgattga acaaatcttt     840
ggctccagct taaagatggt tcaagatgac gaaaaataa                            879
```

```
<210> SEQ ID NO 29
<211> LENGTH: 287
<212> TYPE: PRT
<213> ORGANISM: Lactobacillus reuteri

<400> SEQUENCE: 29

Met Ile Leu Asp Glu Thr Ile Thr Leu Asn Ser Gly Val Lys Ile Pro
1               5                   10                  15

Lys Phe Ala Leu Gly Thr Trp Met Ile Asp Asp Gln Ala Ala Glu
```

|  | 20 | | | | 25 | | | | 30 | | |
|---|---|---|---|---|---|---|---|---|---|---|---|
Ala Val Arg Asn Ala Ile Lys Met Gly Tyr Arg His Ile Asp Thr Ala
          35                  40                  45

Gln Ala Tyr Asp Asn Glu Arg Gly Val Gly Glu Gly Val Arg Thr Ala
     50                  55                  60

Gly Ile Asp Arg Asp Lys Ile Phe Val Thr Ser Lys Ile Ala Ala Glu
65                  70                  75                  80

His Lys Asp Tyr Asp Val Thr Lys Lys Ser Ile Asp Glu Thr Leu Glu
                85                  90                  95

Lys Met Gly Leu Asp Tyr Ile Asp Met Met Leu Ile His Ser Pro Gln
            100                 105                 110

Pro Trp Lys Glu Val Asn Gln Ser Asp Asn Arg Tyr Leu Glu Gly Asn
        115                 120                 125

Leu Ala Ala Trp Arg Ala Met Glu Asp Ala Val Asn Glu Gly Lys Ile
    130                 135                 140

Arg Thr Ile Gly Val Ser Asn Phe Lys Lys Ala Asp Leu Glu Asn Ile
145                 150                 155                 160

Ile Lys Asn Ser Asp Thr Val Pro Ala Val Asp Gln Val Leu Ala His
                165                 170                 175

Ile Gly His Thr Pro Phe Asn Leu Leu Ser Phe Thr His Glu His Asp
            180                 185                 190

Ile Ala Val Glu Ala Tyr Ser Pro Val Ala His Gly Ala Ala Leu Asp
        195                 200                 205

Asn Pro Val Ile Glu Lys Met Ala Lys Lys Tyr Asn Val Ser Val Pro
    210                 215                 220

Gln Leu Cys Ile Arg Tyr Asp Trp Gln Ile Gly Met Ile Val Leu Pro
225                 230                 235                 240

Lys Thr Thr Asn Pro Glu His Met Lys Glu Asn Thr Glu Ile Asp Phe
                245                 250                 255

Glu Ile Ser Glu Ala Asp Met Asp Leu Leu Arg Arg Val Lys Pro Leu
            260                 265                 270

Asp Tyr Gly Asp Phe Asp Ile Tyr Pro Val Tyr Gly Gly Lys Met
        275                 280                 285

<210> SEQ ID NO 30
<211> LENGTH: 864
<212> TYPE: DNA
<213> ORGANISM: Lactobacillus reuteri

<400> SEQUENCE: 30
atgattttag atgagacaat tactcttaat agtggtgtga aaattccaaa gtttgcatta    60
ggaacctgga tgattgatga tgaccaagca gccgaagcag ttcggaatgc gattaagatg   120
ggatatcggc acatcgatac agctcaggct tatgataatg agcggggagt cggtgaaggt   180
gtacgaacag ccggtattga tcgggataaa atctttgtta cttcaaagat cgctgctgaa   240
cacaaagatt atgatgtaac taaaaagtcg attgacgaga ctcttgaaaa gatgggtctt   300
gattatatcg acatgatgct tattcatagt cctcaaccat ggaaagaagt aaatcaatct   360
gataatcgtt accttgaagg aaatctcgct gcttggcgag ccatggaaga tgccgttaac   420
gaaggtaaga ttcgaacaat tggcgtttct aatttcaaaa aagccgatct tgaaaatatt   480
attaagaata gcgataccgt tccgctgttg atcaagttta gctcatatat ggtcatact   540 ccattcaatc ttttatcatt tactcatgaa catgacattg cggttgaagc atattccaca   600
gttgctcacg gcgctgcttt agacaacccc gtaattgaaa agatggctaa aaagtacaac   660

```
gtttcagtcc cacaattgtg cattcggtat gattggcaaa taggaatgat cgtcttacca    720
aagactacta atccagaaca catgaaggaa aacactgaaa ttgattttga aatttctgaa    780
gctgatatgg acctattgcg gcgagtaaag ccattagact atggcgattt tgatatctac    840
cctgtttacg gtggaaaaat gtaa                                          864
```

<210> SEQ ID NO 31
<211> LENGTH: 878
<212> TYPE: PRT
<213> ORGANISM: Lactobacillus reuteri

<400> SEQUENCE: 31

```
Met Pro Ala Asn Asn Lys Lys Gln Val Glu Lys Lys Glu Leu Thr Ala
1               5                   10                  15

Glu Glu Lys Lys Gln Asn Ala Gln Lys Leu Val Asp Asp Leu Met Thr
            20                  25                  30

Lys Ser Gln Ala Ala Phe Glu Lys Leu Arg Tyr Tyr Ser Gln Glu Gln
        35                  40                  45

Val Asp Lys Ile Cys Gln Ala Met Ala Leu Ala Ala Glu Glu His His
    50                  55                  60

Met Asp Leu Ala Val Asp Ala Ala Asn Glu Thr Gly Arg Gly Val Ala
65                  70                  75                  80

Glu Asp Lys Ala Ile Lys Asn Ile Tyr Ala Ser Glu Tyr Ile Trp Asn
                85                  90                  95

Asn Ile Arg His Asp Lys Thr Val Gly Ile Ile Glu Asp Asn Asp Glu
            100                 105                 110

Asp Gln Thr Ile Lys Ile Ala Asp Pro Leu Gly Val Ile Ala Gly Ile
        115                 120                 125

Val Pro Val Thr Asn Pro Thr Ser Thr Thr Ile Phe Lys Ser Ile Ile
    130                 135                 140

Ser Ala Lys Thr Arg Asn Thr Ile Ile Phe Ser Phe His Arg Gln Ala
145                 150                 155                 160

Met Lys Ser Ser Ile Lys Thr Ala Lys Ile Leu Gln Glu Ala Ala Glu
                165                 170                 175

Lys Ala Gly Ala Pro Lys Asn Met Ile Gln Trp Leu Pro Glu Ser Thr
            180                 185                 190

Arg Glu Asn Thr Thr Ala Leu Leu Gln His Pro Asn Thr Ala Thr Ile
        195                 200                 205

Leu Ala Thr Gly Gly Pro Ser Leu Val Lys Ala Ala Tyr Ser Ser Gly
    210                 215                 220

Asn Pro Ala Leu Gly Val Gly Pro Gly Asn Gly Pro Ala Tyr Ile Glu
225                 230                 235                 240

Lys Thr Ala Asn Ile Glu Arg Ser Val Tyr Asp Ile Val Leu Ser Lys
                245                 250                 255

Thr Phe Asp Asn Gly Met Ile Cys Ala Thr Glu Asn Ser Val Val Val
            260                 265                 270

Asp Glu Glu Ile Tyr Asp Lys Val Lys Glu Glu Phe Gln Lys Trp Asn
        275                 280                 285

Cys Tyr Phe Leu Lys Pro Asn Glu Ile Asp Lys Phe Thr Asp Gly Phe
    290                 295                 300

Ile Asp Pro Asp Arg His Gln Val Arg Gly Pro Ile Ala Gly Arg Ser
305                 310                 315                 320

Ala Asn Ala Ile Ala Asp Met Cys Gly Ile Lys Val Pro Asp Asn Thr
                325                 330                 335

Lys Val Ile Ile Ala Glu Tyr Glu Gly Val Gly Asp Lys Tyr Pro Leu
```

```
                340             345             350
Ser Ala Glu Lys Leu Ser Pro Val Leu Thr Met Tyr Lys Ala Thr Ser
        355                 360                 365

His Glu Asn Ala Phe Asp Ile Cys Ala Gln Leu Leu His Tyr Gly Gly
    370                 375                 380

Glu Gly His Thr Ala Ala Ile His Thr Leu Asp Asp Leu Ala Thr
385                 390                 395                 400

Lys Tyr Gly Leu Glu Met Arg Ala Ser Arg Ile Ile Val Asn Ser Pro
                405                 410                 415

Ser Gly Ile Gly Gly Ile Gly Asn Ile Tyr Asn Asn Met Thr Pro Ser
            420                 425                 430

Leu Thr Leu Gly Thr Gly Ser Tyr Gly Ser Asn Ser Ile Ser His Asn
        435                 440                 445

Val Thr Asp Trp Asp Leu Leu Asn Ile Lys Thr Ile Ala Lys Arg Arg
    450                 455                 460

Glu Asn Arg Gln Trp Val Lys Ile Pro Pro Lys Val Tyr Phe Gln Arg
465                 470                 475                 480

Asn Ser Leu Lys Glu Leu Gln Asp Ile Pro Asn Ile Asn Arg Ala Phe
                485                 490                 495

Ile Val Thr Gly Pro Gly Met Ser Lys Arg Gly Tyr Val Gln Arg Val
            500                 505                 510

Ile Asp Gln Leu Arg Gln Arg Gln Asn Asn Thr Ala Phe Leu Val Phe
        515                 520                 525

Asp Asp Val Glu Glu Asp Pro Ser Thr Asn Thr Val Glu Lys Gly Val
    530                 535                 540

Ala Met Met Asn Asp Phe Lys Pro Asp Thr Ile Ile Ala Leu Gly Gly
545                 550                 555                 560

Gly Ser Pro Met Asp Ala Ala Lys Ala Met Trp Met Phe Tyr Glu His
                565                 570                 575

Pro Glu Thr Ser Trp Tyr Gly Val Met Gln Lys Tyr Leu Asp Ile Arg
            580                 585                 590

Lys Arg Ala Tyr Gln Ile Lys Lys Pro Thr Lys Ser Gln Leu Ile Gly
        595                 600                 605

Ile Pro Thr Thr Ser Gly Thr Gly Ser Glu Val Thr Pro Phe Ala Val
    610                 615                 620

Ile Thr Asp Ser Lys Thr His Val Lys Tyr Pro Leu Ala Asp Tyr Ala
625                 630                 635                 640

Leu Thr Pro Asn Ile Ala Ile Val Asp Ser Gln Phe Val Glu Thr Val
                645                 650                 655

Pro Ala Lys Thr Thr Ala Trp Thr Gly Leu Asp Val Leu Cys His Ala
            660                 665                 670

Thr Glu Ser Tyr Val Ser Val Met Ala Thr Asp Tyr Thr Arg Gly Trp
        675                 680                 685

Ser Leu Gln Thr Ile Lys Gly Val Met Glu Asn Leu Pro Lys Ser Val
    690                 695                 700

Gln Gly Asp Lys Leu Ala Arg Arg Lys Met His Asp Phe Ser Thr Met
705                 710                 715                 720

Ala Gly Met Ala Phe Gly Gln Ala Phe Leu Gly Ile Asn His Ser Leu
                725                 730                 735

Ala His Lys Met Gly Gly Ala Phe Gly Leu Pro His Gly Leu Leu Ile
            740                 745                 750

Ala Ile Ala Met Pro Gln Val Ile Arg Phe Asn Ala Lys Arg Pro Gln
        755                 760                 765
```

```
Lys Leu Ala Leu Trp Pro His Tyr Glu Thr Tyr His Ala Thr Lys Asp
        770                 775                 780

Tyr Ala Asp Ile Ala Arg Phe Ile Gly Leu Lys Gly Asn Thr Asp Glu
785                 790                 795                 800

Glu Leu Ala Glu Ala Tyr Ala Lys Lys Val Ile Glu Leu Ala His Glu
                805                 810                 815

Cys Gly Val Lys Leu Ser Leu Lys Asp Asn Gly Val Thr Arg Glu Glu
            820                 825                 830

Phe Asp Lys Ala Val Asp Asp Leu Ala Arg Leu Ala Tyr Glu Asp Gln
        835                 840                 845

Cys Thr Thr Thr Asn Pro Val Glu Pro Leu Val Ser Gln Leu Lys Glu
    850                 855                 860

Leu Leu Glu Arg Cys Tyr Asp Gly Thr Gly Val Glu Glu Lys
865                 870                 875

<210> SEQ ID NO 32
<211> LENGTH: 2637
<212> TYPE: DNA
<213> ORGANISM: Lactobacillus reuteri

<400> SEQUENCE: 32
atgcctgcta acaacaagaa acaagttgaa agaaagaat taactgctga agaaaaaaag     60
caaaacgccc aaaagctagt tgacgattta atgactaaga gtcaagctgc ttttgaaaag    120
ttacgttact attcacaaga acaagttgac aagatttgtc aggcaatggc tctcgctgcc    180
gaagaacacc acatggactt agctgttgat gctgctaacg aaactggtcg tggggttgct    240
gaagataagg ctatcaagaa catctacgca agtgaataca tttggaacaa catccgtcac    300
gataagactg ttggtattat cgaagacaat gatgaagacc aaactatcaa aattgctgat    360
ccacttggtg tcattgccgg aattgttcca gttactaacc ctacttcaac aacgatcttc    420
aaatcaatca ttagtgctaa gacacggaat acaatcatct tttctttcca ccgtcaagca    480
atgaagtcat ctatcaagac tgcaaagatt ctccaagaag ctgctgaaaa agccggtgcg    540
ccaaagaaca tgattcaatg ctcccctgaa agtacccgcg aaaacactac cgcattactc    600
caacacccta atactgctac tattttagca accggtggtc cttcattagt taaggctgcc    660
tacagttctg gtaaccctgc tcttggtgtt ggtcctggta acggtcctgc ttacatcgaa    720
aaaactgcca acatcgaacg ttctgtttac gacatcgttc tttctaagac attcgataac    780
ggtatgattt gtgccactga aaactcagtt gttgttgatg aagaaatcta cgacaaggtt    840
aaagaagaat ccaaaagtg gaactgttac ttcttgaagc caaacgaaat tgataaattt    900
actgatggct ttattgaccc agatcgtcat caagttcgtg gtccaatcgc tggtcgttca    960
gctaatgcta ttgctgacat gtgtggtatt aaagtacctg acaacactaa ggttatcatt   1020
gctgaatacg aaggtgttgg tgacaagtac ccactttcag ctgaaaagct ttcaccagta   1080
ttaacaatgt acaaggcaac ctctcacgaa aatgcctttg atatctgtgc tcaattatta   1140
cactacggtg gtgaaggtca cactgctgct attcacaccc ttgatgatga tttagctact   1200
aagtacggtc ttgaaatgcg tgcttcacgg atcattgtta actccccatc tggtattggt   1260
ggtattggta acatctacaa caacatgact ccatccctta ctttaggtac tggttcatac   1320
ggtagtaact caattctca aacgttact gattgggacc tcttaaacat caaaacaatt   1380
gcaaagcggc gtgaaaaccg tcaatgggtt aagattcccc caaaagtata ctttcaacgc   1440
aactcactaa agaattgca agatattcca acattaacc gggcattcat cgttactggt   1500
cctggaatga gcaagcgtgg ttacgttcaa cgtgttatcg atcaattgcg tcaacgccaa   1560
```

-continued

```
aacaacactg ctttcttagt atttgatgac gttgaagaag atccatcaac aaacactgtt   1620
gaaaaaggtg ttgccatgat gaatgacttc aaacctgata caattattgc tcttggtggt   1680
ggttcaccaa tggatgctgc taaggctatg tggatgttct atgagcaccc agaaacttca   1740
tggtatgggg ttatgcaaaa gtaccttgat attcggaagc gtgcttacca aatcaagaag   1800
cctactaagt ctcaacttat tggtatccct actacatcag gtactggttc agaagttact   1860
ccatttgcgg ttattaccga ttcaaaaact catgttaagt acccacttgc tgactacgcc   1920
ttaacaccaa acattgcaat cgttgactca caattcgttg aaactgttcc agcaaaaact   1980
actgcttgga ctggactaga tgttttatgt cacgctactg aatcatatgt ttctgttatg   2040
gcaactgact acactcgtgg ttggtcacta caaaccatca agggtgttat ggaaaacctt   2100
cctaagtcag ttcaaggtga taagttagct cgtcgtaaga tgcacgactt ctcaacaatg   2160
gccgggatgg catttggtca agccttctta ggaattaacc actcccttgc cacaagatg    2220 ggtggagcat tcggtcttcc tcacggtttg cttatcgcta ttgcaatgcc acaagtaatt   2280
cgctttaacg caaaacgtcc acaaaagctt gctctctggc ctcactatga gacttaccat   2340
gcaactaagg actacgctga cattgcacgg ttcattggtt tgaaaggcaa cactgatgaa   2400
gaattagctg aagcatatgc taagaaagtt atcgaacttg ctcacgaatg tggtgttaag   2460
cttagtctta aggacaatgg tgttacacgt gaagaatttg ataaggcggt tgacgatctt   2520
gctcgcttag cttacgaaga tcaatgtact actactaacc cagttgaacc acttgttagc   2580
caactcaagg aattacttga acgttgctac gatggtactg gcgttgaaga aaaataa      2637
```

<210> SEQ ID NO 33
<211> LENGTH: 457
<212> TYPE: PRT
<213> ORGANISM: Lactobacillus reuteri

<400> SEQUENCE: 33

```
Met Ala Tyr Gln Ser Ile Asn Pro Phe Thr Asn Gln Val Glu Lys Thr
1               5                   10                  15

Phe Glu Asn Thr Thr Asp Glu Glu Leu Glu Gln Thr Leu Thr Thr Ala
            20                  25                  30

His Gln Leu Tyr Leu Asp Trp Arg Lys Tyr Asn Asp Leu Glu Glu Arg
        35                  40                  45

Lys Arg Gln Ile Leu Lys Leu Gly Gln Ile Leu Arg Glu Arg Arg Val
    50                  55                  60

Glu Tyr Ala Thr Val Met Ser Lys Glu Met Gly Lys Leu Ile Ser Glu
65                  70                  75                  80

Ala Glu Gly Glu Val Asp Leu Cys Ala Ser Phe Cys Asp Tyr Tyr Ala
                85                  90                  95

Ala His Ala Asp Glu Phe Leu Gln Pro Lys Ile Ile Ala Thr Thr Ser
            100                 105                 110

Gly Arg Ala Lys Val Leu Lys Gln Ser Leu Gly Ile Leu Val Ala Val
        115                 120                 125

Glu Pro Trp Asn Phe Pro Phe Tyr Gln Ile Ala Arg Val Phe Ile Pro
    130                 135                 140

Asn Phe Ile Ala Gly Asn Pro Met Ile Leu Lys Asp Ala Ser Asn Cys
145                 150                 155                 160

Pro Ala Ser Ala Gln Ala Phe Asn Asp Ala Val Lys Glu Ala Gly Ala
                165                 170                 175

Pro Ala Gly Ser Leu Thr Asn Leu Phe Leu Ser Tyr Asp Gln Val Asn
            180                 185                 190
```

```
Lys Ala Ile Ala Asp Lys Arg Val Ala Gly Val Cys Leu Thr Gly Ser
            195                 200                 205
Glu Arg Gly Gly Ala Thr Val Ala Lys Glu Ala Gly Ala Asn Leu Lys
        210                 215                 220
Lys Ser Thr Leu Glu Leu Gly Gly Asn Asp Ala Phe Ile Ile Leu Asp
225                 230                 235                 240
Asp Ala Asp Trp Asp Leu Val Glu Lys Val Ala Pro Ala Ala Arg Leu
                245                 250                 255
Tyr Asn Ala Gly Gln Val Cys Thr Ser Ser Lys Arg Phe Ile Val Leu
            260                 265                 270
Glu Lys Asp Tyr Asp Arg Phe Leu Lys Met Met Lys Asp Ala Phe Ser
        275                 280                 285
Lys Val Lys Met Gly Asp Pro Leu Asp Pro Leu Thr Thr Leu Ala Pro
290                 295                 300
Leu Ser Ser Lys Lys Ala Lys Glu Lys Leu Gln Gln Gln Val Ala Thr
305                 310                 315                 320
Ala Val Glu Asn Gly Ala Lys Val Tyr Tyr Gly Asn Lys Pro Val Asp
                325                 330                 335
Met Glu Gly Gln Phe Phe Met Pro Thr Ile Leu Thr Asp Ile Thr Pro
            340                 345                 350
Asp Asn Pro Ile Phe Asp Thr Glu Met Phe Gly Pro Val Ala Ser Val
        355                 360                 365
Tyr Lys Val Ser Ser Glu Glu Glu Ala Ile Glu Leu Ala Asn Asn Ser
370                 375                 380
Ser Tyr Gly Leu Gly Asn Thr Ile Phe Ser Asn Asp Ser Glu His Ala
385                 390                 395                 400
Glu Arg Val Ala Ala Lys Ile Glu Thr Gly Met Ser Trp Ile Asn Ala
                405                 410                 415
Gly Trp Ala Ser Leu Pro Glu Leu Pro Phe Gly Gly Val Lys Asn Ser
            420                 425                 430
Gly Tyr Gly Arg Glu Leu Ser Ser Tyr Gly Ile Asp Glu Phe Thr Asn
        435                 440                 445
Lys His Leu Ile Tyr Glu Ala Arg Gln
    450                 455

<210> SEQ ID NO 34
<211> LENGTH: 1374
<212> TYPE: DNA
<213> ORGANISM: Lactobacillus reuteri

<400> SEQUENCE: 34
atggcatatc aaagtatcaa tccatttacg aaccaagtag aaaaaacgtt tgaaaataca      60
actgatgaag aattagaaca acattaact acggcgcatc aattatattt agattggcgg     120
aagtataatg accttgaaga acggaaacgg caaattttaa agttaggtca atattacgt      180 gaacggcgtg ttgaatatgc gacagttatg agtaaggaaa tgggaaaatt aattagcgaa     240
gcagaaggcg aggttgacct ttgtgcttct ttctgtgatt attatgcagc ccatgcagat     300
gaatttctgc aaccaaaaat tattgcgaca acgagtggac gcgccaaagt tttgaagcaa     360
tcattaggaa ttttagttgc agttgaacct tggaattttcc cattctatca aattgcccgg     420
gtatttattc ccaactttat tgcaggaaac cccatgatct tgaaggatgc gtcgaattgt     480
ccagcatccg cccaagcatt taacgatgcc gttaaggaag ctggtgcgcc agccggcagt     540
ttaactaatt tattcctttc atatgaccaa gtaaataagg caattgctga taagcgggta     600
```

```
gccggcgttt gtcttactgg ttctgaacgt ggtggtgcaa ccgttgctaa agaggctggt    660
gctaatttga agaagagcac tttggaactt ggtggtaatg atgcctttat tatcttagac    720
gatgcagatt gggatcttgt cgaaaaagtt gccccggcag cccgtctgta taatgctgga    780
caagtatgta catcatcaaa acgttttatt gtccttgaaa aggattatga tcgtttctta    840
aagatgatga aagatgcgtt ctcgaaagtt aaaatggtg atccccttga tccattaaca    900
actctggcac cattatcatc taagaaagca aagaaaagc tccaacagca agtcgcaaca    960
gcagtagaaa atggggccaa agtttactat ggtaataagc cggttgacat ggaaggtcaa   1020
ttctttatgc caacgatctt aactgatatc actccagata acccaatatt tgatacggaa   1080
atgtttgggc cagtggcttc ggtttataag gttagttccg aagaggaagc aatcgaactg   1140
gctaataatt caagctatgg gttaggaaac actatcttta gcaatgattc cgaacatgcg   1200
gaacgagtag cagcgaagat cgaaactgga atgagttgga ttaatgccgg ctgggcttca   1260
ttaccagaat taccatttgg tggtgttaag aattcaggtt acggtcgtga actcagcagt   1320
tacggaattg atgaatttac taacaaacat ctaatttacg aagcacgaca ataa          1374
```

<210> SEQ ID NO 35
<211> LENGTH: 477
<212> TYPE: PRT
<213> ORGANISM: Lactobacillus reuteri

<400> SEQUENCE: 35

```
Met Gln Ile Asn Asp Ile Glu Ser Ala Val Arg Lys Ile Leu Ala Glu
1               5                   10                  15

Glu Leu Asp Asn Ala Ser Ser Ser Ala Asn Val Ala Ala Thr Thr
            20                  25                  30

Asp Asn Gly His Arg Gly Ile Phe Thr Asn Val Asn Asp Ala Ile Ala
        35                  40                  45

Ala Ala Lys Ala Ala Gln Glu Ile Tyr Arg Asp Lys Pro Ile Ala Val
    50                  55                  60

Arg Gln Gln Val Ile Asp Ala Ile Lys Glu Gly Phe Arg Pro Tyr Ile
65                  70                  75                  80

Glu Lys Met Ala Lys Asp Ile Lys Glu Glu Thr Gly Met Gly Thr Val
                85                  90                  95

Glu Ala Lys Ile Ala Lys Leu Asn Asn Ala Leu Tyr Asn Thr Pro Gly
            100                 105                 110

Pro Glu Ile Leu Glu Pro Val Val Glu Asn Gly Asp Gly Gly Met Val
        115                 120                 125

Met Tyr Glu Arg Leu Pro Tyr Gly Val Ile Gly Ala Val Gly Pro Ser
    130                 135                 140

Thr Asn Pro Ser Glu Thr Val Ile Ala Asn Ala Ile Met Met Leu Ala
145                 150                 155                 160

Gly Gly Asn Thr Leu Tyr Phe Gly Ala His Pro Gly Ala Lys Asn Val
                165                 170                 175

Thr Arg Trp Thr Ile Glu Lys Met Asn Asp Phe Ile Ala Asp Ala Thr
            180                 185                 190

Gly Leu His Asn Leu Val Val Ser Ile Glu Thr Pro Thr Ile Glu Ser
        195                 200                 205

Val Gln Gln Met Met Lys His Pro Asp Ile Ala Met Leu Ala Val Thr
    210                 215                 220

Gly Gly Pro Ala Val Val His Gln Ala Met Thr Ser Gly Lys Lys Ala
225                 230                 235                 240

Val Gly Ala Gly Pro Gly Asn Pro Pro Ala Met Val Asp Ala Thr Ala
```

|  |  |  |  |  |  |  |  |  |  |  |  |
|---|---|---|---|---|---|---|---|---|---|---|---|
|  |  |  | 245 |  |  |  | 250 |  |  |  | 255 |

Asp Ile Asp Leu Ala Ala His Asn Ile Ile Thr Ser Ala Ser Phe Asp
          260                      265                     270

Asn Asp Ile Leu Cys Thr Ala Glu Lys Glu Val Val Ala Glu Ser Ser
   275                      280                      285

Ile Lys Asp Glu Leu Ile Arg Lys Met Gln Asp Gly Ala Phe Val
          290                     295                    300

Val Asn Arg Glu Gln Ala Asp Lys Leu Ala Asp Met Cys Ile Gln Glu
305                    310                      315                    320

Asn Gly Ala Pro Asp Arg Lys Phe Val Gly Lys Asp Ala Thr Tyr Ile
             325                      330                    335

Leu Asp Gln Ala Asn Ile Pro Tyr Thr Gly His Pro Val Glu Ile Ile
         340                     345                    350

Cys Glu Leu Pro Lys Glu His Pro Leu Val Met Thr Glu Met Leu Met
       355                     360                    365

Pro Ile Leu Pro Val Val Ser Cys Pro Thr Phe Asp Asp Val Leu Lys
   370                      375                      380

Thr Ala Val Glu Val Glu Lys Gly Asn His His Thr Ala Thr Ile His
385                    390                      395                    400

Ser Asn Asn Leu Lys His Ile Asn Asn Ala Ala His Arg Met Gln Cys
             405                      410                    415

Ser Ile Phe Val Val Asn Gly Pro Ser Tyr Val Gly Thr Gly Val Ala
         420                     425                    430

Asp Asn Gly Ala His Ser Gly Ala Ser Ala Leu Thr Ile Ala Thr Pro
       435                     440                    445

Thr Gly Glu Gly Thr Cys Thr Ala Arg Thr Phe Thr Arg Arg Val Arg
   450                      455                      460

Leu Asn Ser Pro Gln Gly Phe Ser Val Arg Asn Trp Tyr
465                    470                      475

```
<210> SEQ ID NO 36
<211> LENGTH: 1434
<212> TYPE: DNA
<213> ORGANISM: Lactobacillus reuteri

<400> SEQUENCE: 36
atgcagatta tgatattga aagtgctgta cgcaaaattc ttgccgaaga actagataat      60
gccagctctt caagtgcaaa cgttgcagct actactgata atggtcatcg cggaattttc     120
actaatgtca atgatgcaat tgctgctgca aaagctgctc aagaaatata tcgggataag     180
ccaattgctg ttcgccaaca agtgattgat gccattaagg aaggattccg cccatatatt     240
gaaaaaatgg ctaaagatat caagaagaa acaggaatgg aacagtaga ggccaaaatt      300 gctaagttaa caatgccttt gtacaacact cctggtcccg agattcttga accagttgta     360
gaaaacggtg acggtgggat ggttatgtat gaacggttac catatggtgt tattggtgcg     420
gttggcccaa gtacaaaccc ttcagaaact gtaattgcta atgcgatcat gatgcttgcc     480
ggtggtaata ctctttactt tggtgctcac cctggcgcaa agaatgttac tgctctggaca    540 attgaaaaga tgaacgattt tattgcagat gcaacaggcc ttcataattt agttgtaagt     600
attgaaacac caacaattga atcagttcaa caaatgatga agcaccccga cattgcaatg     660
ttagcagtaa ctggtggccc agctgttgtt caccaagcaa tgaccagtgg taagaaagcg     720
gttggtgctg gtcctggtaa tcctcctgca atggttgatg ctactgctga tattgattta     780
gctgctcata atatcattac atctgcttca tttgataatg atattttatg tactgctgaa     840
```

```
aaggaagtag ttgcagaaag tagcattaaa gatgaattaa ttcgtaagat gcaagatgaa    900
ggtgcctttg tagttaaccg tgaacaagcc gataaattag ctgatatgtg tatccaagaa    960
aatggtgctc ctgatcgtaa atttgttggt aaggatgcaa cttatatctt agaccaagct   1020
aatattcctt acacaggcca cccagttgaa attatttgtg aacttcctaa ggaacatcca   1080
ttagtaatga ctgaaatgtt aatgccaatt ttaccagttg tttcttgtcc aacatttgat   1140
gatgttttga agactgctgt tgaagttgaa aaaggtaacc atcacacagc tactattcat   1200
tccaataacc ttaagcatat taataatgct gctcaccgga tgcaatgttc aatctttgtt   1260
gttaatggcc catcctatgt tggtacaggt gttgcagata atggagctca ctcaggtgct   1320
tcagcattaa caattgctac gccaactggt gaaggaacat gtactgcacg aacatttact   1380
cgtcgggttc gtttgaactc accacaagga ttctcagtac gtaactggta ttaa         1434
```

<210> SEQ ID NO 37
<211> LENGTH: 383
<212> TYPE: PRT
<213> ORGANISM: Lactobacillus reuteri

<400> SEQUENCE: 37

```
Met Lys Phe Val Ile Ala Pro Asp Ser Phe Lys Gly Gly Leu Thr Ala
1               5                   10                  15

Lys Glu Ala Ala Asn Val Met Ala Glu Gly Ile Lys Arg Val Phe Pro
            20                  25                  30

Asn Ala Glu Tyr Ala Leu Val Pro Met Ala Asp Gly Gly Glu Gly Thr
        35                  40                  45

Val Gln Ser Leu Val Asp Ala Thr Asn Gly Gln Lys Met Ile Ala Lys
    50                  55                  60

Val His Asn Pro Leu Asn Lys Leu Val Asn Ala Glu Tyr Gly Ile Leu
65                  70                  75                  80

Gly Asp Gly Glu Thr Ala Val Ile Glu Met Ala Ala Ser Gly Leu
                85                  90                  95

Gln Phe Val Asn Lys Glu Thr Ala Asn Pro Leu Ile Thr Thr Thr Tyr
            100                 105                 110

Gly Thr Gly Glu Leu Ile Lys Asp Ala Leu Asp His Asn Ile Lys Lys
        115                 120                 125

Ile Ile Ile Gly Ile Gly Gly Ser Ala Thr Val Asp Gly Gly Ala Gly
    130                 135                 140

Met Ala Gln Ala Leu Gly Ala Arg Leu Leu Asp Ala Asp Asn His Glu
145                 150                 155                 160

Ile Gly Leu Gly Gly Gly Glu Leu Ala Ser Leu Glu Gln Val Asp Phe
                165                 170                 175

Gly Gly Leu Asp Pro Arg Leu Lys Asn Val Asp Ile Gln Ile Ala Ser
            180                 185                 190

Asp Val Thr Asn Pro Leu Thr Gly Lys Asn Gly Ala Ala Pro Val Phe
        195                 200                 205

Gly Pro Gln Lys Gly Ala Asp Glu Glu Met Val Asn Ile Leu Asp Lys
    210                 215                 220

Asn Leu His His Tyr Ala Arg Lys Ile Val Ala Ala Gly Gly Pro Asp
225                 230                 235                 240

Val Glu Gln Thr Ala Gly Ala Gly Ala Ala Gly Gly Leu Gly Ala Gly
                245                 250                 255

Leu Ile Ala Phe Thr Gly Ala Thr Met Lys Arg Gly Val Glu Leu Val
            260                 265                 270

Ile Glu Ala Thr Gln Leu Gln Lys Lys Ala Val Gly Ala Asp Tyr Val
```

```
                275                 280                 285
Phe Thr Gly Glu Gly Gly Ile Asp Phe Gln Thr Lys Phe Gly Lys Thr
    290                 295                 300

Pro Tyr Gly Val Ala Lys Ala Thr Lys Glu Val Ala Pro Thr Ala Pro
305                 310                 315                 320

Val Ile Val Leu Ala Gly Asn Ile Gly Lys Gly Val Asn Asp Leu Tyr
                325                 330                 335

Ser Ser Thr Ala Ile Asp Ala Ile Phe Ala Thr Pro Glu Gly Ala Lys
            340                 345                 350

Pro Leu Lys Thr Ala Leu Ala Asp Ala Pro Ile Asp Ile Ala Gln Thr
        355                 360                 365

Ala Glu Asn Val Ala Arg Leu Ile Lys Val Ser His Val Ser Asn
    370                 375                 380

<210> SEQ ID NO 38
<211> LENGTH: 1152
<212> TYPE: DNA
<213> ORGANISM: Lactobacillus reuteri

<400> SEQUENCE: 38
atgaaatttg taattgctcc agattcattt aaaggcggat aacagcaaa agaagcagca      60 aatgtgatgg cagaaggaat caaaagagtg tttccgaatg ccgagtatgc tttagttcca     120
atggctgatg gaggagaggg gactgttcaa tccttagttg atgcgactaa cggtcaaaaa     180
atgattgcta aagtccacaa cccattaaat aaattagtta atgctgagta cggaatatta     240
ggtgatgggg aaacggcagt gattgagatg gcggcggcaa gtggccttca atttgttaat     300
aaggagactg cgaacccgct tattacaact acatatggta ccgcgagtt aattaaggat      360 gctcttgacc ataacattaa aaaataatt attggaattg gtggaagtgc aaccgttgat     420
ggcggagcgg ggatggccca agcacttgga gcacgtttat ggatgctga taatcatgaa      480 attggtttag gcggtggtga gttagcaagt ttagagcaag tagattttgg aggattagat     540
cctcgcttaa aaaatgtaga tattcagatt gcatcagacg taaccaaccc attaacagga     600
aaaaatgggg cagccccagt atttggcccg caaaaggag ctgatgaaga atggtgaac      660 atcttggaca aaatcttca tcattatgcc cgaaaaatag ttgcagctgg tgggccagac     720
gttgaacaaa cggcaggtgc aggggcagcc ggtggtttag gagccgggtt gatagcattt     780
accggtgcga caatgaagcg aggagtagaa ttagtgattg aagcaactca actacaaaaa     840
aaggcagttg cgctgatta tgttttact ggtgaaggag gaattgattt ccagactaaa      900
tttggtaaaa cgccatatgg agtcgctaag caactaaag aggtggctcc aactgctccg     960
gtaattgtgt tggctggaaa tattggtaaa ggcgtaaatg atctatattc atccacggcc    1020
attgatgcaa ttttttgcaac tcctgaaggg gctaaaccat taaaaacagc attagcagat    1080
gcacctattg atattgctca aacagcggaa aacgttgcac gtttaattaa agtgagtcat    1140
gttagtaatt aa                                                        1152

<210> SEQ ID NO 39
<211> LENGTH: 500
<212> TYPE: PRT
<213> ORGANISM: Lactobacillus reuteri

<400> SEQUENCE: 39

Leu Ser Glu Gln Gln Tyr Ile Met Ala Ile Asp Gln Gly Thr Thr Ser
1               5                   10                  15

Ser Arg Ala Ile Ile Phe Asp His Asp Gly Asn Lys Val Ala Ile Ser
```

```
                  20                  25                  30
Gln Gln Glu Phe Pro Gln Tyr Phe Pro Gln Pro Gly Trp Val Glu His
             35                  40                  45

Asp Pro Leu Glu Ile Trp Asp Ser Val Gln Ser Val Ile Ser Asn Val
 50                  55                  60

Met Ile Lys Ser Gln Ile Lys Pro Tyr Lys Ile Ala Ala Ile Gly Ile
 65                  70                  75                  80

Thr Asn Gln Arg Glu Thr Thr Val Ile Trp Asp Arg His Thr Gly Lys
                 85                  90                  95

Pro Ile Tyr Asn Ala Ile Val Trp Gln Ser Lys Gln Thr Ser Asp Ile
            100                 105                 110

Ala Glu Gln Leu Ile Lys Asp Gly Tyr Lys Asp Met Ile His Gln Lys
            115                 120                 125

Thr Gly Leu Val Ile Asp Ser Tyr Phe Ala Ala Thr Lys Ile Lys Trp
            130                 135                 140

Ile Leu Asp His Val Pro Gly Ala Arg Glu Lys Ala Ala Lys Gly Asp
145                 150                 155                 160

Leu Met Phe Gly Thr Ile Asp Thr Trp Leu Leu Trp Asn Leu Ser Gly
                165                 170                 175

Arg Arg Val His Ala Thr Asp Val Thr Asn Ala Ser Arg Thr Met Leu
            180                 185                 190

Phe Asn Ile His Thr Leu Asp Trp Asp Gln Asp Ile Leu Asp Leu Leu
            195                 200                 205

Asp Ile Pro Gln Ser Leu Leu Pro Val Val Lys Pro Ser Ser Ala Ile
            210                 215                 220

Tyr Gly Tyr Thr Gly Asp Tyr His Phe Tyr Gly Val Gln Ile Pro Ile
225                 230                 235                 240

Ala Gly Ile Ala Gly Asp Gln Gln Ala Ala Leu Phe Gly Gln Ala Ala
                245                 250                 255

Tyr Asp Lys Gly Ser Ile Lys Asn Thr Tyr Gly Thr Gly Ala Phe Ile
            260                 265                 270

Val Met Asn Thr Gly Leu Lys Pro Thr Leu Ser Asp Asn Gly Leu Leu
            275                 280                 285

Thr Thr Ile Ala Tyr Gly Leu Asp Gly Gln Thr His Tyr Ala Leu Glu
            290                 295                 300

Gly Ser Ile Phe Val Ala Gly Ser Ala Val Gln Trp Leu Arg Asp Gly
305                 310                 315                 320

Leu Lys Met Phe Asp Lys Ala Ser Glu Ser Glu Gln Met Ala Val Asp
                325                 330                 335

Ala Lys Thr Thr Gly Gly Val Tyr Val Val Pro Ala Phe Thr Gly Leu
            340                 345                 350

Gly Ala Pro Tyr Trp Asp Gln Glu Val Arg Gly Ala Met Phe Gly Leu
            355                 360                 365

Thr Arg Gly Thr Glu Arg Gly His Ile Ile Arg Ala Thr Leu Glu Ala
            370                 375                 380

Ile Ala Tyr Gln Thr Lys Asp Val Val Asp Thr Met Val Lys Asp Thr
385                 390                 395                 400

Gln Leu Pro Leu Thr Ala Leu Thr Val Asn Gly Gly Ala Ser Arg Asn
                405                 410                 415

Asn Phe Met Met Gln Phe Gln Ala Asp Ile Leu Gln Thr Pro Ile Lys
            420                 425                 430

Arg Ala Ala Met Glu Glu Thr Thr Ala Leu Gly Ala Ala Phe Leu Ala
            435                 440                 445
```

Gly Leu Ala Val Asp Phe Trp Glu Asp Gln Asp Glu Leu Arg Lys Leu
            450                 455                 460

Ser Arg Ile Gly Asp Gln Phe Asp Pro Gln Met Asp Pro Gln Lys Ala
465                 470                 475                 480

Ala Asp Leu Tyr Arg Gly Trp Gln Arg Ala Ile Ala Ala Ala Gln Phe
                485                 490                 495

Tyr Gly Lys Asp
            500

<210> SEQ ID NO 40
<211> LENGTH: 1503
<212> TYPE: DNA
<213> ORGANISM: Lactobacillus reuteri

<400> SEQUENCE: 40

| | |
|---|---|
| ttgagtgaac aacaatatat catggcgatt gaccagggaa cgacgagctc acgggcgatt | 60 |
| atctttgacc atgacggaaa taaggttgcg atcagtcagc aggaatttcc ccaatacttc | 120 |
| ccgcagccgg ggtgggttga acatgatcct ctagagattt gggatagcgt tcaatcagtg | 180 |
| atttcaaatg taatgattaa gtcccagatc aagccctata agattgcggc aattgggatt | 240 |
| actaaccaac gggagacgac ggttatttgg gatcgccata ccggtaagcc gatttataac | 300 |
| gcaattgtct ggcaatcgaa gcaaacgagc gacatcgccg aacaattgat taaagatggt | 360 |
| tataaggata tgatccacca gaagactggc ttggtgattg attcgtattt cgcggccact | 420 |
| aagatcaagt ggatccttga ccatgttcct ggtgcccggg aaaagcagc aaagggagac | 480 |
| ttgatgtttg ggactatcga tacttggtta ctatggaatt tatcgggacg gcgggtccac | 540 |
| gcaacggatg tgaccaatgc cagccggacg atgcttttta atatccatac cctcgactgg | 600 |
| gatcaagata tccttgacct gcttgatatt ccccagtcgc ttttgccagt agtaaagcca | 660 |
| agttcagcca tttacggtta tactggcgac taccacttct atggggtgca gattccaatt | 720 |
| gccgggattg caggtgacca acaagcagcc ctctttggtc aagcagccta tgataaaggt | 780 |
| tcaatcaaga acacctatgg gactggagcc ttcatcgtca tgaatacggg actaaaaccc | 840 |
| acgctttcgg ataacggctt gttgacgacg attgcgtatg gcctgacgg gcaaactcat | 900 |
| tacgcgcttg aaggaagtat cttcgtggcc ggttctgccg ttcaatggtt gcgggatggt | 960 |
| ctcaagatgt tgataaggc aagcgagtcc gaacaaatgg ctgtcgatgc caagacaact | 1020 |
| ggcggcgttt atgtcgtccc cgcctttaca ggattaggcg caccgtactg ggatcaagaa | 1080 |
| gtgcggggcg caatgtttgg ccttacccgt ggaactgaac gggggacatat catccgtgca | 1140 |
| actttggaag ccattgccta ccagaccaaa gatgttgtcg atacgatggt caaggacacc | 1200 |
| caattaccac taacagcact aacggttaac gggggcgctt cacggaacaa cttcatgatg | 1260 |
| cagttccagg ccgatatctt acaaacgcca atcaagcggg cagcaatgga agagacaacc | 1320 |
| gcgctgggag cagcctttct cgctggattg gccgttgatt tctgggaaga ccaggatgag | 1380 |
| ttacggaagc tatcacggat tggcgaccag tttgatccac aaatggatcc gcaaaaggca | 1440 |
| gctgacttgt atcggggatg gcaacgggcc attgcagctg cgcagttta tggcaaagat | 1500 |
| taa | 1503 |

<210> SEQ ID NO 41
<211> LENGTH: 338
<212> TYPE: PRT
<213> ORGANISM: Lactobacillus reuteri

<400> SEQUENCE: 41

```
Met Ala Glu Lys Ile Ala Val Leu Gly Ala Gly Ser Trp Gly Ser Val
  1               5                  10                 15

Leu Ala Asn Met Leu Thr Glu Asn Gly His Asp Val Thr Leu Trp Ser
             20                  25                  30

Arg Asn Glu Glu Gln Val Lys Gln Leu Asn Thr Glu His Thr Asn Pro
         35                  40                  45

Arg Tyr Met Lys Asp Phe Val Tyr Ser Thr Asn Leu Thr Ala Thr Thr
     50                  55                  60

Asp Met Lys Lys Ala Val Lys Gly Ala Ser Val Val Leu Ile Val Ile
 65                  70                  75                  80

Pro Thr Lys Gly Leu Arg Glu Val Ala Lys Gln Leu Asn Ala Ile Leu
                 85                  90                  95

Thr Glu Leu His Gln Lys Pro Leu Val Ile His Ala Thr Lys Gly Leu
            100                 105                 110

Glu Gln Asn Thr Tyr Lys Arg Pro Ser Glu Met Leu Ser Glu Asp Ile
        115                 120                 125

Ser Pro Glu Asn Arg Gln Ala Ile Val Val Leu Ser Gly Pro Ser His
130                 135                 140

Ala Glu Asp Val Ala Ile Lys Asp Met Thr Ala Val Thr Ala Ala Cys
145                 150                 155                 160

Glu Asp Leu Ala Ser Ala Lys Lys Ala Gln Lys Leu Phe Ser Asn Ser
                165                 170                 175

Tyr Phe Arg Val Tyr Thr Asn Asp Asp Val Ile Gly Ala Glu Phe Gly
            180                 185                 190

Ala Ala Leu Lys Asn Ile Ile Ala Ile Gly Ala Gly Ala Ile Gln Gly
        195                 200                 205

Leu Gly Tyr His Asp Asn Ala Arg Ala Ala Leu Ile Thr Arg Gly Leu
210                 215                 220

Ala Glu Ile Arg Arg Leu Gly Val Ala Phe Gly Ala Asn Pro Met Thr
225                 230                 235                 240

Phe Ile Gly Leu Ser Gly Val Gly Asp Leu Val Val Thr Ala Thr Ser
                245                 250                 255

Lys Asn Ser Arg Asn Trp Arg Ala Gly Tyr Gln Leu Gly Gln Gly Lys
            260                 265                 270

Lys Leu Gln Asp Val Ile Asp Asn Met Gly Met Val Ile Glu Gly Val
        275                 280                 285

Tyr Thr Thr Lys Ala Ala Tyr Glu Leu Ser Arg Lys Arg Gln Val Gln
    290                 295                 300

Met Pro Ile Thr Glu Ala Leu Tyr Arg Val Leu Tyr Glu Gly Glu Asp
305                 310                 315                 320

Ile Lys Thr Ala Ile Ser Gln Leu Met Asp Arg Asp Leu Thr Ser Glu
                325                 330                 335

Asn Glu

<210> SEQ ID NO 42
<211> LENGTH: 1017
<212> TYPE: DNA
<213> ORGANISM: Lactobacillus reuteri

<400> SEQUENCE: 42
atggcagaaa aaattgctgt tttaggtgct ggttcgtggg gcagtgtttt agcaaacatg      60
cttacagaaa atggccacga tgtaacatta tggtctcgta atgaggaaca agttaagcaa     120
ttaaatactg aacatacaaa tcctcgctat atgaaagatt ttgtttattc tactaactta     180
acagcaacaa cggacatgaa aaaagctgtt aagggtgcca gtgtggtcct gattgtaatt     240
```

```
ccaacaaagg gtcttcgtga agttgctaag caattaaatg caattttgac tgaattacat    300 caaaaccgc tagttattca cgcaacgaaa ggcttagaac aaaatactta taagcggcca    360
tcggaaatgc ttagcgaaga tatttctcct gaaaaccgtc aggcaattgt tgttttatca    420
ggtccgagtc atgctgaaga tgtggcgatt aaagatatga cagctgtaac cgcagcttgt    480
gaggacctgg ccagtgctaa aaaggcgcag aagttattta gtaattctta tttccgtgtg    540
tacactaatg acgatgtaat tggtgccgaa tttggcgcag ccttaaagaa cattattgca    600
attggtgctg gagctattca gggacttggt tatcatgata atgctcgggc agcgttaatt    660
actcgtggac ttgcagaaat tcgccgattg ggagttgctt ttggtgccaa cccgatgact    720
tttattggtc tttctggggt tggtgacctt gttgttactg ctaccagtaa aaattctcga    780
aattggcgtg ctggctatca attggggcaa ggaaaaaagc ttcaagatgt aattgataat    840
atgggaatgg ttatcgaagg tgtctatact accaaagccg cttatgaatt aagtcgtaaa    900
cgacaagtac agatgccaat taccgaagct ctttaccgtg ttttgtatga aggcgaagat    960
attaaaactg caatttctca attaatggac cgagatctta cttcagaaaa cgaataa    1017
```

<210> SEQ ID NO 43
<211> LENGTH: 256
<212> TYPE: PRT
<213> ORGANISM: Lactobacillus reuteri

<400> SEQUENCE: 43

```
Met Arg Lys Pro Phe Ile Ala Ala Asn Trp Lys Met His Lys Asn Val
1               5                   10                  15

Gln Glu Ser Val Glu Phe Val Asp Ala Ile Lys Gly Lys Leu Pro Asp
            20                  25                  30

Pro Gln Glu Val Glu Val Gly Ile Ala Ala Gln Ala Phe Ala Leu Pro
        35                  40                  45

Ser Met Val Gln Ala Ala Asp Asp Ser Gly Leu Lys Ile Ile Ala Gln
    50                  55                  60

Asn Ala Ala Ala Glu Tyr Ser Gly Ala Phe Thr Gly Glu Ile Ser Leu
65                  70                  75                  80

Arg Gly Leu Ala Asp Ala Gly Val Ser Tyr Val Met Leu Gly His Ile
                85                  90                  95

Glu Arg Arg His Leu Phe His Glu Asp Asn Glu Leu Val Asn Arg Lys
            100                 105                 110

Val Leu Ala Ala Leu Gln Met Gly Val Thr Pro Ile Ile Cys Thr Asp
        115                 120                 125

Glu Thr Met Val Gln Lys Glu Val Asn Gly Glu Ile His Tyr Val Phe
    130                 135                 140

Gln Gln Leu Met Ser Val Leu Arg Gly Val Ser Leu Asp Gln Ile Lys
145                 150                 155                 160

Asn Val Val Ser Tyr Glu Pro Ser Trp Ala Val Gly Tyr Gly Gln
                165                 170                 175

His Ala Asn Pro Val Leu Ala Glu Glu Gly Cys Arg Gln Ile Arg Arg
            180                 185                 190

Thr Ile Ala Asp Asn Tyr Thr Tyr Glu Ile Ala Asp Lys Ile Arg Ile
        195                 200                 205

Leu Tyr Gly Gly Ser Val Asn Pro Asp Asn Ile Gly Met Ile Met Asn
    210                 215                 220

Lys Pro Asp Val Asp Gly Val Leu Ile Gly Arg Ala Ser Leu Asp Val
225                 230                 235                 240
```

Asp Asn Phe Leu Arg Met Val Asn Tyr Leu Lys Asn Asp Gln Glu Lys
            245                 250                 255

<210> SEQ ID NO 44
<211> LENGTH: 771
<212> TYPE: DNA
<213> ORGANISM: Lactobacillus reuteri

<400> SEQUENCE: 44
atgcgcaaac cctttattgc tgctaattgg aagatgcata gaatgtcca agaatcggtt      60 gaatttgtgg atgcaattaa aggaaagcta ccagatccgc aagaagttga agtcggaatt    120
gcagcccaag cttttgcatt acccagtatg gttcaagccg ctgatgattc aggattaaag    180
ataatcgcgc aaaacgcggc ggctgaatat tcgggagctt tcactggtga aattagctta    240
cgaggtttag ctgacgccgg tgtttcatat gtaatgttag acatattga acggcgccat    300 ttattccacg aggataatga gttggttaat cggaaagtgt tggcagccct tcaaatggga    360
gttaccccga taatttgtac ggatgaaacg atggtccaga agaagttaa tggtgaaatt    420 cactacgttt ccagcaatt gatgagcgta ttgaggggcg tttctcttga tcaaattaaa    480
aatgtagttg tttcctatga accaagttgg gcagttggat atggtcagca tgctaatcca    540
gttcttgctg aagaaggatg ccgtcaaatt cggcgaacga ttgctgataa ctacacttat    600
gagattgcta taagatcag gattctttat gggggcagtg tcaatccaga taatatcgga    660
atgattatga caagccaga tgtagatggg gtattaatcg gtcgggcaag tttagatgtt    720
gataattttt tgcgaatggt caattattta aaaaatgatc aagaaaaata a             771

<210> SEQ ID NO 45
<211> LENGTH: 259
<212> TYPE: PRT
<213> ORGANISM: Lactobacillus reuteri

<400> SEQUENCE: 45

Met Arg Lys Pro Phe Ile Ile Ala Asn Trp Lys Met Asn Lys Asn Val
1                5                  10                  15

His Glu Ser Val Ala Phe Val Lys Ala Ile Lys Glu Lys Leu Pro Ala
            20                  25                  30

Asp Lys Glu Ile Gly Ile Ala Ala Gln Ala Val Ser Leu Tyr Asn Met
        35                  40                  45

Lys Lys Val Ala Ser Ser Ser Asn Leu Gln Ile Ile Ala Gln Asn Ala
    50                  55                  60

Ser Ala Glu Leu Glu Gly Pro Tyr Thr Gly Glu Ile Ser Met Arg Ser
65                  70                  75                  80

Leu Ala Asp Ala Gly Val Thr Tyr Val Met Leu Gly His Leu Glu Arg
                85                  90                  95

Arg Arg Leu Phe Asn Glu Ser Asn Asp Ser Ile Asn Gln Lys Val Leu
            100                 105                 110

Ala Ala Leu Asn Ala Gly Ile Ile Pro Ile Ile Cys Thr Asp Glu Glu
        115                 120                 125

Met Val Gln Thr Glu Val Asn Gly Gln Ile His Tyr Val Phe Arg Gln
    130                 135                 140

Leu Lys Ser Val Leu Lys Gly Val Pro Ala Asn Lys Leu Ser Gln Ile
145                 150                 155                 160

Val Ile Ser Tyr Glu Pro Ser Trp Ala Val Gly Ser Thr His Gln Ala
                165                 170                 175

Asn Pro Asp Ile Ala Glu Glu Gly Cys Gln Ala Ile Arg Gln Ser Leu
            180                 185                 190

```
Val Glu Met Tyr Gly Asn Glu Ile Gly Glu Gln Val Arg Ile Leu Tyr
        195                 200                 205

Gly Gly Ser Val Asn Pro Glu Asn Ile Gly Gln Ile Met Ser Lys Pro
        210                 215                 220

Asn Val Asp Gly Ala Leu Ile Gly Arg Ala Ser Leu Glu Ile Glu Ser
225                 230                 235                 240

Phe Leu Gln Met Ile Asn Tyr Ile Glu Leu Ala Ser Lys Gln Lys Leu
                245                 250                 255

Gln Val Ile

<210> SEQ ID NO 46
<211> LENGTH: 780
<212> TYPE: DNA
<213> ORGANISM: Lactobacillus reuteri

<400> SEQUENCE: 46
atgcgcaaac cgtttattat tgcgaactgg aaaatgaata aaaacgttca tgaatctgtt       60
gcgtttgtta aagcaattaa agaaaagctc ccggcagata agaaattgg atcgccgcg       120 caagcagttt cgctatataa catgaaaaaa gtggcgagct cttccaactt acaaattatt      180
gctcaaaatg catctgctga gttagaggga ccatatactg agaaattag catgcgaagt       240 ttagcagatc gggcgtgac atacgtgatg ctaggccatt tagagcgccg acgcctttt       300 aacgagagta atgattcaat taatcaaaaa gttttagcag ccctcaatgc tggtattatt      360
ccaatcattt gtacggatga agatggtc caaacagaag ttaacggaca aattcattat       420
gtatttcgcc aactaaaaag cgtccttaaa ggggtaccag ctaataaact atcacagatt      480
gttatttcgt atgaaccaag ttgggccgtt gggagcacgc atcaagcaaa tccagacatt      540
gcggaagagg gatgtcaggc aattcgtcaa agcctggttg aaatgtatgg taatgagatt      600
ggcgagcaag tccgaatact ctatggtggc agcgttaatc ccgagaacat tggtcaaatt      660
atgagtaaac caaatgttga tggggcgcta atcggtcgcg caagtctcga gattgaaagt      720
ttcttacaaa tgattaatta tatcgaatta gcgagcaagc agaagttaca ggtaatttag      780

<210> SEQ ID NO 47
<211> LENGTH: 249
<212> TYPE: PRT
<213> ORGANISM: Lactobacillus reuteri

<400> SEQUENCE: 47

Met Arg Val Pro Ile Ile Ala Gly Asn Trp Lys Met His Lys Asp Val
1               5                   10                  15

Gln Glu Ala Val Ser Phe Ile Glu Lys Val Lys Asn Gln Leu Pro Pro
            20                  25                  30

Ala Asp Gln Leu Glu Thr Ala Ile Ala Ala Pro Thr Leu Cys Leu Val
        35                  40                  45

Pro Met Val Lys Ala Ala Glu Glu Ser Pro Leu Lys Ile Met Ala Glu
    50                  55                  60

Asn Cys Tyr Tyr Lys Asn Glu Gly Ala Tyr Thr Gly Glu Thr Ser Pro
65                  70                  75                  80

Tyr Ala Leu Tyr Gln Ala Gly Ile His His Val Ile Leu Gly His Ser
                85                  90                  95

Glu Arg Arg Thr Tyr Phe Asn Glu Thr Asp Glu Leu Ile Asn Lys Lys
            100                 105                 110

Val Lys Ala Ala Leu Val Asn Gly Leu Cys Pro Ile Val Cys Cys Asp
        115                 120                 125
```

```
Asp Thr Met Arg Arg Arg Val Ala Gly Lys Lys Val His Trp Val Val
        130                 135                 140

Ser Arg Ile Leu Ala Asp Leu His Gly Leu Thr Asn Asp Glu Ile Cys
145                 150                 155                 160

His Val Thr Val Ala Tyr Glu Pro Ser Trp Ala Ile Gly Thr Gly Glu
                165                 170                 175

Ser Ala Asp Pro Glu Gln Ala Ala Glu Gly Cys Tyr Leu Ile Arg Gln
                180                 185                 190

Thr Ile Ser Asp Met Tyr Gly Asp Glu Val Ala Asn Asn Val Arg Ile
            195                 200                 205

Leu Tyr Gly Gly Ser Val Thr Thr Ser Asn Ile Asn Ala Leu Met Ala
        210                 215                 220

Lys Asn Asp Ile Asp Gly Val Leu Val Gly Ala Ala Ser Leu Asn Pro
225                 230                 235                 240

Glu Thr Phe Leu Gln Leu Val His His
                245
```

```
<210> SEQ ID NO 48
<211> LENGTH: 750
<212> TYPE: DNA
<213> ORGANISM: Lactobacillus reuteri

<400> SEQUENCE: 48
atgagagtac cgattattgc tggtaattgg aaaatgcata aggatgtaca agaagctgtc      60
tcttttatcg aaaagtaaa aaatcagctt ccgcctgccg accaacttga acagcaatt     120 gctgctccta ctctttgttt agtaccaatg gttaaagcag ctgaagaatc cccgttaaaa    180
ataatggcag aaaactgcta ctataagaat gagggagctt atactggtga aacaagtcca    240
tatgctttat accaagcagg aatccatcat gtgattttag gccattctga acgccgaact    300
tactttaatg aaactgatga attaattaat aaaaaagtga aggcagcatt agtaaatggg    360
ttatgtccga ttgtttgttg tgatgatact atgcgtcgac gagttgctgg aaagaaagtt    420
cattgggtgg tgagccgaat tctcgctgac cttcatggat tgaccaatga cgaaatttgt    480
catgttacgg ttgcttatga accaagttgg gcgattggaa caggcgagag tgctgatcca    540
gaacaagcgg cggaaggttg ttaccttatt cggcaaacga ttagtgatat gtatggcgat    600
gaagttgcaa ataacgttcg aattctctat ggcggaagtg tgacaacttc taatatcaat    660
gcactaatgg caaaaaatga tattgatggt gttttagtcg gagcggcgag cttaaatcca    720
gaaacatttt tacaattagt tcaccattag                                     750
```

```
<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caccatgaaa cgtcaaaaac gattt                                           25
```

```
<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 50
aaaagcttag ttatcgccct ttagc                                              25

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atggtgaaat tgatgacaat                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttatttaaat tgatcgccaa                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttgatttatg ttttaaaaga                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctatgaccga gttaaatact                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atggaaatta aaagtgttaa                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
ctaaattaaa ttcagttcag                                                  20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atgttcggtc acgatggccg                                                  20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcaaatttca gaaggatcat                                                  20
```

The invention claimed is:

1. A method of treating obesity, wherein the method comprises administering to a subject in need thereof a composition comprising a therapeutically effective amount of *Lactobacillus rhamnosus* ATCC 53103.

2. The method according to claim 1, wherein the therapeutically effective amount is $10^8$-$10^9$ CFU/day in terms of a bacterial number of *Lactobacillus rhamnosus* ATCC 53103.

3. The method according to claim 1, wherein the composition is a food.

4. The method according to claim 1, wherein the composition is a drink.

5. The method according to claim 1, wherein the *Lactobacillus rhamnosus* ATCC 53103 inhibits a lipid from being taken from a digestive tract.

6. The method according to claim 1, wherein the *Lactobacillus rhamnosus* ATCC 53103 has been transformed with a nucleic acid encoding a glycerol-degrading enzyme that is a glycerol dehydratase having an amino acid sequence that is any one of SEQ ID Nos. 10, 12 or 14.

7. The method according to claim 1, wherein the *Lactobacillus rhamnosus* ATCC 53103 has been transformed with a nucleic acid encoding an enteroadherent protein having an amino acid sequence that is SEQ ID No. 16.

8. The method according to claim 1, wherein the *Lactobacillus rhamnosus* ATCC 53103 has been transformed with a nucleic acid encoding a glycerol-degrading enzyme that is an alcohol dehydrogenase having an amino acid sequence that is any one of SEQ ID Nos. 18, 20, 22, 24, 26, 28 or 30.

9. The method according to claim 1, wherein the *Lactobacillus rhamnosus* ATCC 53103 has been transformed with a nucleic acid encoding a glycerol-degrading enzyme that is an aldehyde dehydrogenase having an amino acid sequence that is any one of SEQ ID Nos. 32, 34 or 36.

10. The method according to claim 1, wherein the *Lactobacillus rhamnosus* ATCC 53103 has been transformed with a nucleic acid encoding a glycerol-degrading enzyme that is a glycerate kinase having an amino acid sequence that is SEQ ID No. 38.

11. The method according to claim 1, wherein the *Lactobacillus rhamnosus* ATCC 53103 has been transformed with a nucleic acid encoding a glycerol-degrading enzyme that is a glycerol kinase having an amino acid sequence that is SEQ ID No. 40.

12. The method according to claim 1, wherein the *Lactobacillus rhamnosus* ATCC 53103 has been transformed with a nucleic acid encoding a glycerol-degrading enzyme that is a glycerol-3-phosphate dehydrogenase having an amino acid sequence that is SEQ ID No.

13. The method according to claim 1, wherein the *Lactobacillus rhamnosus* ATCC 53103 has been transformed with a nucleic acid encoding a glycerol-degrading enzyme that is a triosephosphate isomerase having an amino acid sequence that is any one of SEQ ID Nos. 44, 46 or 48.

* * * * *